(12) United States Patent
Ignatyev et al.

(10) Patent No.: US 7,939,644 B2
(45) Date of Patent: May 10, 2011

(54) CYANOBORATE, FLUOROALKYLPHOSPHATE, FLUOROALKYLBORATE OR IMIDE DYES

(75) Inventors: Nikolai (Mykola) Ignatyev, Duisburg (DE); Urs Welz-Biermann, Heppenheim (DE); Helge Willner, Muehlheim/Ruhr (DE); Maik Finze, Nienburg (DE); Eduard Bernhardt, Duisburg (DE); Andriy Kucheryna, Wuppertal (DE)

(73) Assignee: Merck Patent GmbH, Darmstadt (DE)

( * ) Notice: Subject to any disclaimer, the term of this patent is extended or adjusted under 35 U.S.C. 154(b) by 1302 days.

(21) Appl. No.: 10/568,526

(22) PCT Filed: Jul. 22, 2004

(86) PCT No.: PCT/EP2004/008174
§ 371 (c)(1),
(2), (4) Date: Feb. 17, 2006

(87) PCT Pub. No.: WO2005/021661
PCT Pub. Date: Mar. 10, 2005

(65) Prior Publication Data
US 2008/0275224 A1    Nov. 6, 2008

(30) Foreign Application Priority Data

Aug. 21, 2003 (DE) ............... 103 38 834
Aug. 21, 2003 (DE) ............... 103 38 933
Dec. 9, 2003 (DE) ............... 103 57 359
Dec. 9, 2003 (DE) ............... 103 57 360
Feb. 17, 2004 (DE) ......... 10 2004 007 610
Feb. 17, 2004 (DE) ......... 10 2004 007 611

(51) Int. Cl.
*C09B 23/00* (2006.01)
*C09B 23/04* (2006.01)
*C09B 23/06* (2006.01)
*C09B 23/08* (2006.01)
*C09B 23/16* (2006.01)
*C09B 44/10* (2006.01)
*C09B 44/14* (2006.01)
*C09B 44/16* (2006.01)
*C09B 44/18* (2006.01)
*C09B 44/20* (2006.01)

(52) U.S. Cl. ........ 534/607; 534/611; 548/156; 548/219; 548/455

(58) Field of Classification Search .................. None
See application file for complete search history.

(56) References Cited

U.S. PATENT DOCUMENTS

| | | | |
|---|---|---|---|
| 4,367,334 A | | 1/1983 | Loew et al. |
| 5,401,618 A | | 3/1995 | Chapman et al. |
| 5,541,235 A | * | 7/1996 | Busman et al. .................. 522/25 |
| 5,876,821 A | * | 3/1999 | Chapman et al. ........... 428/64.1 |
| 6,210,830 B1 | * | 4/2001 | Sartori et al. ................. 429/199 |
| 6,423,454 B1 | * | 7/2002 | Heider et al. ................. 429/345 |
| 6,841,301 B2 | * | 1/2005 | Heider et al. ................. 429/199 |
| 2008/0048155 A1 | * | 2/2008 | Toriniwa et al. .............. 252/587 |

FOREIGN PATENT DOCUMENTS

| | | |
|---|---|---|
| EP | 0 055 223 | 12/1981 |
| EP | 0 636 493 | 6/1994 |

OTHER PUBLICATIONS

Lubs, H. A., The Chemistry of Synthetic Dyes and Pigments, Reinhold Publishing Corporation, New York, 1955, pp. 248-254.*
Iwamoto et al. "Anion-catalyzed Phase-transfer Catalysis. I. Application to Diazo-coupling Reactions" Bull Chem. Soc. Japan, 56(3):796-801 (1983).
Yang et al. "Penetrated Ion Pairs: Photochemistry of Cyanine Dyes within Organic Borates" J. Am. Chem. Soc. 114:793-794 (1992).

* cited by examiner

*Primary Examiner* — Fiona T Powers
(74) *Attorney, Agent, or Firm* — Millen, White, Zelano & Branigan, P.C.

(57) ABSTRACT

The present invention relates to dyes of the general formula $CAT^+Y^-$ (I), where $Y^-$ is an anion selected from the group of the cyanoborates, fluoroalkylphosphates, fluoroalkylborates or imidates and $CAT^+$ is a cation selected from the group of the azine, xanthene, polymethine, styryl, azo, tetrazolium, pyrylium, benzopyrylium, thiopyrylium, benzothiopyrylium, thiazine, oxazine, triarylmethane, diarylmethane, methine, acridine, quinoline, isoquinoline or quaternary azafluorenone dyes, for colouring plastics and plastic fibres, for the preparation of flexographic printing inks, as ball-point pen pastes, as stamp ink, for colouring leather and paper, for use in data acquisition systems, reprography, in ink microfilters, in photogalvanics, laser technology and the photo industry.

11 Claims, No Drawings

CYANOBORATE, FLUOROALKYLPHOSPHATE, FLUOROALKYLBORATE OR IMIDE DYES

The present invention relates to cationic dyes having novel anions which can be used for colouring plastics and plastic fibres, for the preparation of flexographic printing inks, ballpoint pen pastes, stamp inks for colouring leather and paper in the traditional application, but also in photo and laser technology and in the electronics industry.

A multiplicity of dyes are known today. A distinction is made according to origin between natural and synthetic dyes. Known synthetic dyes are, for example, Aniline Blue, fuchsin or Methyl Orange. The dyes are designated (a) by the scientific names according to purely chemical points of view on the basis of the chromophore configuration (for example: azo, azine, anthraquinone, acridine, cyanine, oxazine, polymethine, thiazine, triarylmethane dyes); (b) according to the behaviour on the fibre and the dyeing technique to be used; basic or cationic dyes, mordant, direct, dispersion, ingrain, vat, metal-complex, reactive, acid or sulfur dyes; (c) according to the Colour Index with its number system (C. I. . . . ) or the word/number system (Acid Red . . . ); (d) by names which are generally protected as trademarks (commercial dye designation); for example: Sirius, Anthrasol, Erio, Indanthrene, Remazol, Basilen, Levafix, Cibacron, Drimaren or Procion dyes.

Most synthetic dyes are aromatic or heterocyclic and either ionic (for example all water-soluble dyes) or nonionic compounds (for example dispersion dyes). In the case of ionic dyes, a distinction is made between anionic and cationic dyes.

Cationic dyes consist of organic cations with positive charges which are delocalised over conjugated bonds and an anion, usually inorganic. These are usually dyes whose amino groups, which may also be substituted, are involved in the resonance. The selection of known cationic dyes is large, whereas the number of anions is restricted to chlorides, bromides, iodides, perchlorates, tetrafluoroborates, hexafluorophosphates, alkyl- or arylsulfates, in particular tosylates, acetates or oxalates, as described in H. Zollinger, Color Chemistry, VCH, Weinheim 1991.

Known cationic dyes are, for example, rhodamine, safranine or Victoria Blue, which usually have chloride ions or tosylates as counterion. These compounds are not very electrochemically stable. Attempts are found in the prior art to introduce novel anions which make dyes more electrochemically stable. However, the anions employed, such as $(BF_4)^-$ or $(PF_6)^-$, have other disadvantages. Dyes having tetrafluoroborate anions are less thermally stable and have poor solubility in organic solvents. Dyes having hexafluorophosphate anions have neither good thermal nor good hydrolysis stability.

JP-A-2-3052 describes the dye 3,3'-diethoxyethyl-2,2'-thiadicarbocyanine trifluoromethyltrifluoroborate as photopolymerisation initiator. These and similar compounds were synthesised in order to obtain air-stable initiators which are able to initiate polymerisation on irradiation with light having wavelengths of 600-900 nm or more.

The object of the present invention was to provide dyes which are electrochemically stable, thermally stable and hydrolysis stable and have good solubility in organic solvents.

The object is achieved by cationic dyes of the general formula (I):

$$CAT^+Y^- \qquad (I),$$

where $Y^-$ is an anion selected from the group $CAB^-$, $FAP^-$, $FAB^-$ or $Im^-$, where $CAB^-$ conforms to the general formula (II-1)

$$[B(CN)_{y1}F_{4-y1-x1}(R^0)_{x1}]^- \qquad (II-1)$$

and
y1 denotes 1, 2, 3 or 4,
x1 denotes 0, 1, 2 or 3 and
$R^0$ denotes alkyl, aryl, fluorinated alkyl, fluorinated aryl, cycloalkyl or alkylaryl, with the condition that $R^0$ may be hydrogen if y1 is >2, where $FAP^-$ conforms to the general formula (II-2)

$$[P(C_{p2}F_{2p2+1-m2}H_{m2})_{y2}F_{6-y2}]^- \qquad (II-2).$$

with
p2: 1 to 20,
m2: 0, 1, 2 or 3 and
y2: 1, 2, 3 or 4,
where $FAB^-$ conforms to the general formula (II-3)

$$[B(C_{p3}F_{2p3+1-m3}H_{m3})_{y3}F_{4-y3}]^- \qquad (II-3)$$

with
p3 1 to 20,
m3 0, 1, 2 or 3 and
y3 1, 2, 3 or 4,
where $Im^-$ conforms to the general formula (II-4)

$$[(C_{p4}F_{2p4+1-m4}H_{m4}XO_{y4})N(C_qF_{2q+1-k}H_kXO_{y4})]^- \qquad (II-4)$$

and the variables
X denotes carbon or sulfur,
p4 denotes 0 to 20 and $0 \leq m4 \leq 2p4+1$,
q denotes 0 to 20 and $0 \leq k \leq 2q+1$,
y4 denotes 1 or 2,
where m4=0 if p4=0 and k=0 if q=0,
with the proviso
if X is sulfur, y4 denotes 2 and if X is carbon, y4 denotes 1 and p4 or q≧1, and where the carbon atoms of the alkyl chain of the formula II-4 may be bonded to one another by single bonds, where the resultant alkylene chain may in turn be partially or fully substituted by F, and
$CAT^+$ is a cation selected from the group of the azine, xanthene, polymethine, styryl, azo, tetrazolium, pyrylium, benzopyrylium, thiopyrylium, benzothiopyrylium, thiazine, oxazine, triarylmethane, diarylmethane, acridine, quinoline, isoquinoline or quaternised azafluorenone dyes, where 3,3'-diethoxyethyl-2,2'-thiadicarbocyanine trifluoromethyltrifluoroborate is excluded.

The cyanoborate anions, abbreviated below as CAB anions ($CAB^-$), and processes for their preparation are known from E. Bernhardt, G. Henkel, H. Willner, Z. Anorg. Allg. Chem. 626 (2000) 560; D. Williams, B. Pleune, J. Kouvetakis, M. D. Williams, R. A. Andersen, J. Amer. Chem. Soc. 122 (2000) 7735; E. Bernhardt, M. Berkei, M. Schürmann, H. Willner, Z. Anorg. Allg. Chem. 628 (2002) 1734) and E. Bernhardt, G. Henkel, H. Willner, G. Pawelke, H. Bürger, Chem. Eur. J. 7 (2001) 4696; G. Pawelke, H. Bürger, Coord. Chem. Rev. 215 (2001) 243) or can be prepared analogously to these processes.

In formula II-1, y1 is preferably 1 or 4, particularly preferably 4. In formula II-1, x1 is preferably 2 or 3, particularly preferably 3.

Anions $CAB^-$ are, for example, $[B(CN)_4]^-$, $[B(CN)F_3]^-$, $[B(CN)_2F_2]^-$ or $[B(CN)_3F]^-$, $[B(CN)(CF_3)_3]^-$, $[B(CN)_2(CF_3)_2]^-$, $[B(CN)(C_2F_5)_3]^-$, $[B(CN)_2(C_2F_5)_2]^-$, $[B(CN)(C_3F_7)_3]^-$, $[B(CN)_2(C_3F_7)_2]^-$, $[B(CN)(C_4F_9)_3]^-$, $[B(CN)_2(C_4F_9)_2]^-$, $[B(CN)(CH_3)_3]^-$, $[B(CN)_2(CH_3)_2]^-$, $[B(CN)(C_2H_5)_3]^-$, $[B(CN)_2(C_2H_5)_2]^-$, $[B(CN)(C_3H_7)_3]^-$, $[B(CN)_2$ $(C_3H_7)_2]^-$, $[B(CN)(C_4H_9)_3]^-$, $[B(CN)_2(C_4H_9)_2]^-$, $[B(CN)(C_6H_{13})_3]^-$, $[B(CN)(CHF_2)_3]^-$, $[B(CN)_2(CHF_2)_2]^-$, $[B(CN)(CH_2CF_3)_3]^-$, $[B(CN)_2(CH_2CF_3)_2]^-$, $[B(CN)(CH_2C_2F_5)_3]^-$, $[B(CN)_2(CH_2C_2F_5)_2]^-$, $[B(CN)_2(CH_2CH_2C_3F_7)_2]^-$, $[B(CN)_2 (CH_2C_3F_7)_2]^-$ or $[B(CN)(C_6H_5)_3]^-$.

CAB$^-$ is particularly preferably $[B(CN)(CF_3)_3]^-$, $[B(CN)F_3]^-$, $[B(CN)_2F_2]^-$ or $[B(CN)_4]^-$.

CAB$^-$ is very particularly preferably $[B(CN)_4]^-$.

The fluoroalkylphosphate anions, abbreviated below as FAP anions, and processes for their preparation are known from EP 0929558 B1 and U.S. Pat. No. 6,423,454.

In formula II-2, p2 is preferably 1, 2, 3, 4, 5, 6, 7 or 8, particularly preferably 2, 3 or 4.

Particularly preferred FAP anions are $^-PF_3(C_2F_5)_3$, $^-PF_3(C_4F_9)_3$, $^-PF_3(C_3F_7)_3$ or $^-PF_4(C_2F_5)_2$.

The fluoroalkylborate anions, abbreviated below as FAB anions, and processes for their preparation are known from EP 1174941, EP 1205480 and EP 1229038.

In formula II-3, m3 is preferably 0 and p3 is preferably 1, 2, 3, 4, 5, 6, 7 or 8, particularly preferably 1 or 2, where trifluoromethyltrifluoroborate is excluded.

Particularly preferred FAB anions are $[B(CF_3)_4]^-$, $[B(C_2F_5)_4]^-$, $[BF_3(C_2F_5)]^-$, $[BF_2(CF_3)_2]^-$, $[BF_2(C_2F_5)_2]^-$, $[BF_2(CH_3)_2]^-$, $[BF(C_2F_5)_3]^-$, $[BF(CF_3)_3]^-$ or $[BF(CF_3)(C_2F_5)_2]^-$. FAB$^-$ is very particularly preferably $[B(CF_3)_4]^-$.

The imide anions, abbreviated below as Im anions (Im$^-$), and processes for their preparation are known from U.S. Pat. Nos. 5,874,616, 5,723,664, 5,072,040, 4,387,222, EP 1363345 or from H. Matsumoto et al, Chem. Commun., 2002, 1726-1727. The synthesis of the cyclic imides is known from WO 97/31909, R. Jaeschke, G. Henkel, P. Sartori, Z. Naturforsch, 52 (1997), 359-366 or S. Sukhijinder et al, J. Am. Chem. Soc. 109 (1987), 7194-7196.

In formula II-4, p4 and q are each, independently of one another, preferably 1, 2, 3, 4, 5, 6, 7, 8, 9, 10, 11 or 12, particularly preferably 1, 2 or 4.

Cyclic imides of the formula II-4 form a four-, five-, six- or seven-membered ring, where the hydrogen atoms of the resultant alkylene chain may be partially or fully replaced by F. Preference is given to cyclic imides which form a six-membered ring.

Without restricting generality, examples of the Im anions are
$[(FSO_2)_2N]^-$, $[(FSO_2)N(CF_3SO_2)]^-$, $[(CF_3SO_2)_2N]^-$, $[(CF_3CO)N(CF_3SO_2)]^-$, $[(CF_3CO)_2N]^-$, $[(CH_3SO_2)_2N]^-$, $[(CHF_2SO_2)_2N]^-$, $[(CH_3CO)N(CF_3SO_2)]^-$, $[(CH_3CO)N(CH_3SO_2)]^-$, $[(CF_3CO)N(CH_3SO_2)]^-$, $[(C_2F_5SO_2)_2N]^-$, $[(C_2H_5SO_2)_2N]^-$, $[(C_2F_5SO_2)N(CF_3SO_2)]^-$, $[(C_2F_5SO_2)N(CF_3CO)]^-$, $[(C_2F_5SO_2)N(C_2F_5CO)]^-$, $[(C_2F_5SO_2)N(CH_3SO_2)]^-$, $[(C_2F_5SO_2)N(C_2H_5SO_2)]^-$, $[(C_2H_5SO_2)N(CF_3SO_2)]^-$, $[(C_2F_5SO_2)N(CH_3CO)]^-$, $[(C_2F_5SO_2)N(C_2H_5CO)]^-$, $[(C_2F_5CO)_2N]^-$, $[(C_3F_7SO_2)_2N]^-$, $[(C_3F_7SO_2)N(CF_3SO_2)]^-$, $[(C_4F_9SO_2)_2N]^-$, $[(C_4F_9CO)_2N]^-$, $[(C_4F_9SO_2)N(CF_3SO_2)]^-$, $[(C_4H_9SO_2)N(CF_3SO_2)]^-$, $[(C_4F_9SO_2)N(CF_3CO)]^-$, $[(C_4F_9CO)N(CF_3CO)]^-$,

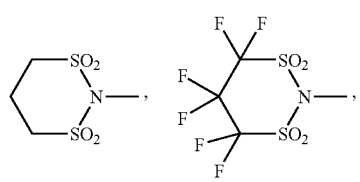

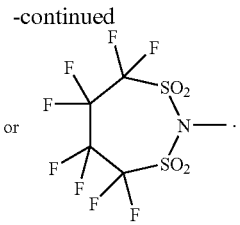

Particularly preferred Im anions are
$[(CF_3SO_2)_2N]^-$, $[(C_2F_5SO_2)_2N]^-$, $[(C_4F_9SO_2)_2N]^-$, $[(C_2F_5SO_2)N(CF_3SO_2)]$ or $[(C_4F_9SO_2)N(CF_3SO_2)]^-$.

The anion Y$^-$ therefore preferably denotes $[B(CN)_4]^-$, $[B(CN)F_3]^-$, $[B(CN)_2F_2]^-$ or $[B(CN)_3F]^-$, $[B(CN)(CF_3)_3]^-$, $[B(CN)_2(CF_3)_2]^-$, $[B(CN)(C_2F_5)_3]^-$, $[B(CN)_2(C_2F_5)_2]^-$, $[B(CN)(C_3F_7)_3]^-$, $[B(CN)_2(C_3F_7)_2]^-$, $[B(CN)(C_4F_9)_3]^-$, $[B(CN)_2(C_4F_9)_2]^-$, $[B(CN)(CH_3)_3]^-$, $[B(CN)_2(CH_3)_2]^-$, $[B(CN)(C_2H_5)_3]^-$, $[B(CN)_2(C_2H_5)_2]^-$, $[B(CN)(C_3H_7)_3]^-$, $[B(CN)_2(C_3H_7)_2]^-$, $[B(CN)(C_4H_9)_3]^-$, $[B(CN)_2(C_4H_9)_2]^-$, $[B(CN)(C_6H_{13})_3]^-$, $[B(CN)(CHF_2)_3]^-$, $[B(CN)_2(CHF_2)_2]^-$, $[B(CN)(CH_2CF_3)_3]^-$, $[B(CN)_2(CH_2CF_3)_2]^-$, $[B(CN)(CH_2C_2F_5)_3]^-$, $[B(CN)_2(CH_2C_2F_5)_2]^-$, $[B(CN)_2(CH_2CH_2C_3F_7)_2]^-$, $[B(CN)_2(CH_2C_3F_7)_2]^-$, $[B(CN)(C_6H_5)_3]^-$, $^-PF_3(C_2F_5)_3$, $^-PF_3(C_4F_9)_3$, $^-PF_3(C_3F_7)_3$, $^-PF_4(C_2F_5)_2$, $[B(CF_3)_4]^-$, $[B(C_2F_5)_4]^-$, $[BF_3(C_2F_5)]^-$, $[BF_2(CF_3)_2]^-$, $[BF_2(C_2F_5)_2]^-$, $[BF_2(CH_3)_2]^-$, $[BF(C_2F_5)_3]^-$, $[BF(CF_3)_3]^-$, $[BF(CF_3)(C_2F_5)_2]^-$, $[(FSO_2)_2N]^-$, $[(FSO_2)N(CF_3SO_2)]^-$, $[(CF_3SO_2)_2N]^-$, $[(CF_3CO)N(CF_3SO_2)]^-$, $[(CF_3CO)_2N]^-$, $[(CH_3SO_2)_2N]^-$, $[(CHF_2SO_2)_2N]^-$, $[(CH_3CO)N(CF_3SO_2)]^-$, $[(CH_3CO)N(CH_3SO_2)]^-$, $[(CF_3CO)N(CH_3SO_2)]^-$, $[(C_2F_5SO_2)_2N]^-$, $[(C_2H_5SO_2)_2N]^-$, $[(C_2F_5SO_2)N(CF_3SO_2)]^-$, $[(C_2F_5SO_2)N(CF_3CO)]^-$, $[(C_2F_5SO_2)N(C_2F_5CO)]^-$, $[(C_2F_5SO_2)N(CH_3SO_2)]^-$, $[(C_2F_5SO_2)N(C_2H_5SO_2)]^-$, $[(C_2H_5SO_2)N(CF_3SO_2)]^-$, $[(C_2F_5SO_2)N(CH_3CO)]^-$, $[(C_2F_5SO_2)N(C_2H_5CO)]^-$, $[(C_2F_5CO)_2N]^-$, $[(C_3F_7SO_2)_2N]^-$, $[(C_3F_7SO_2)N(CF_3SO_2)]^-$, $[(C_4F_9SO_2)_2N]^-$, $[(C_4F_9CO)_2N]^-$, $[(C_4F_9SO_2)N(CF_3SO_2)]^-$, $[(C_4F_9SO_2)N(CH_3SO_2)]^-$, $[(C_4H_9SO_2)N(CF_3SO_2)]^-$, $[(C_4F_9SO_2)N(CF_3CO)]^-$, $[(C_4F_9CO)N(CF_3CO)]^-$, Y$^-$ is particularly preferably $[B(CN)(CF_3)_3]^-$, $[B(CN)F_3]^-$, $[B(CN)_2F_2]^-$, $[B(CN)_4]^-$, $^-PF_3(C_2F_5)_3$, $^-PF_3(C_4F_9)_3$, $^-PF_3(C_3F_7)_3$, $^-PF_4(C_2F_5)_2$, $[B(CF_3)_4]^-$, $[B(C_2F_5)_4]^-$, $[(CF_3SO_2)_2N]^-$, $[(C_2F_5SO_2)_2N]^-$, $[(C_4F_9SO_2)_2N]^-$, $[(C_2F_5SO_2)N(CF_3SO_2)]^-$ or $[(C_4F_9SO_2)N(CF_3SO_2)]^-$; very particularly preferably $[B(CN)_4]^-$, $^-PF_3(C_2F_5)_3$, $[B(CF_3)_4]^-$ or $[(CF_3SO_2)_2N]^-$.

Preference is given in accordance with the invention to a group of compounds of the formula I where Y⁻ in each case has one of the meanings indicated or preferably described in the case of formula I and in which CAT⁺ is a cation of an azine dye.

Compounds having an azine skeleton are, for example, compounds based on phenazine

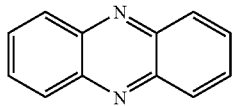

or
quinoxaline

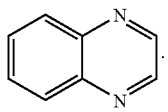

From the group of the phenazines, preference is in turn given to safranines, indulines and nigrosines.

Preferred cations can be described by the formula III

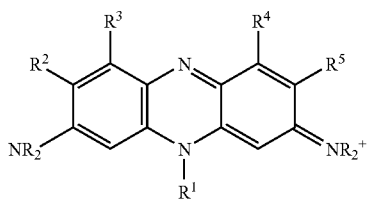

where
R in each case, independently of one another, denotes H, alkyl or aryl,
$R^1$ denotes hydrogen or aryl,
$R^2$, $R^3$, $R^4$, $R^5$ each, independently of one another, denote H, alkyl, aryl or $NR_2$.

In the formulae above or below, alkyl denotes an alkyl group which is linear or branched and has 1 to 20 C atoms, preferably 1 to 12 C atoms, particularly preferably 1, 2, 3 or 4 C atoms, and is optionally fully or partially fluorinated. Alkyl preferably denotes methyl, furthermore ethyl, isopropyl, propyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl or hexyl. Optionally fluoromethyl, difluoromethyl, trifluoromethyl, pentafluoroethyl, heptafluoropropyl or nonafluorobutyl. Particular preference is given to methyl or ethyl.

In the formulae below, alkenyl stands for a straight-chain or branched alkenyl having 2 to 20 C atoms, in which a plurality of double bonds may also be present, preferably for allyl, 2- or 3-butenyl, isobutenyl, sec-butenyl, preference is furthermore given to 4-pentenyl, isopentenyl or 5-hexenyl.

In the formulae below, alkynyl stands for a straight-chain or branched alkynyl having 2 to 20 C atoms, in which a plurality of triple bonds may also be present, preferably for ethynyl, 1- or 2-propynyl, 2- or 3-butynyl, preference is furthermore given to 4-pentynyl, 3-pentynyl or 5-hexynyl.

In alkylaryl, aryl has one of the preferred meanings indicated below. Particular preference for alkylaryl is given to benzyl, 4-methoxyphenylethyl, 3-methoxyphenylethyl, 2-methoxybenzyl, 3-methoxybenzyl, 4-methoxybenzyl, 2-ethoxybenzyl, 2-methylbenzyl, 3-methylbenzyl, 4-tert-butylbenzyl, 2-(trifluoromethyl)benzyl, 3-(trifluoromethyl)benzyl, 4-fluorobenzyl, 3-iodobenzyl, 4-(trifluoromethoxy)benzyl, 3-(trifluoromethoxy)benzyl or 4-(trifluoromethylsulfanyl)benzyl.

In the formulae above or below, aryl preferably denotes phenyl which is mono-, di- or trisubstituted by Z, where Z can denote hydrogen, alkyl, $NO_2$, F, Cl, Br, I, OH, carboxyl, alkoxy, $OCF_3$, SCN, $SCF_3$, C(O)Oalkyl, $CH_2$—C(O)Oalkyl, amino or alkylamino. The definition of aryl also includes perfluorinated aryl, in particular perfluorinated phenyl.

Aryl therefore preferably denotes phenyl, o-, m- or p-methylphenyl, o-, m- or p-ethylphenyl, o-, m- or p-propylphenyl, o-, m- or p-isopropylphenyl, o-, m- or p-tert-butylphenyl, o-, m- or p-aminophenyl, o-, m- or p-(N,N-dimethylamino)phenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfanyl)phenyl, o-, m- or p-fluorophenyl, o-, m- or p-chlorophenyl, o-, m- or p-bromophenyl, o-, m- or p-iodophenyl, furthermore preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In the formulae below, arylalkyl denotes aryl which is mono- or polysubstituted by alkyl having 1-4 C atoms.

In the formulae below, carbocycle denotes an unsaturated mono- or bicyclic radical having 5 to 14 ring members, preferably cyclopentenyl, cyclopentadienyl, cyclohexenyl, 1,3- or 1,4-cyclohexadienyl, phenyl, cycloheptatrienyl, cyclooctenyl, indenyl, fluorenyl, naphthyl, anthracenyl or phenanthrenyl, which may be mono- or polysubstituted by Z as described above.

In the formulae above or below, cycloalkyl denotes a cycloalkyl group having 3 to 8 C atoms, preferably cyclopropyl, cyclobutyl, cyclopentyl, cyclohexyl, cycloheptyl or cyclooctyl.

In the formulae below, cycloalkylene denotes a cycloalkyl group having 5 to 8 C atoms which is partially unsaturated. Preferably cyclopent-1-enyl, cyclohex-1-enyl, cyclohex-1,3-dienyl, cyclohex-1,4-dienyl, cyclohept-1-enyl or cyclooct-1-enyl.

In the formulae below, heteroaryl denotes an unsaturated mono- or bicyclic heterocyclic radical having 5 to 13 ring members, which may contain 1, 2 or 3 N and/or 1 or 2 S or O atoms and in which the heterocyclic radical may be mono- or polysubstituted by Z as described above.

Heteroaryl is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H- indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl.

Particularly preferred cations CAT⁺ which are based on the phenazine skeleton are the following cations:

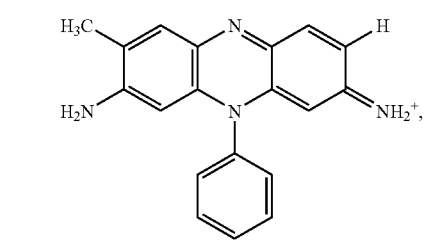

3a)

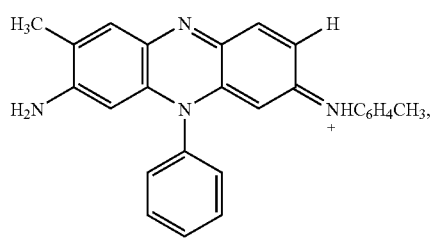

3b)

lp;1p

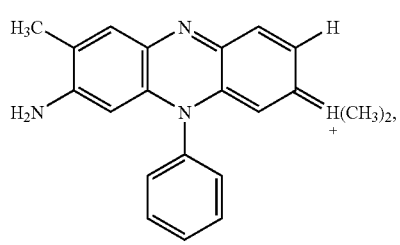

3c)

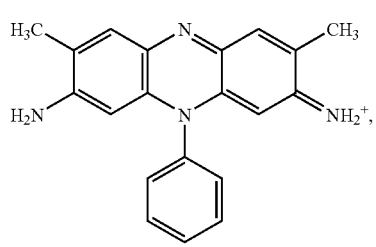

3d)

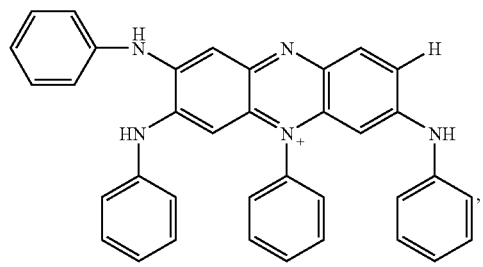

3e)

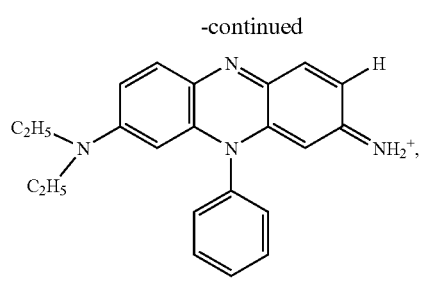

3f)

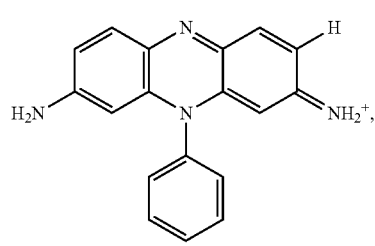

3g)

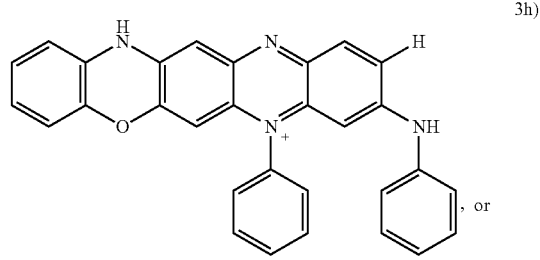

3h)

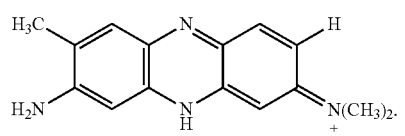

3i)

Preference is given in accordance with the invention to a group of compounds of the formula I where Y⁻ in each case has one of the meanings indicated or preferably described in the case of formula I and in which CAT⁺ is a cation of a xanthene dye.

Preferred cations can be described by the formula IV

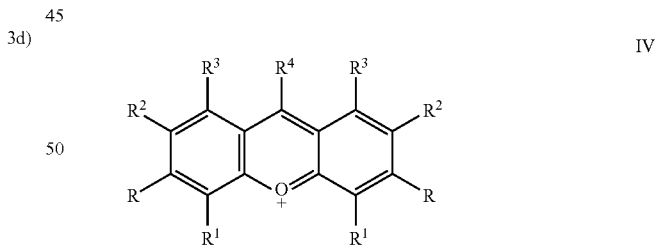

IV where

R in each case, independently of one another, denotes H, alkyl, alkenyl, aryl, heteroaryl, OH, Oalkyl, OC(O)alkyl, NH₂, NH-alkyl, NH-aryl, NH-heteroaryl, Cl or Br, R¹ in each case, independently of one another, denotes H, alkyl, aryl, alkylaryl, OH, Oalkyl, OC(O)alkyl, Cl, Br or I, R² in each case, independently of one another, denotes H, alkyl, aryl, OH, Oalkyl, OC(O)alkyl, OC(O)aryl, CN, NO₂, Cl, Br or I, R³ in each case, independently of one another, denotes H, alkyl, alkenyl, aryl, OH, Oalkyl, Cl, Br or I, R⁴ in each case, independently of one another, denotes H, alkyl, alkenyl, aryl, heteroaryl, alkylaryl, CH₂C(O)H, COOH, COOalkyl, Coocycloalkyl, COOaryl, COOheteroaryl, Oalkyl, Cl, Br or I.

Adjacent R, R¹, R², R³ or R⁴ may be bonded to one another by means of single or double bonds.

Particularly preferred compounds from the group of the xanthenes are compounds of the formula IVa

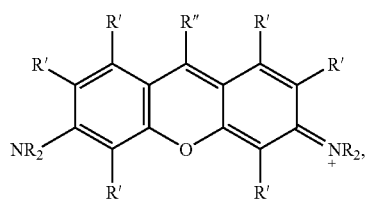

in which
R in each case, independently of one another, denotes H, alkyl, alkenyl, aryl or partially COOH-substituted alkyl,
R' in each case, independently of one another, denotes H, alkyl, alkenyl, aryl, aryl-COOR, NH₂, NH-alkyl, NH-aryl, NH-heteroaryl or N(alkyl)₂,
R" in each case, independently of one another, denotes H, alkyl, alkenyl, aryl, heteroaryl, partially COOR-substituted alkyl or aryl-COOR.

R is in each case, independently, particularly preferably H or alkyl. R' is in each case, independently, particularly preferably H or alkyl. R" is particularly preferably aryl which is substituted by at least one substituent COOR and may optionally be further substituted by Z, where Z has one of the meanings indicated above in the case of aryl.

Adjacent R, R' or R" may be bonded to one another by means of single or double bonds.

Particularly preferred cations CAT⁺ which are based on the xanthene skeleton are the following cations:

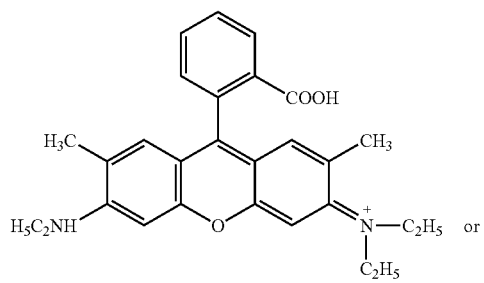

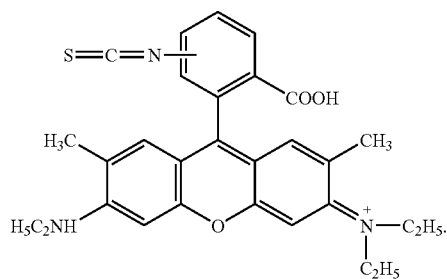

Preference is given in accordance with the invention to a group of compounds of the formula I where Y⁻ in each case has one of the meanings indicated or preferably described in the case of formula I and in which CAT⁺ is a cation of a polymethine dye.

The group of the polymethine dyes includes the cyanine, carbocyanine, azacarbocyanine, diazacarbocyanine, triazacarbocyanine, hemicyanine and diazahemicyanine dyes. The hemicyanine dyes are a selected group of the styryl dyes and may also be classified as the latter. The diazahemicyanine dyes are a selected group of the azo dyes and may also be classified as the latter.

Preferred cations of cyanine dyes can be described by the formula V-1

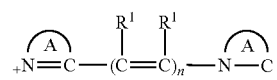

where
n denotes 0, 1, 2, 3, 4 or 5,
R¹ in each case, independently of one another, denotes H, Cl, Br, I, alkyl, partial or fully chlorinated alkyl, alkenyl, cycloalkyl, aryl, heteroaryl, Oalkyl, Oaryl, Salkyl, Saryl, NHalkyl, N(alkyl)₂, C(O)H, C(O)alkyl, C(O)aryl, CN, N=N-aryl, P(aryl)₂, NHCOalkyl or NHCOaryl and the ring system, represented by

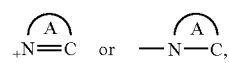

denotes a nitrogen-containing unsaturated mono-, bi- or tricyclic heterocycle having 5 to 13 ring members, which may furthermore contain 1, 2 or 3 N and/or 1 or 2 S or O atoms and in which the heterocyclic radical may be mono- or polysubstituted by Z as described above.
n is particularly preferably 1.

A particularly preferred cation CAT⁺ from the group of the cyanine dyes is:

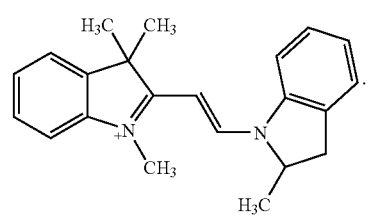

Preferred cations of carbocyanine dyes can be described by the formula V-2

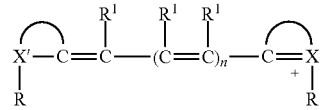

where
X denotes N, O or S,
X' denotes N, O, S or C,
n denotes 0, 1, 2, 3, 4 or 5, R in each case, independently of one another, denotes alkyl, alkenyl, cycloalkyl, aryl or heteroaryl and $R^1$ in each case, independently of one another, denotes H, Cl, Br, I, alkyl, partially or fully chlorinated alkyl, alkenyl, cycloalkyl, aryl, heteroaryl, Oalkyl, Oaryl, Salkyl, Saryl, NHalkyl, N(alkyl)$_2$, C(O)H, C(O)alkyl, C(O)aryl, CN, N=N-aryl, P(aryl)$_2$, NHCOalkyl or NHCOaryl.

The respective radicals R and/or $R^1$ may each be bonded to one another or to a substituent of the ring system by means of single or double bonds. For the excerpt of the formula

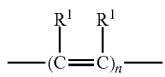

with n=2, this means that a cyclohexene or cyclopentene may be present in the compound, such as, for example,

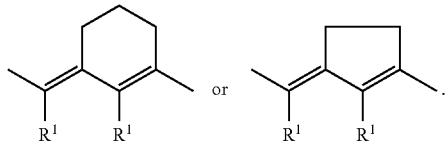

The ring system, represented by

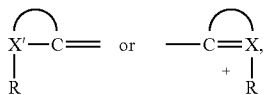

denotes an unsaturated mono-, bi- or tricyclic heterocycle having 5 to 13 ring members, which may contain 1, 2 or 3 N and/or 1 or 2 S or O atoms and in which the heterocyclic radical may be mono- or polysubstituted by Z as described above.

The ring system preferably denotes pyridine, quinoline, α-pyran, γ-thiopyran, thiazole, pyrrole, imidazole or oxazole, which may furthermore be fused to a phenyl. The ring closure may exist not only between nitrogen and the adjacent carbon, but also between nitrogen and the following carbon atoms in the chain or the $R^1$ radicals if these contain carbon, or between carbon atoms with formation of aromatic systems.

Particularly preferred ring systems are 3,3-dimethyl-3H-indole, 1,1-dimethyl-1H-benzo[e]indole, benzo[cd]indole, benzothiazole, benzoxazole, benzimidazole or benzopyridine, which may optionally be further substituted by Z. Z here is particularly preferably alkyl or Cl.

n is preferably 1, 2 or 3.

$R^1$ in formula V-2 is preferably alkyl, Cl, Oalkyl, Oaryl, Saryl or aryl.

R in formula V-2 is in each case, independently, preferably methyl, ethyl, propyl or butyl, where the respective alkyl may optionally be substituted by SO$_3$H or COOH.

Particularly preferred cations CAT$^+$ from the group of the carbocyanine dyes are:

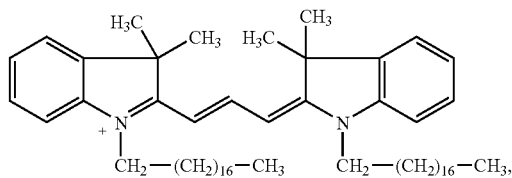
5a)

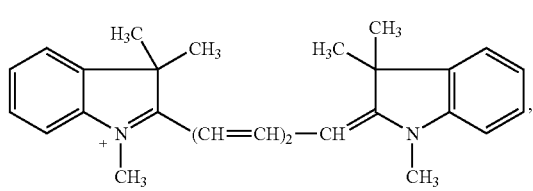
5b)

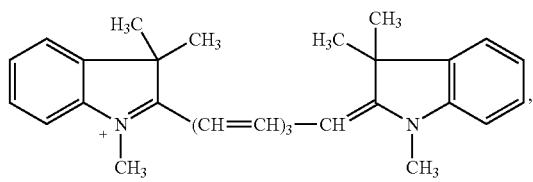
5c)

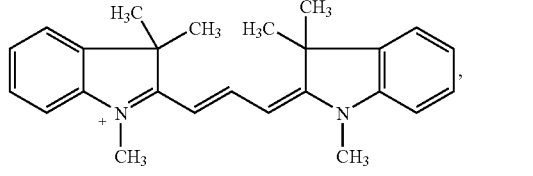
5d)

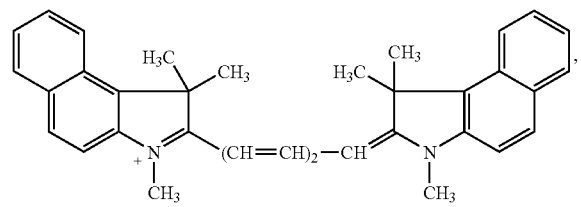
5e)

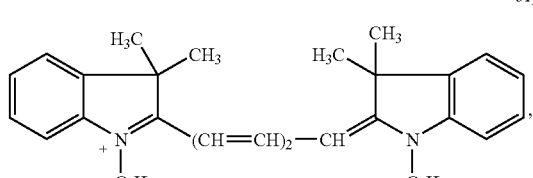
5f)

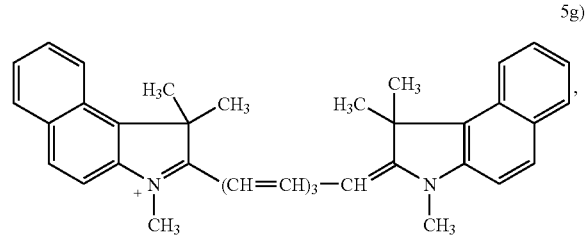
5g)

-continued
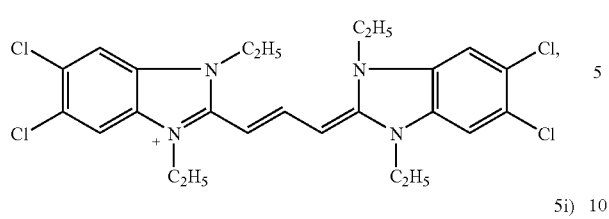
5h)
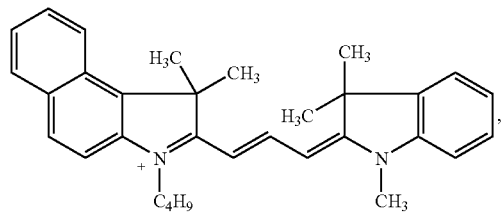
5i)
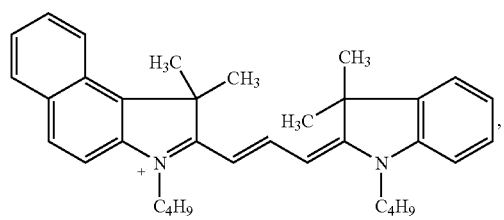
5j)
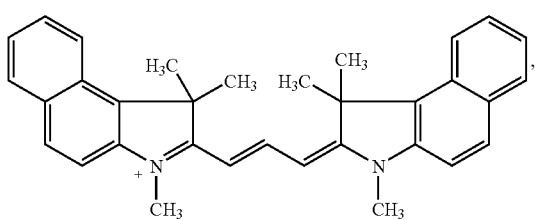
5k)
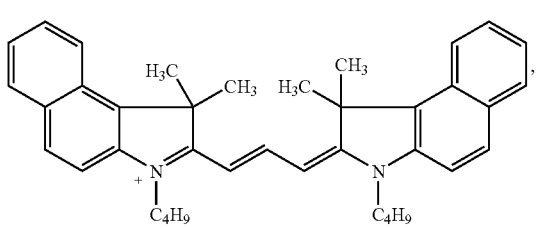
5l)
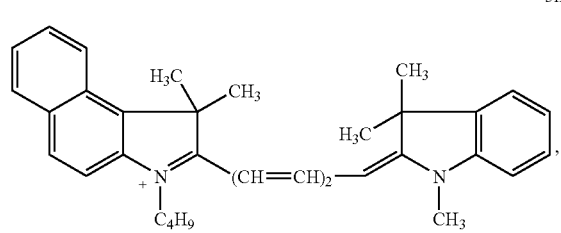
5m)
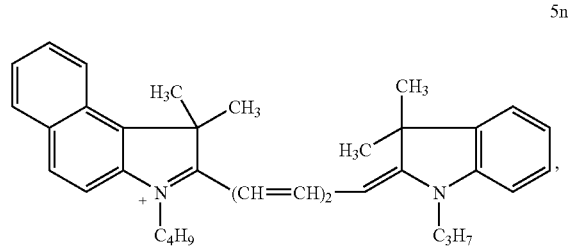
5n)
-continued
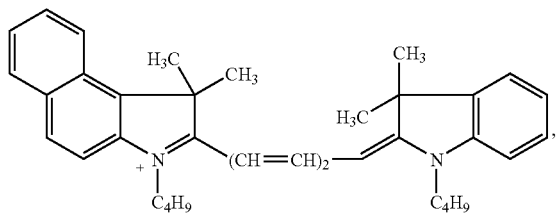
5o)
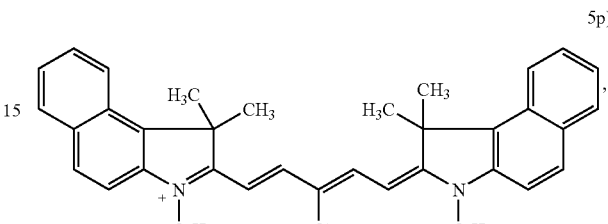
5p)
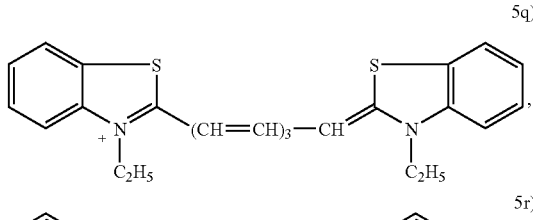
5q)
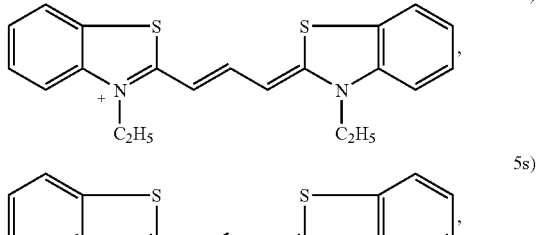
5r)
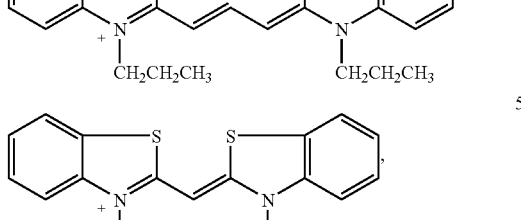
5s)
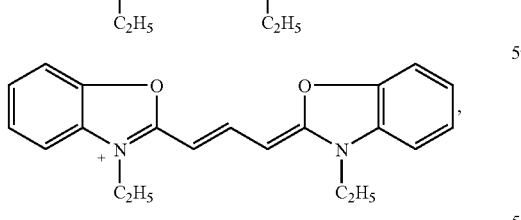
5t)
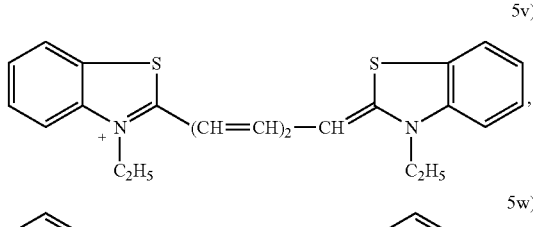
5u)
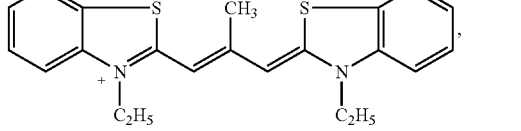
5v)
5w)

5x)
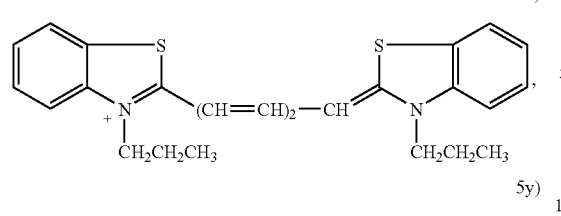
5y)
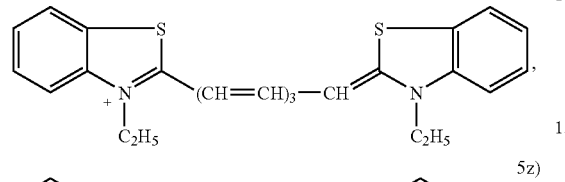
5z)
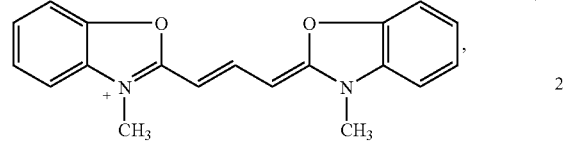
5.1)
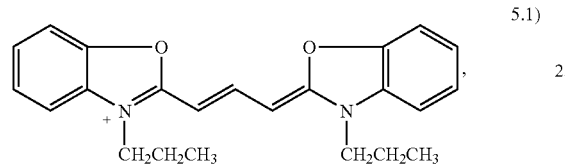
5.2)
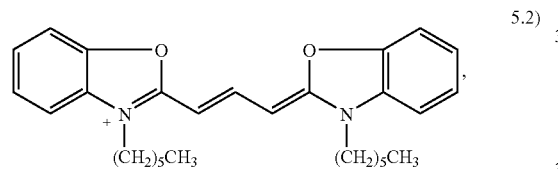
5.3)
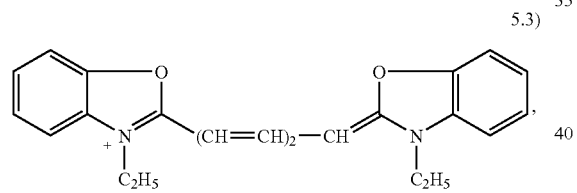
5.4)
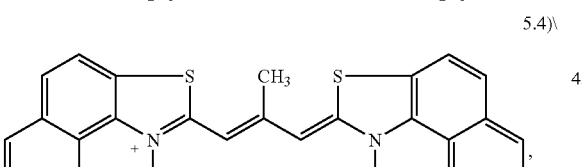
5.5)
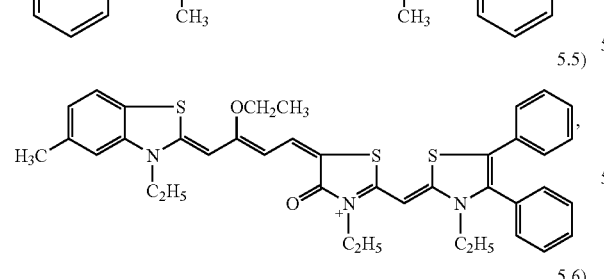
5.6)
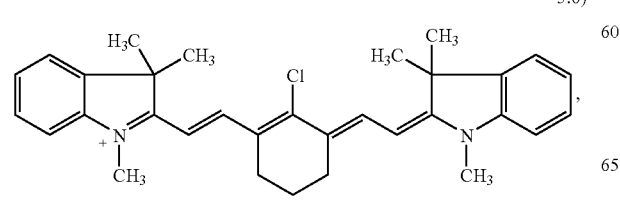
5.7)
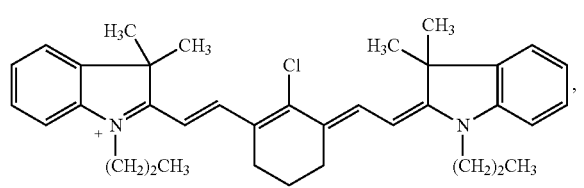
5.8)
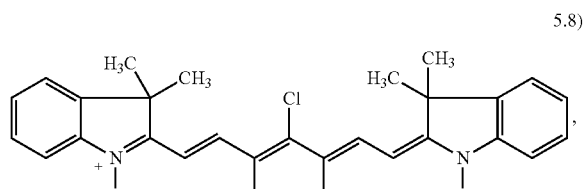
5.9)
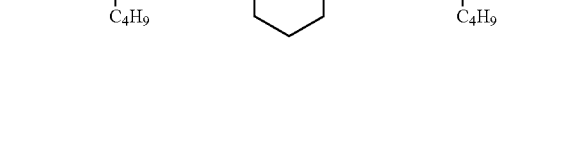
5.10)
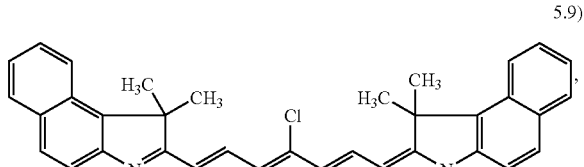
5.11)
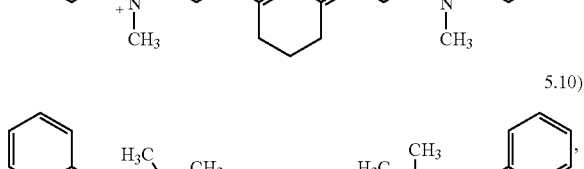
5.12)
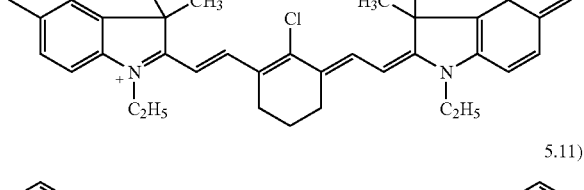
5.13)
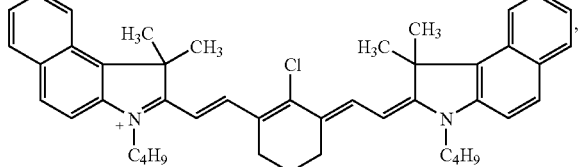

5.14)
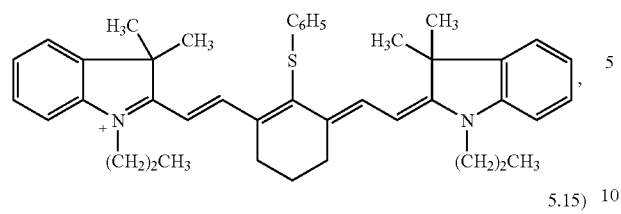
5.15)
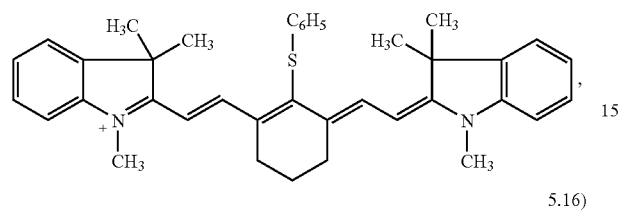
5.16)
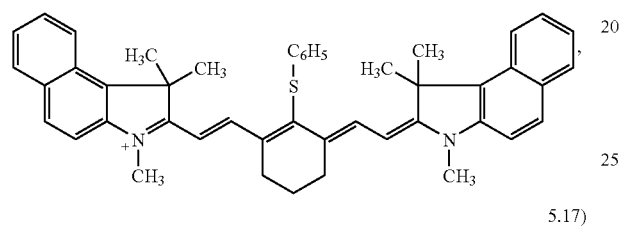
5.17)
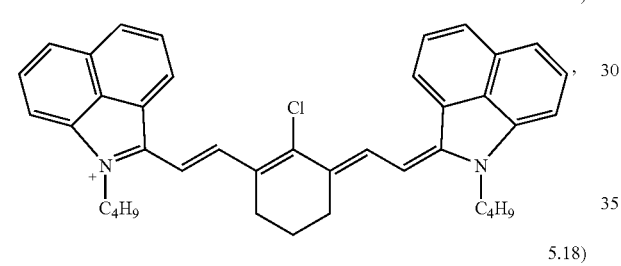
5.18)
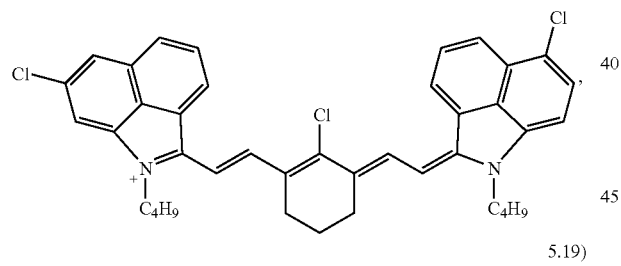
5.19)
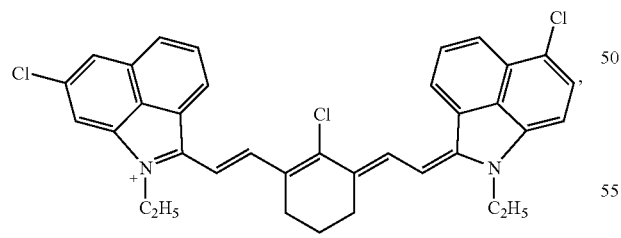
5.20)
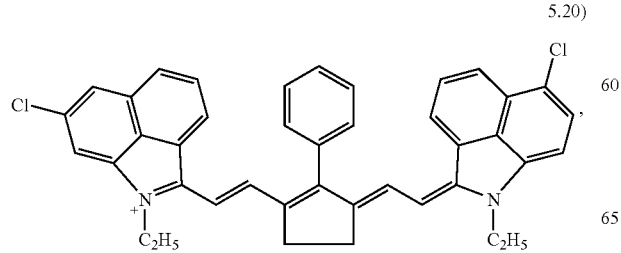
5.21)
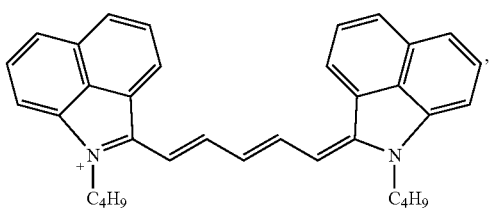
5.22)
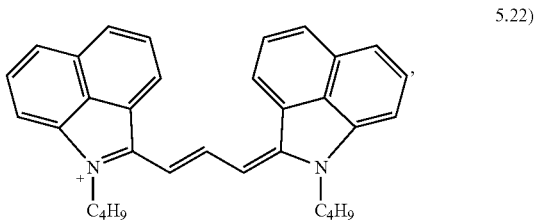
5.23)
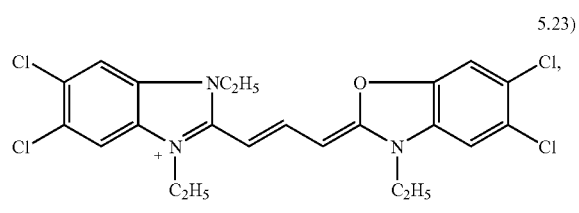
5.24)
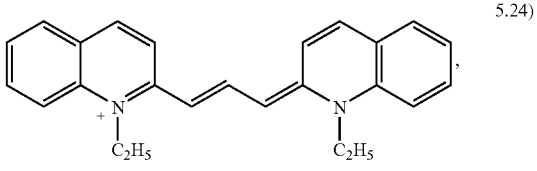
5.25)
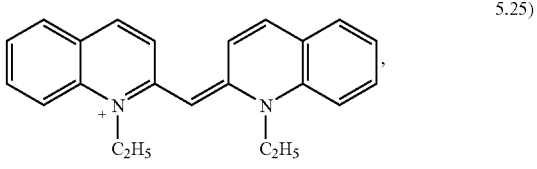
5.26)
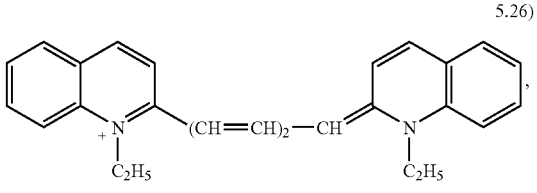
5.27)
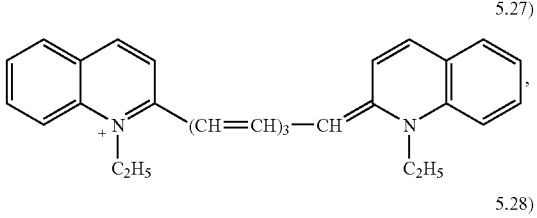
5.28)
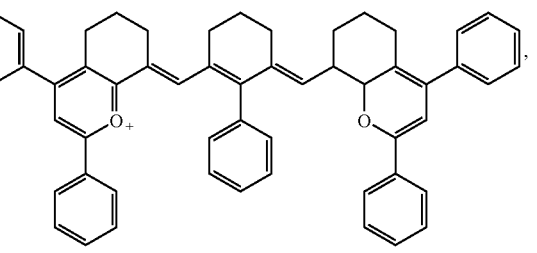

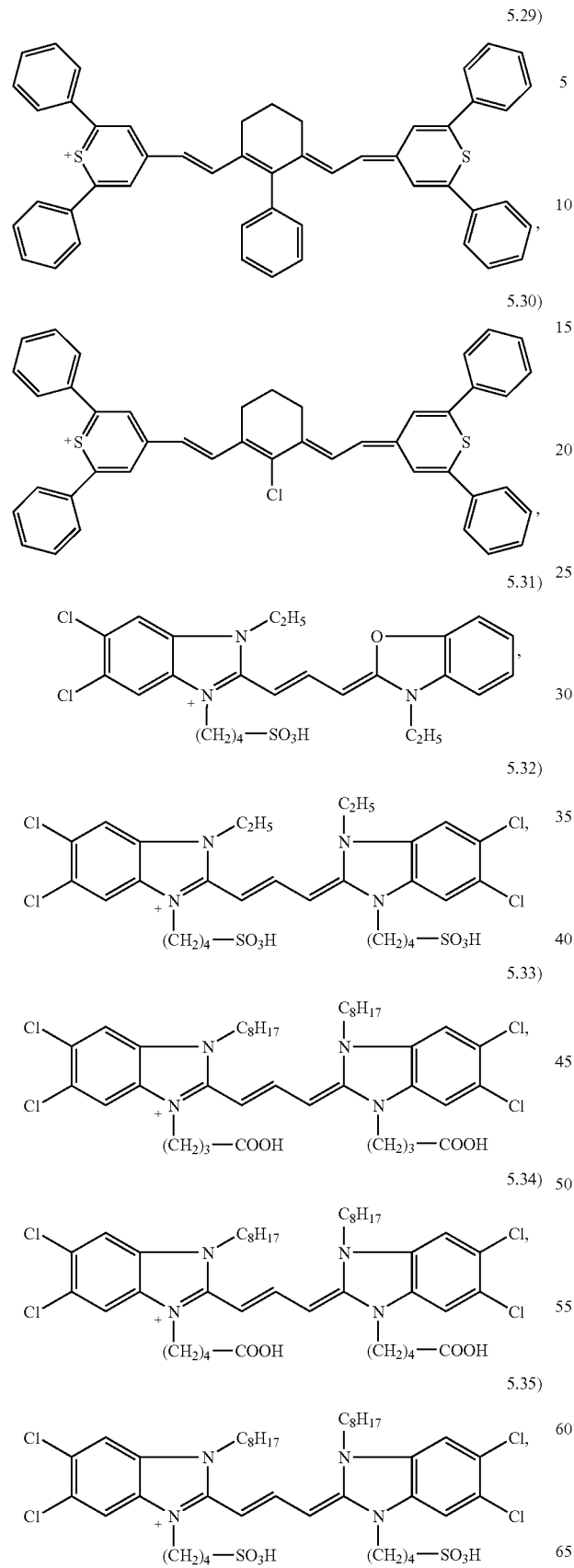
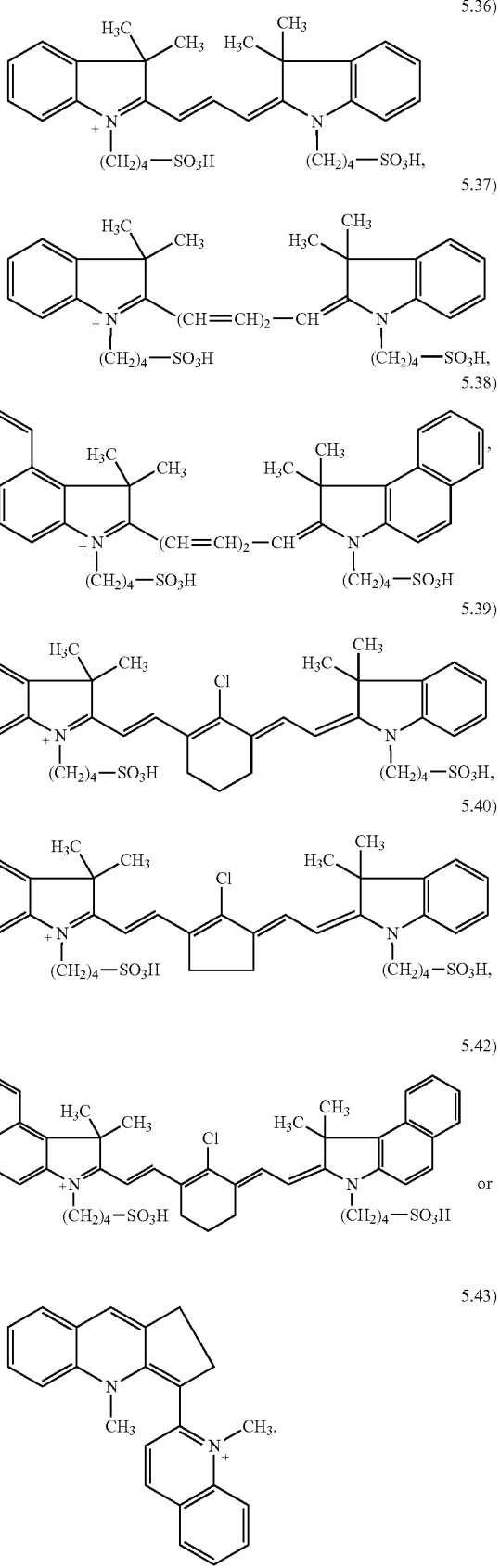

Preferred cations of azacarbocyanine dyes can be described by the formula V-3

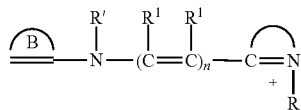
V-3 where n denotes 1 or 2,

R' denotes hydrogen or alkyl,

R denotes alkyl, alkenyl, cycloalkyl, aryl or heteroaryl and $R^1$ in each case, independently of one another, denotes H, Cl, Br, I, alkyl, partially or fully chlorinated alkyl, alkenyl, cycloalkyl, aryl, heteroaryl, Oalkyl, Oaryl, Salkyl, Saryl, NHalkyl, N(alkyl)$_2$, C(O)H, C(O)alkyl, C(O)aryl, CN, N=N-aryl, P(aryl)$_2$, NHCOalkyl or NHCOaryl.

The respective radicals R and/or $R^1$ may each be bonded to one another or to a substituent of the ring system by means of single or double bonds.

The ring system, represented by

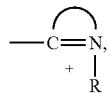

denotes a nitrogen-containing unsaturated mono-, bi- or tricyclic heterocycle having 5 to 13 ring members, which may contain 1, 2 or 3 N and/or 1 or 2 S or O atoms and in which the heterocyclic radical may be mono- or polysubstituted by Z as described above.

The ring system preferably denotes pyridine, quinoline, α-pyran, γ-thiopyran, thiazole, pyrrole, imidazole or oxazole, which may furthermore be fused to a phenyl. The ring closure may exist not only between nitrogen and the adjacent carbon, but also between nitrogen and the following carbon atoms in the chain or the $R^1$ radicals if these contain carbon, or between carbon atoms with formation of aromatic systems.

A particularly preferred ring system is 3,3-dimethyl-3H-indole. The ring system, represented by

denotes an unsaturated mono- or bicyclic carbocycle having 5 to 14 ring members or an unsaturated mono-, bi- or tricyclic heterocycle having 5 to 13 ring members, which may contain 1, 2 or 3 N and/or 1 or 2 S or O atoms and in which the carbo- or heterocyclic radical may be mono- or polysubstituted by Z as described above.

The ring system preferably denotes aryl.

n is preferably 1.

$R^1$ in formula V-3 is preferably H or alkyl.

R in formula V-3 is preferably alkyl.

Particularly preferred cations CAT$^+$ from the group of the azacarbocyanine dyes are:

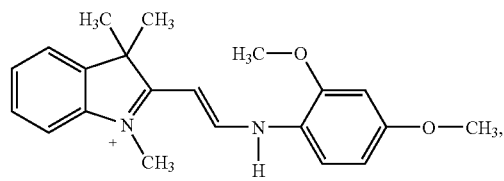
5.44)

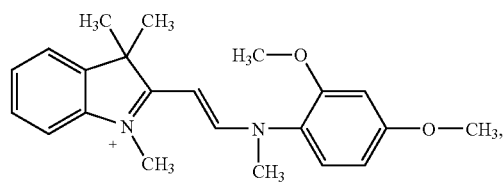
5.45)

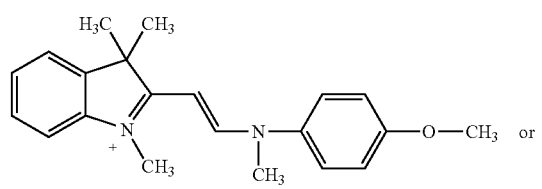
5.46) or

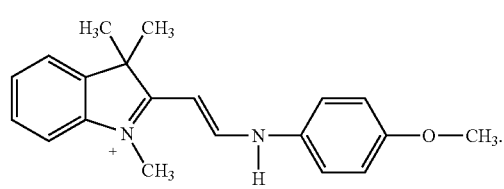
5.47)

Preferred cations of diazacarbocyanine dyes can be described by the formula V-4

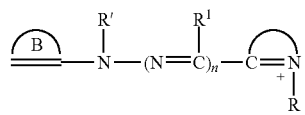
V-4 where n denotes 1,

R' denotes hydrogen or alkyl,

R denotes alkyl, alkenyl, cycloalkyl, aryl or heteroaryl and $R^1$ in each case, independently of one another, denotes H, Cl, Br, I, alkyl, partially or fully chlorinated alkyl, alkenyl, cycloalkyl, aryl, heteroaryl, Oalkyl, Oaryl, Salkyl, Saryl, NHalkyl, N(alkyl)$_2$, C(O)H, C(O)alkyl, C(O)aryl, CN, N=N-aryl, P(aryl)$_2$, NHCOalkyl or NHCOaryl.

The respective radicals R and/or $R^1$ may each be bonded to one another or to a substituent of the ring system by means of single or double bonds. The ring system, represented by

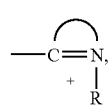

denotes a nitrogen-containing unsaturated mono-, bi- or tricyclic heterocycle having 5 to 13 ring members, which may contain 1, 2 or 3 N and/or 1 or 2 S or O atoms and in which the heterocyclic radical may be mono- or polysubstituted by Z as described above.

The ring system preferably denotes pyridine, quinoline, α-pyran, γ-thiopyran, thiazole, pyrrole, imidazole or oxazole, which may furthermore be fused to a phenyl. The ring closure may exist not only between nitrogen and the adjacent carbon, but also between nitrogen and the following carbon atoms in the chain or the $R^1$ radicals if these contain carbon, or between carbon atoms with formation of aromatic systems.

A particularly preferred ring system is 3,3-dimethyl-3H-indole.

The ring system, represented by

denotes an unsaturated mono- or bicyclic carbocycle having 5 to 14 ring members, which may be mono- or polysubstituted by Z as described above, preferably aryl.

$R^1$ in formula V-4 is preferably H or alkyl.

R in formula V-4 is preferably alkyl.

Particularly preferred cations CAT$^+$ from the group of the diazacarbocyanine dyes are:

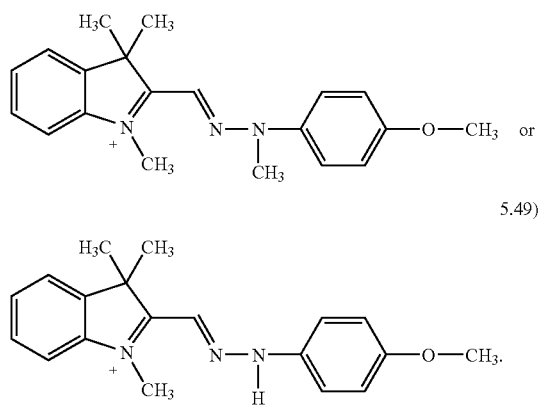

Preferred cations of triazacarbocyanine dyes can be described by the formula V-5

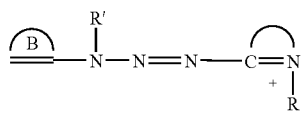

where

R' denotes hydrogen or alkyl and

R denotes alkyl, alkenyl, cycloalkyl, aryl or heteroaryl.

The respective radicals R and/or R' may each be bonded to a substituent of the ring system by means of single or double bonds.

The ring system, represented by

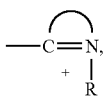

denotes a nitrogen-containing unsaturated mono-, bi- or tri-cyclic hetero-cycle having 5 to 13 ring members, which may contain 1, 2 or 3 N and/or 1 or 2 S or O atoms and in which the heterocyclic radical may be mono- or polysubstituted by Z as described above.

The ring system preferably denotes pyridine, quinoline, α-pyran, γ-thiopyran, thiazole, pyrrole, imidazole or oxazole, which may furthermore be fused to a phenyl. The ring closure may exist not only between nitrogen and the adjacent carbon, but also between nitrogen and the following carbon atoms in the chain or the $R^1$ radicals if these contain carbon, or between carbon atoms with formation of aromatic systems. A particularly preferred ring system is benzothiazole.

The ring system, represented by

denotes an unsaturated mono- or bicyclic carbocycle having 5 to 14 ring members, which may be mono- or polysubstituted by Z as described above, preferably aryl.

R in formula V-5 is preferably alkyl.

A particularly preferred cation CAT$^+$ from the group of the triazacarbocyanine dyes is:

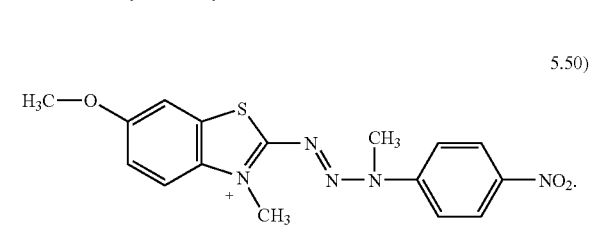

Preferred cations of hemicyanine dyes can be described by the formula V-6

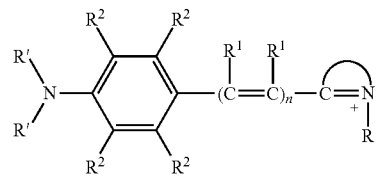

where n denotes 1, 2, 3, 4 or 5,

R' in each case, independently of one another, denotes H or alkyl,

R denotes alkyl, alkenyl, cycloalkyl, aryl or heteroaryl, $R^2$ in each case, independently of one another, denotes H, alkyl, $NO_2$, $NH_2$, NHalkyl or N(alkyl)$_2$ and $R^1$ in each case, independently of one another, denotes H, Cl, Br, I, alkyl, partially or fully chlorinated alkyl, alkenyl, cycloalkyl, aryl, heteroaryl, Oalkyl, Oaryl, Salkyl, Saryl, NHalkyl, N(alkyl)$_2$, C(O)H, C(O)alkyl, C(O)aryl, CN, N=N-aryl, P(aryl)$_2$, NHCOalkyl or NHCOaryl.

The respective radicals R, $R^1$ and/or $R^2$ may each be bonded to one another or to a substituent of the ring system by means of single or double bonds. For the excerpt of the formula $$-(\underset{\underset{R^1}{|}}{C}=\underset{\underset{R^1}{|}}{C})_n-$$

with n=2, this means that a cyclohexene may be present in the compound, such as, for example, where the cyclohexene may optionally be further substituted by Z as described above.

The ring system, represented by $$-C=\overset{+}{\underset{R,}{N}}$$

denotes an unsaturated mono-, bi- or tricyclic heterocycle having 5 to 13 ring members, which may contain 1, 2 or 3 N and/or 1 or 2 S or O atoms and in which the heterocyclic radical may be mono- or polysubstituted by Z as described above.

The ring system preferably denotes pyridine, quinoline, thiazole, pyrrole, imidazole or oxazole, which may furthermore be fused to a phenyl. The ring closure may exist not only between nitrogen and the adjacent carbon, but also between nitrogen and the following carbon atoms in the chain or the $R^1$ radicals if these contain carbon, or between carbon atoms with formation of aromatic systems.

Particularly preferred ring systems are 3,3-dimethyl-3H-indole, benzothiazole, benzoxazole, pyridine or quinoline, which may optionally be further substituted by Z. Z here is particularly preferably alkyl.

n is preferably 1, 2 or 3.

$R^1$ in formula V-6 is preferably hydrogen.

$R^2$ is preferably hydrogen or alkyl.

R in formula V-6 is preferably alkyl.

Particularly preferred cations CAT$^+$ from the group of the hemicyanine dyes are:

5.51)

5.52)

5.53)

5.54)

5.55)

5.56)

5.57)

5.58)

Preferred cations of diazahemicyanine dyes can be described by the formula V-7

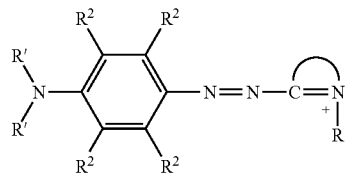

where

R' in each case, independently of one another, denotes H or alkyl,

R in each case, independently of one another, denotes alkyl, alkenyl, cycloalkyl, aryl or heteroaryl and $R^2$ in each case, independently of one another, denotes H, alkyl, $NO_2$, $NH_2$, NHalkyl or N(alkyl)$_2$.

The respective radicals R, $R^1$ and/or $R^2$ may each be bonded to one another or to a substituent of the ring system by means of single or double bonds.

The ring system, represented by

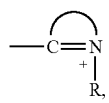

denotes an unsaturated mono-, bi- or tricyclic heterocycle having 5 to 13 ring members, which may contain 1, 2 or 3 N and/or 1 or 2 S or O atoms and in which the heterocyclic radical may be mono- or polysubstituted by Z as described above.

The ring system preferably denotes pyridine, quinoline, thiazole, pyrrole, imidazole or oxazole, which may furthermore be fused to a phenyl. The ring closure may exist not only between nitrogen and the adjacent carbon, but also between nitrogen and the following carbon atoms in the chain or the $R^1$ radicals if these contain carbon, or between carbon atoms with formation of aromatic systems.

Particularly preferred ring systems are thiazole, benzothiazole, imidazole, pyridine, indazole or 1,2,4-triazole, which may optionally be further substituted by Z. Z here is particularly preferably alkyl.

$R^2$ is preferably hydrogen.

R in formula V-7 is in each case, independently, preferably alkyl or CONH$_2$-substituted alkyl.

Particularly preferred cations CAT$^+$ from the group of the diazahemicyanine dyes are:

5.59)

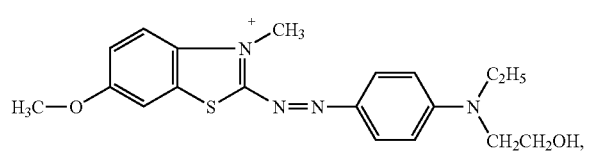

5.60)

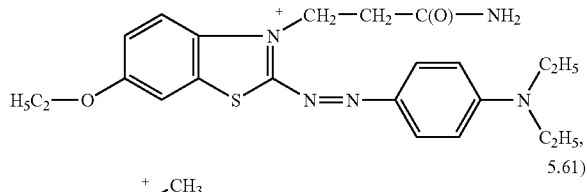

5.61)

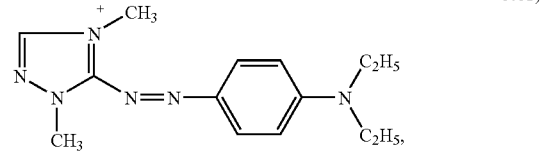

5.62)

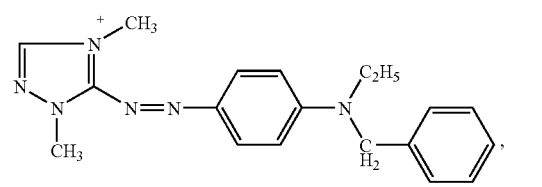

5.63)

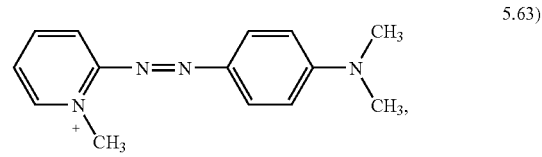

5.64)

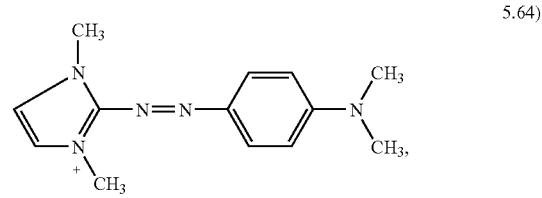

5.65)

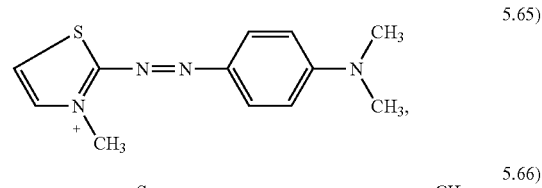

5.66)

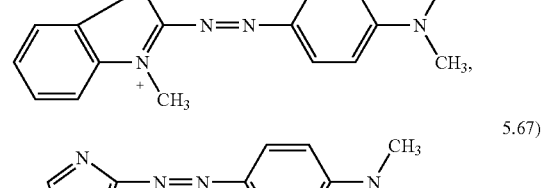

5.67)

or 5.68)

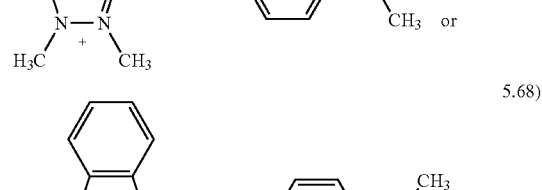

Preference is given in accordance with the invention to a group of compounds of the formula I where Y$^-$ in each case has one of the meanings indicated or preferably described in the case of formula I and in which CAT⁺ is a cation of a styryl dye.

Preferred cations can be described by the formula VI $$A^+ - (\underset{R}{\overset{R}{C}} = \underset{}{\overset{}{C}})_n - B \quad \text{VI}$$

in which A⁺ is a positively charged heterocyclic radical, as defined above in the case of heteroaryl, which may be partially saturated, and B denotes a carbo- or heterocyclic radical, where in each case one or more double bonds are present, n denotes 1, 2 or 3 and R in each case, independently of one another, denotes H, F, Cl, Br or alkyl, where adjacent R may optionally form an unsaturated mono- or bicyclic radical.

For the excerpt of the formula $$-(\underset{R}{\overset{R}{C}} = \underset{}{\overset{}{C}})_n-$$

with n=2, this means that a cyclopentene may be present in the compound, such as, for example,

[cyclopentene structure with R substituents]

where the cyclopentene may optionally be further substituted by Z as described above.

Hemicyanine dyes as defined above are excluded.

R preferably denotes H.

Preferred cations CAT⁺ from the group of the styryl dyes are:

6.1) [structure]

6.2) [structure]

6.3) [structure]

6.4) [structure]

6.5) [structure]

6.6) [structure]

6.7) [structure]

Preference is given in accordance with the invention to a group of compounds of the formula I where Y⁻ in each case has one of the meanings indicated or preferably described in the case of formula I and in which CAT⁺ is a cation of a cationic azo dye.

Preferred cations can be described by the formula VII $$R'-N=N-R'' \quad \text{VII,}$$

in which R' and R" are each, independently of one another, aryl or heteroaryl as defined above, and one of the two aromatic nuclei is positively charged.

If the dye molecule contains 2 azo groups a bisazo dye is formed, in the case of 3 azo groups a triazo dye is formed.

Diazahemicyanine dyes are excluded here.

R' is particularly preferably $N_2^+$-substituted phenyl, where the phenyl ring may be further substituted by alkyl or Oalkyl, or is thiazolyl or phenazinyl.

R is particularly preferably aryl or thienyl.

Particularly preferred cations CAT⁺ from the group of the azo dyes are:

7.1)
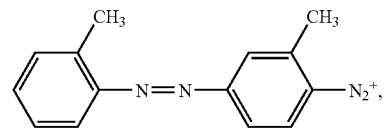

7.2)
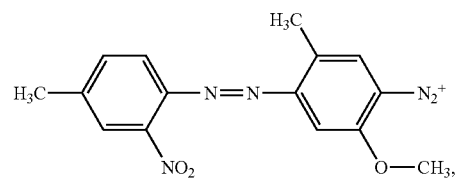

7.3)
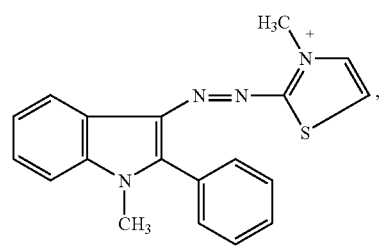

7.4)
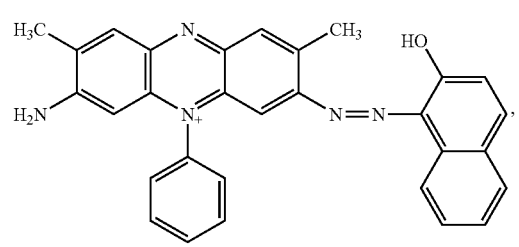

7.5)
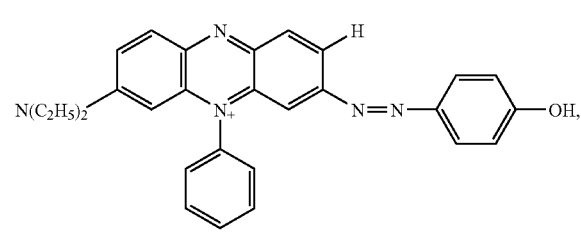

7.6)
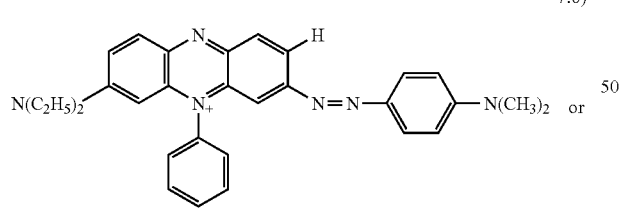

7.7)
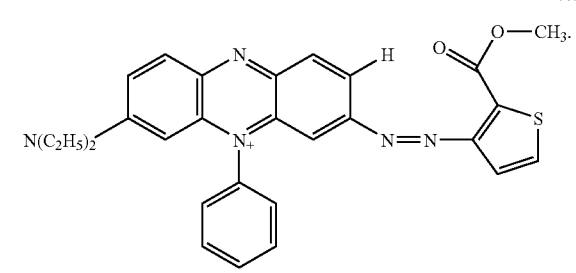

Preference is given in accordance with the invention to a group of compounds of the formula I where $Y^-$ in each case has one of the meanings indicated or preferably described in the case of formula I and in which CAT⁺ is a cation of a tetrazolium dye.

Preferred cations can be described by the formula VIII

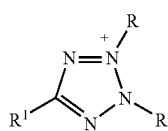

VIII

R in each case, independently of one another, denotes aryl or heteroaryl and $R^1$ denotes hydrogen, alkyl, cycloalkyl, aryl, heteroaryl, alkylaryl, alkenyl, cycloalkenyl, OH, SH, Oalkyl, Salkyl, $SO_2$-alkyl, $SO_2$-aryl, COOH, COalkyl, COOaryl, C(O)-aryl, C(O)-alkyl, C(O)-heteroaryl, C(O)NHalkyl, C(O)NHaryl, C(O)N(alkyl)(aryl), C(O)N(alkyl)$_2$, NH$_2$, NHalkyl, N(alkyl)$_2$, NHaryl, N=NOH, N=NOalkyl, N=N-aryl, NHCOalkyl, NHCOaryl, NHSO$_2$alkyl, NHSO$_2$aryl, CN, F, Cl or Br.

$R^1$ is particularly preferably phenyl and R is in each case, independently of one another, aryl or heteroaryl.

Adjacent substituents R or $R^1$ may be bonded to one another by single or double bonds.

Particularly preferred cations CAT⁺ from the group of the tetrazolium dyes are:

8.1)
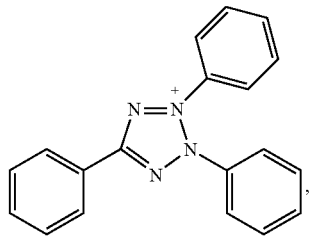

8.2)
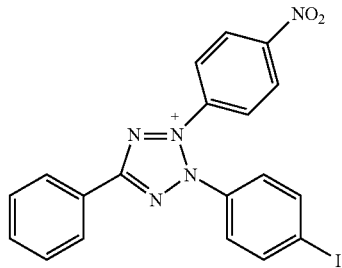

8.3)
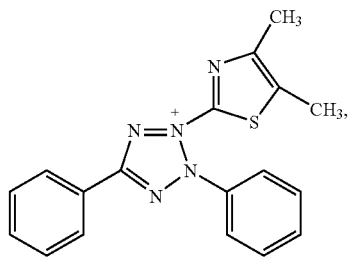

8.4)

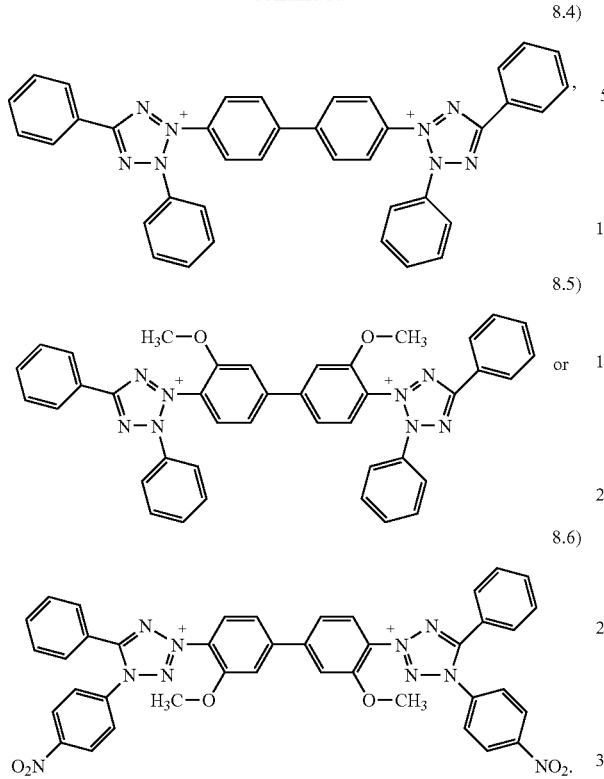

8.5)

8.6)

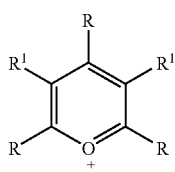

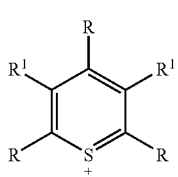

Preference is given in accordance with the invention to a group of compounds of the formula I where $Y^-$ in each case has one of the meanings indicated or preferably described in the case of formula I and in which $CAT^+$ is a cation of a pyrylium dye.

Preferred pyrylium cations can be described by the formula IX

IX in which

R in each case, independently of one another, denotes H, alkyl, cycloalkyl, aryl, heteroaryl, OH, Oalkyl, $NH_2$, NHalkyl, $N(alkyl)_2$, COOH, COalkyl, Cl or Br and $R^1$ in each case, independently of one another, denotes H, alkyl, cycloalkyl, aryl, heteroaryl, alkylaryl, alkenyl, OH, Oalkyl, COOalkyl, COOaryl, OC(O)aryl, OC(O)-alkyl, C(O)—H, $CONH_2$, C(O)NHalkyl, C(O)NHaryl, C(O)aryl, C(O)alkyl, NHalkyl, $N(alkyl)_2$, NHCOalkyl, $NHCOCF_3$, NHCOaryl, NHCOOalkyl, $NO_2$, Cl or Br.

R is particularly preferably phenyl.

Adjacent substituents R or $R^1$ may be bonded to one another by single or double bonds.

A preferred group of cations of the formula IX are cations in which R and $R^1$ form a fused phenyl ring, so-called benzopyrylium salts of the formula X

X in which,

R denotes hydrogen, alkyl, cycloalkyl, aryl, heteroaryl, OH, Oalkyl, $NH_2$, NHalkyl, $N(alkyl)_2$, COOH, COalkyl, Cl or Br, $R^1$ in each case, independently of one another, denotes H, alkyl, cycloalkyl, aryl, heteroaryl, OH, Oalkyl, NHalkyl, $N(alkyl)_2$, NHCOaryl, NHCOOalkyl, Cl or Br, $R^2$ denotes hydrogen, alkyl, $CH_2$—Cl, cycloalkyl, aryl, alkylaryl, heteroaryl, alkenyl, cycloalkenyl, alkynyl, OH, Oalkyl, Salkyl, COOalkyl, COOaryl, C(O)H, C(O)aryl, C(O)alkyl, C(O)alkenyl, $NH_2$, NHalkyl, $N(alkyl)_2$, NHaryl, Cl or Br, $R^3$ denotes hydrogen, alkyl, cycloalkyl, aryl, alkenyl, OH, Oalkyl, C(O)alkyl, C(O)alkenyl, CN, C(O)aryl, OC(O)alkyl, OC(O)aryl, NHCOalkyl, $NHCOCF_3$, $NO_2$, F, Cl, Br or I, $R^4$ denotes hydrogen, alkyl, cycloalkyl, cycloalkenyl, alkenyl, aryl, OH, Oalkyl, $NH_2$, NHalkyl, $N(alkyl)_2$, NHaryl, OC(O)alkyl, OC(O)aryl, CN, $NO_2$, Cl, Br or I and $R^5$ denotes hydrogen, alkyl, cycloalkyl, aryl, alkylaryl, NHCOalkyl, $NHCOCF_3$, OH, Oalkyl, CN, $NO_2$, Cl or Br.

In formula X, R is particularly preferably aryl, $R^2$ is particularly preferably alkyl and $R^1$, $R^3$ to $R^5$ is particularly preferably H.

Adjacent substituents R, $R^1$, $R^2$, $R^3$, $R^4$ or $R^5$ may be bonded to one another by means of single or double bonds.

Preference is given in accordance with the invention to a group of compounds of the formula I where $Y^-$ in each case has one of the meanings indicated or preferably described in the case of formula I and in which $CAT^+$ is a cation of a thiopyrylium dye.

Preferred thiopyrylium cations can be described by the formula XI

XI in which

R in each case, independently of one another, denotes H, alkyl, cycloalkyl, aryl, alkylaryl, alkenyl, alkynyl, heteroaryl, OH, Oalkyl, Salkyl, Sealkyl, $NH_2$, NHalkyl, $N(alkyl)_2$, NHaryl, N(alkyl)(aryl), $N(aryl)_2$, C(O)alkyl, C(O)aryl, COOH, COOalkyl, $CONH_2$, CONHalkyl, $CON(alkyl)_2$, CN, Cl or Br and $R^1$ in each case, independently of one another, denotes H, alkyl, cycloalkyl, aryl, heteroaryl, alkylaryl, alkenyl, OH, Oalkyl, Salkyl, COOH, COalkyl, COOaryl, OC(O)-aryl, OC(O)-alkyl, $CONH_2$, CONHalkyl, CONHaryl, C(S)alkyl, C(O)aryl, C(O)alkyl, $NH_2$, NHalkyl, $N(alkyl)_2$, NHaryl, CN, Cl, Br or I.

R is particularly preferably in each case, independently of one another, phenyl or hydrogen and R¹ is hydrogen.

Adjacent substituents R or R¹ may be bonded to one another by single or double bonds.

A preferred group of cations of the formula XI are cations in which R and R¹ form a fused phenyl ring, so-called benzothiopyrylium salts of the formula XII

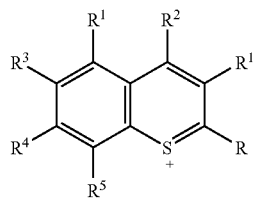

XII in which,

R denotes hydrogen, alkyl, cycloalkyl, aryl, alkenyl, Oalkyl, Salkyl, NH₂, NHalkyl, NHheteroaryl, N(alkyl)₂, COOH, COOalkyl, Cl, Br or I, R¹ in each case, independently of one another, denotes H, alkyl, cycloalkyl, alkenyl, OH, Oalkyl, Salkyl, NHalkyl, N(alkyl)₂, Cl or Br, R² denotes hydrogen, alkyl, CH₂—Cl, cycloalkyl, aryl, alkylaryl, heteroaryl, alkenyl, cycloalkenyl, OH, Oalkyl, Salkyl, COOH, COOalkyl, COOaryl, OC(O)alkyl, NH₂, NHalkyl, N(alkyl)₂, NHaryl, CN, F, Cl or Br, R³ denotes hydrogen, alkyl, cycloalkyl, OH, Oalkyl, CN, NO₂, F, Cl, Br or I, R⁴ denotes hydrogen, alkyl, cycloalkyl, Oalkyl, NH₂, NHalkyl, N(alkyl)₂, CN, F, Cl, Br or I and R⁵ denotes hydrogen, alkyl, cycloalkyl, OH, Oalkyl, CN, F, Cl or Br.

Adjacent substituents R, R¹, R², R³, R⁴ or R⁵ may be bonded to one another by means of single or double bonds.

In formula XIII, R is particularly preferably aryl.

Particularly preferred cations CAT⁺ from the group of the pyrylium benzopyrylium and thiopyrylium dyes are:

9.1)

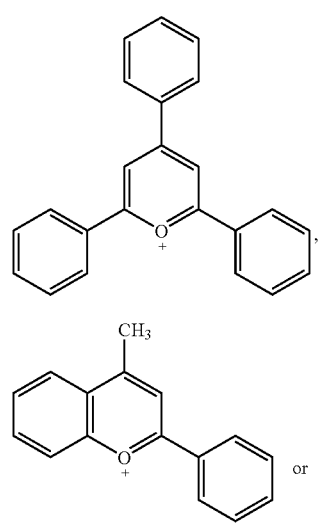

or 10.1)

11.1)

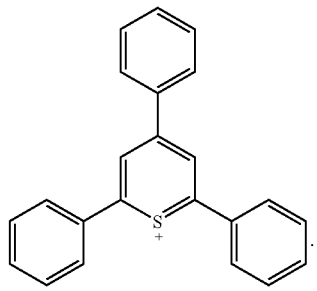

Preference is given in accordance with the invention to a group of compounds of the formula I where Y⁻ in each case has one of the meanings indicated or preferably described in the case of formula I and in which CAT⁺ is a cation of a thiazine dye.

Preferred cations can be described by the formula XIII

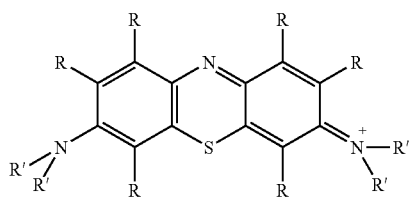

XIII where

R in each case, independently of one another, denotes H, alkyl, Oalkyl or NO₂, and R' in each case, independently of one another, denotes H, alkyl, alkyl which is partially substituted by hydroxyl, alkyl which is partially substituted by Br or COOH, or C(O)alkyl, COOH or COalkyl.

R is particularly preferably H or alkyl. R' is particularly preferably H or alkyl.

Particularly preferred cations CAT⁺ from the group of the thiazine dyes are:

13.1)

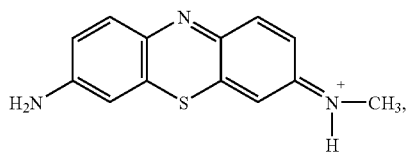

13.2)

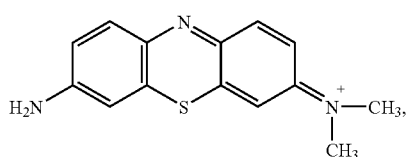

13.3)

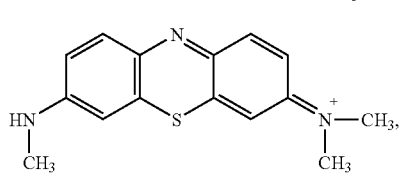

-continued

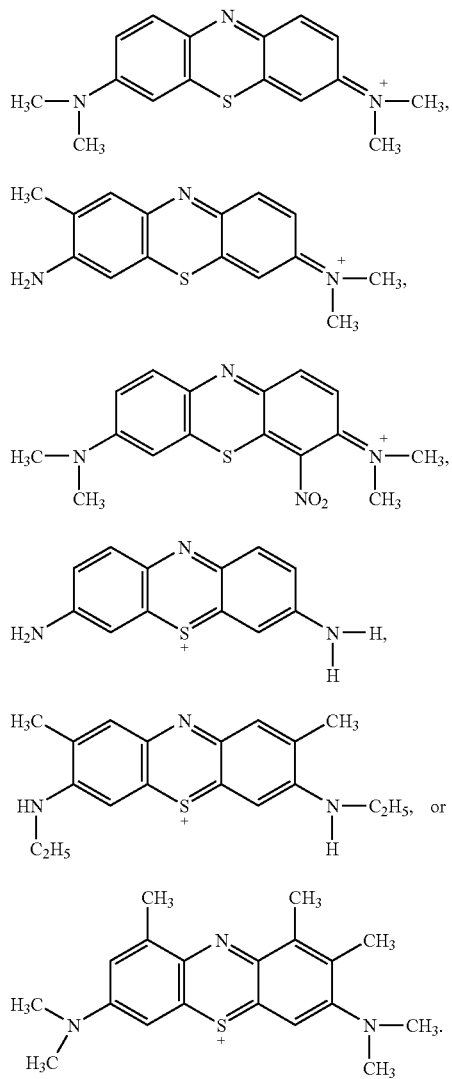

Preference is given in accordance with the invention to a group of compounds of the formula I where Y⁻ in each case has one of the meanings indicated or preferably described in the case of formula I and in which CAT⁺ is a cation of an oxazine dye.

Preferred cations can be described by the formula XIV

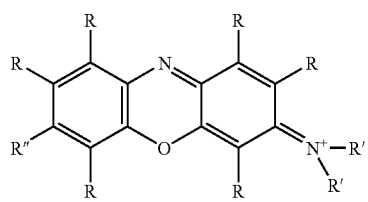

in which
R in each case, independently of one another, denotes H, alkyl, alkenyl, OH, Oalkyl, COOH, COOalkyl, CONH$_2$, CONHalkyl, CON(alkyl)$_2$, NH$_2$, NHalkyl or N(alkyl)$_2$, R' in each case, independently of one another, denotes H, alkyl or alkyl which is partially substituted by CONH$_2$, CONHalkyl, C(O)N(alkyl)$_2$, COOH or COOheteroaryl and R" denotes hydrogen, alkyl, NH$_2$, NHalkyl, N(alkyl)$_2$, NHaryl, NHheteroaryl, Saryl, SO$_2$-aryl, S—C(O)-alkyl, SC(N)NH$_2$, or alkyl which is partially substituted by CONH$_2$, CONHalkyl, CON(alkyl)$_2$, COOH or COOheteroaryl.

R is particularly preferably H, alkyl, OH or COOH, where adjacent substituents R may also together form a fused phenyl ring. R' is particularly preferably H or alkyl. R" is preferably H, NH$_2$, NHalkyl, N(alkyl)$_2$ or OH.

Particularly preferred cations CAT⁺ from the group of the oxazine dyes are:

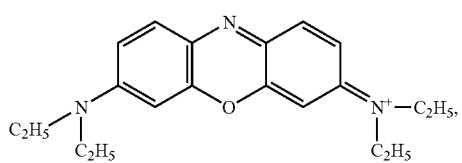

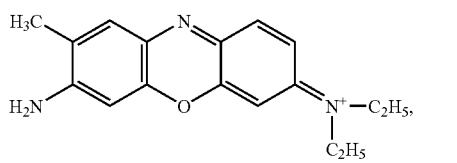

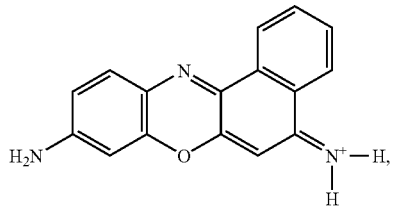

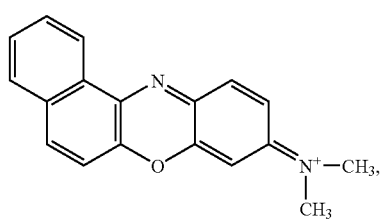

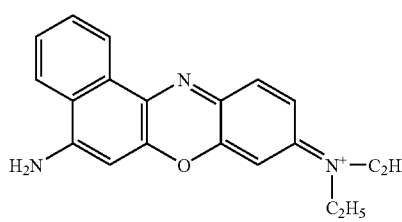

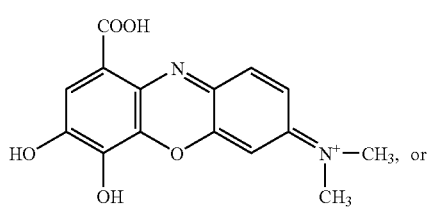

14.7)

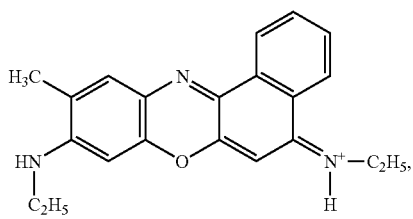

Preference is given in accordance with the invention to a group of compounds of the formula I where Y⁻ in each case has one of the meanings indicated or preferably described in the case of formula I and in which CAT⁺ is a cation of a triarylmethane dye.

Preferred cations can be described by the formula XV

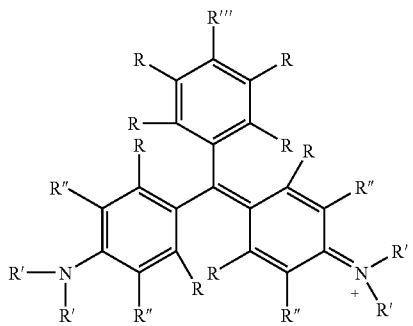

in which
R in each case, independently of one another, denotes H, alkyl, COOH, Cl or F,
R' in each case, independently of one another, denotes H, alkyl, alkyl which is partially substituted by OH, or alkenyl, alkynyl, aryl or C(O)alkyl,
R" in each case, independently of one another, denotes H, alkyl, aryl, $NH_2$, NHalkyl, N(alkyl)$_2$, NHaryl, N(alkyl)(aryl), OH, Oalkyl, COOH, COOalkyl, $SO_2$-alkyl, CN, $NO_2$, F, Cl, Br or I and
R''' denotes hydrogen, alkyl, aryl, heteroaryl, $NH_2$, NHalkyl, N(alkyl)$_2$, NHaryl, N(alkyl)(aryl), OH, Oalkyl, COOH, COOalkyl, COO-heteroaryl, CONHalkyl, $SO_2$-alkyl, $SO_2H$, $SO_3H$, $SO_3$alkyl, CN, $NO_2$, F, Cl, Br, I, $N_3$ or NCS.

R is particularly preferably H or alkyl, where adjacent substituents R and R" may also together form a fused phenyl ring. R' is particularly preferably H or alkyl.

Particularly preferred cations CAT⁺ from the group of the triarylmethane dyes are:

15.1)

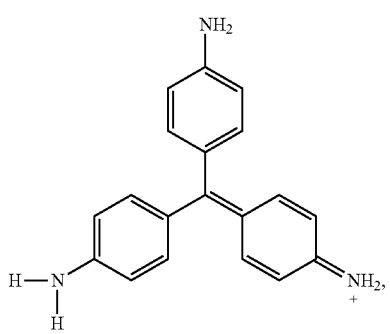

15.2)

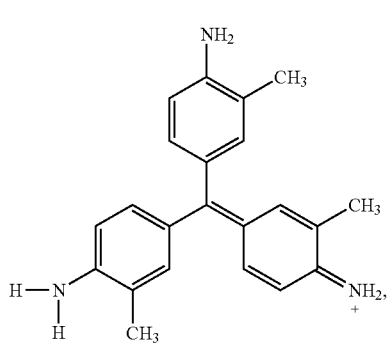

15.3)

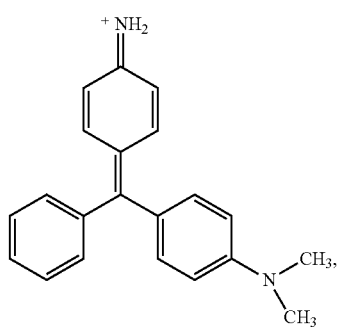

15.4)

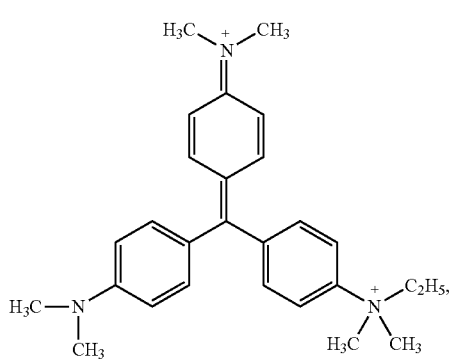

15.5)

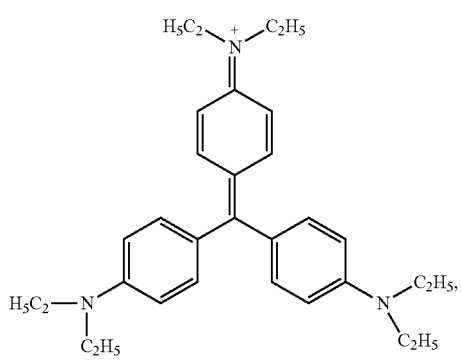

-continued

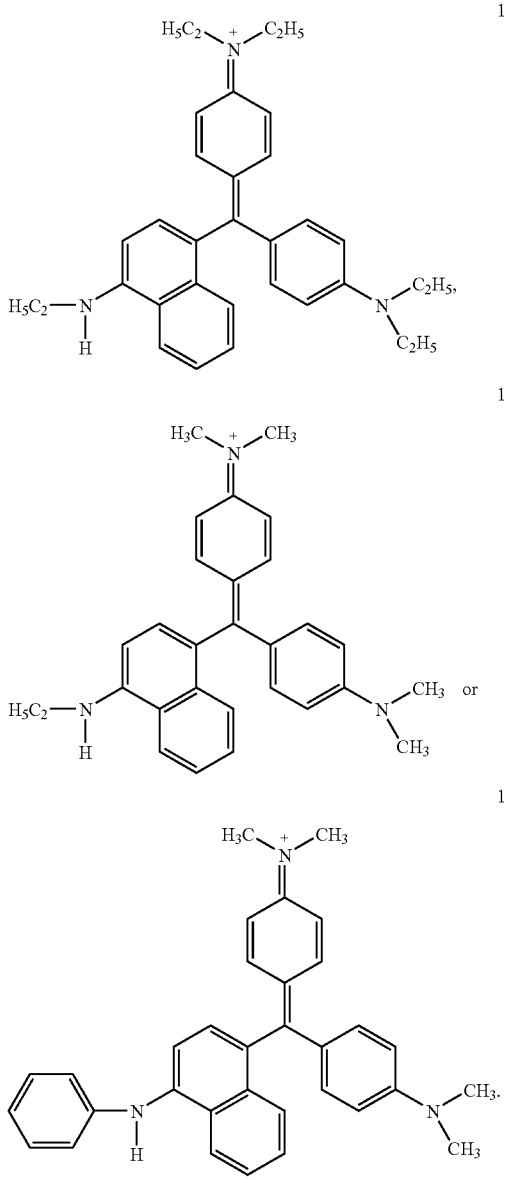

15.6)

15.7)

15.8)

Further preferred cations of triarylmethane dyes are

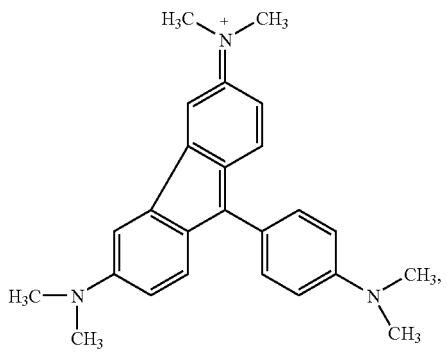

15.9)

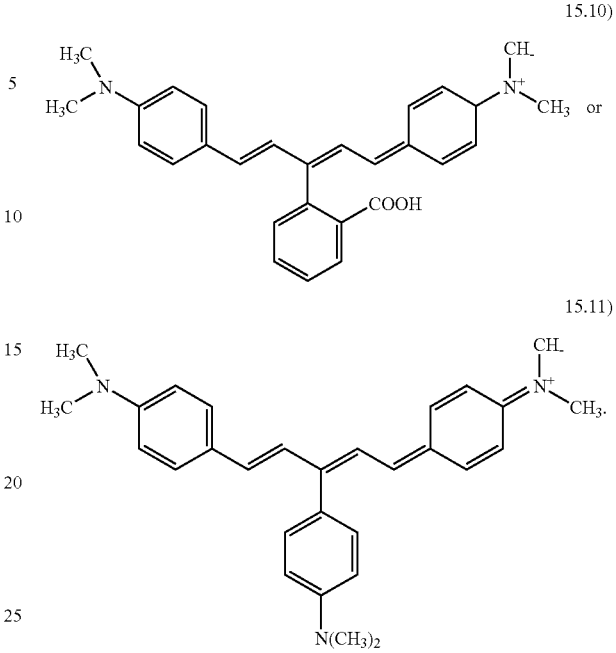

15.10)

15.11)

Preference is given in accordance with the invention to a group of compounds of the formula I where $Y^-$ in each case has one of the meanings indicated or preferably described in the case of formula I and in which $CAT^+$ is a cation of a diarylmethane dye.

Preferred cations can be described by the formula XVI

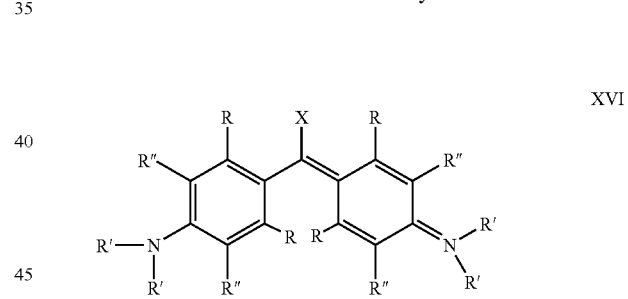

XVI in which

R in each case, independently of one another, denotes H, alkyl or COOH,

R' in each case, independently of one another, denotes H, alkyl, alkyl which is partially substituted by OH, or alkylaryl or aryl, R" in each case, independently of one another, denotes H, alkyl, aryl, $NH_2$, NHalkyl, $N(alkyl)_2$, NHaryl, N(alkyl)(aryl), OH, Oalkyl, COOH, CN, F, Cl or Br and X denotes hydrogen, alkyl, alkenyl, heteroaryl, Salkyl, OH, Oalkyl, CN, F, Cl or Br.

R is particularly preferably H. R' is particularly preferably alkyl. R" is particularly preferably H.

X is particularly preferably H or alkenyl, where the alkenyl chain may be the bonding element to a second diarylmethane dye.

Particularly preferred cations CAT⁺ from the group of the diarylmethane dyes are:

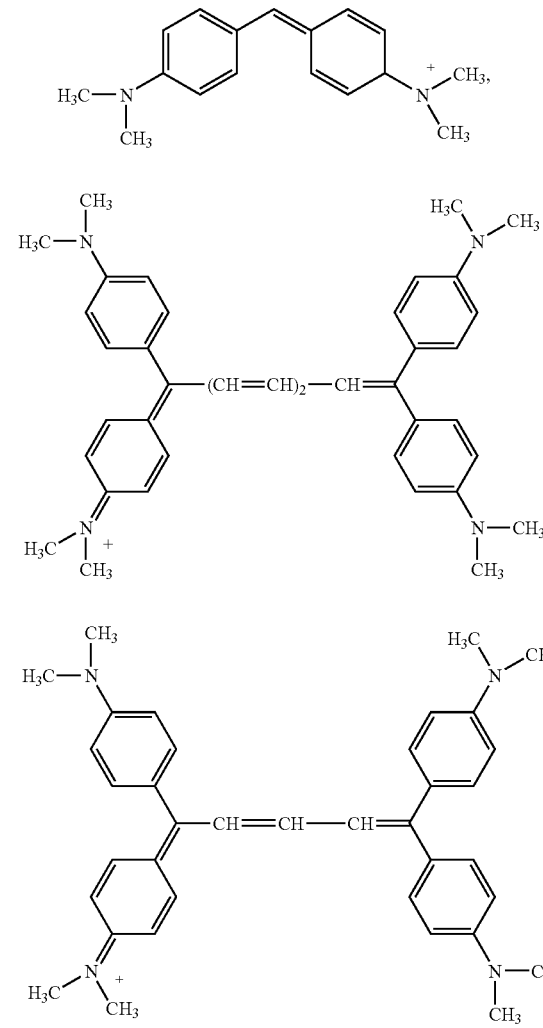

16.1)

16.2)

16.3)

Preference is given in accordance with the invention to a group of compounds of the formula I where Y⁻ in each case has one of the meanings indicated or preferably described in the case of formula I and in which CAT⁺ is a cation of an acridine dye.

Preferred cations can be described by the formula XVII

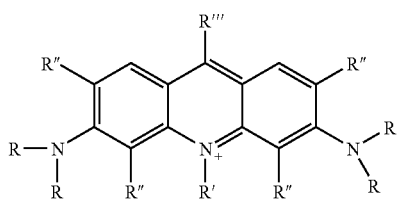

XVII in which

R in each case, independently of one another, denotes H, alkyl, alkylaryl, C(O)CH$_2$Cl or C(O)alkyl, NRR in formula XVII may also denote N=N-aryl, R' in each case, independently of one another, denotes H, alkyl, alkenyl, alkynyl, aryl, heteroaryl, alkylaryl, or alkyl which is partially substituted by COOH or CONHaryl, R" in each case, independently of one another, denotes H, alkyl, aryl, alkylaryl, NHCOalkyl or NHCOaryl and R'" denotes hydrogen, alkyl, alkylaryl, aryl, heteroaryl, Salkyl, or CN.

R is particularly preferably H or alkyl. R' is particularly preferably H or alkyl.

R" is particularly preferably H.

R'" is particularly preferably H.

Particularly preferred cations CAT⁺ from the group of the acridine dyes are:

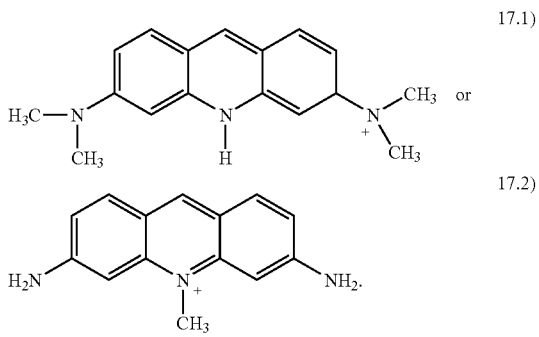

17.1)

17.2)

Preference is given in accordance with the invention to a group of compounds of the formula I where Y⁻ in each case has one of the meanings indicated or preferably described in the case of formula I and in which CAT⁺ is a cation of a quinoline dye.

Preferred cations can be described by the formula XVIII

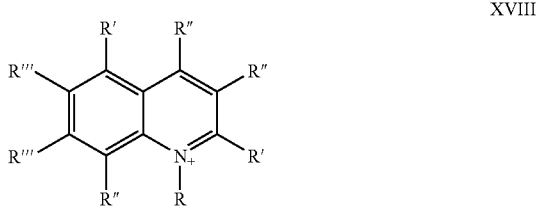

XVIII in which

R in each case, independently of one another, denotes alkyl, alkenyl, aryl, alkylaryl, CH$_2$COOH or CH$_2$COalkyl, R' in each case, independently of one another, denotes H, alkyl, alkenyl, alkenyl which is partially substituted by heteroaryl, or alkynyl, aryl, heteroaryl or alkylaryl, R" in each case, independently of one another, denotes H, alkyl, alkenyl, alkenyl which is partially substituted by heteroaryl, or aryl, alkylaryl, OH, Oalkyl, Salkyl, NH$_2$, NHalkyl, NHaryl, COOH, COalkyl, F, Cl, Br or I and R'" denotes hydrogen, alkyl, Oalkyl, CN or NO$_2$.

Adjacent substituents R, R', R" or R'" may be bonded to one another by means of a single or double bond.

Adjacent substituents R and R" in position 3 and 4 of the quinoline structure preferably form a phenyl ring, which may optionally be substituted by R, R' or R".

Particularly preferred cations CAT⁺ from the group of the quinoline dyes are:

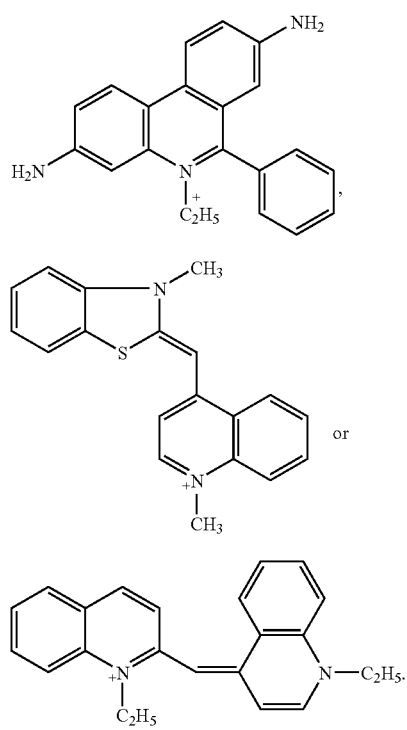

Particularly preferred cations CAT⁺ from the group of the isoquinoline dyes are:

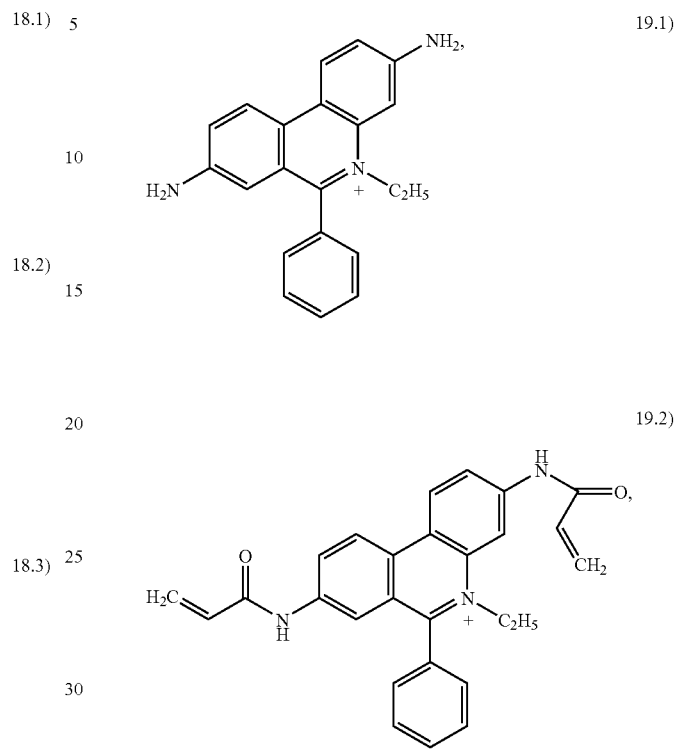

Preference is given in accordance with the invention to a group of compounds of the formula I where Y⁻ in each case has one of the meanings indicated or preferably described in the case of formula I and in which CAT⁺ is a cation of an isoquinoline dye.

Preferred cations can be described by the formula XIX

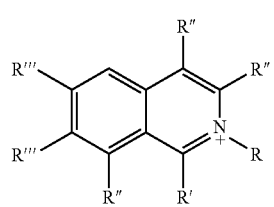

XIX in which
R in each case, independently of one another, denotes alkyl, alkenyl or CH₂COalkyl,
R' in each case, independently of one another, denotes H, alkyl, alkenyl, alkynyl, aryl, heteroaryl or alkylaryl,
R" in each case, independently of one another, denotes H, alkyl, alkenyl, Oalkyl, NH₂ or NHalkyl and
R''' denotes hydrogen, alkyl, Oalkyl, NH₂, NHCO-alkenyl, CN or NO₂.

Adjacent substituents R and R" in position 3 and 4 of the isoquinoline structure preferably form a phenyl ring, which may optionally be substituted by R, R' or R".

R preferably denotes alkyl. R' preferably denotes H or aryl. R" preferably denotes H or Oalkyl. R''' preferably denotes NH₂, Oalkyl or NHCO-alkenyl.

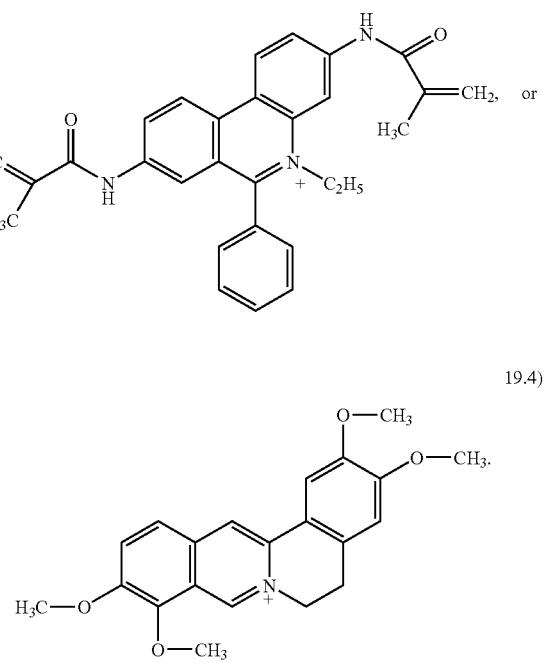

Preference is given in accordance with the invention to a group of compounds of the formula I where Y⁻ in each case has one of the meanings indicated or preferably described in the case of formula I and in which CAT⁺ is a cation of a quaternised azafluorenone dye.

Preferred cations can be described by the formula XX

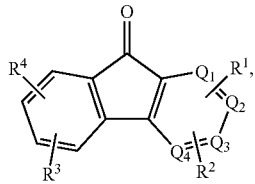
XX where
- $R^1$, $R^2$, $R^3$ and $R^4$ each, independently of one another, denote hydrogen, F, Cl, Br, alkyl, Oalkyl, hydroxyalkoxy having 1-4 C atoms, OH, $NO_2$, $NH_2$, NHalkyl, $Nalkyl_2$ or COalkyl, where two radicals may also, together, form a fused aromatic ring and
- $Q_1$, $Q_2$, $Q_3$ and $Q_4$ in total three carbon atoms and one quaternary nitrogen atom, which carries the radical $R^5$ with the meaning of alkyl, hydroxyalkyl having 1-4 C atoms, COalkyl, Salkyl, aryl, arylalkyl or heteroaryl, and which may also form an N-oxide.
- $R^1$-$R^4$ are preferably hydrogen. $R^5$ is preferably alkyl, arylalkyl or alkylaryl.

Particularly preferred cations $CAT^+$ from the group of the quaternary azafluorenone dyes are:

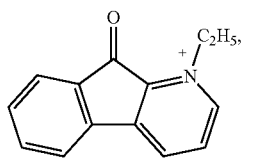
20a)

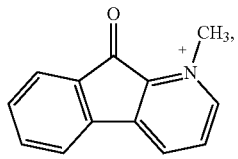
20b)

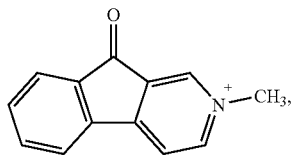
20c)

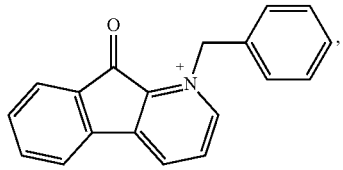
20d)

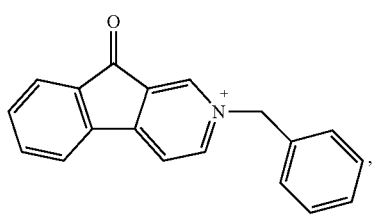
20e)

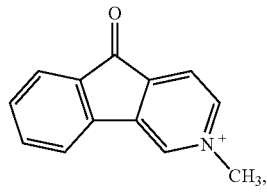
20f)

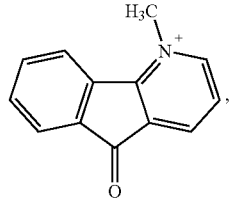
20g)

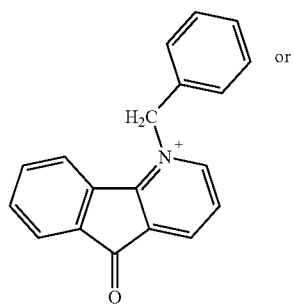
or 20h)

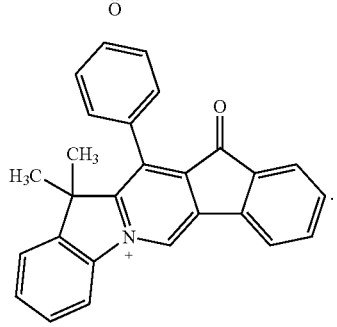
20i)

Preference is given in accordance with the invention to a group of compounds of the formula I where $CAT^+$ in each case has one of the meanings indicated or preferably described in the case of formula I or the formulae III to XX and in which $Y^-$ is a cyanoborate of the formula II-1 as described above.

Preference is given in accordance with the invention to a group of compounds of the formula I where $CAT^+$ in each case has one of the meanings indicated or preferably described in the case of formula I or the formulae III to XX and in which $Y^-$ is a fluoroalkylphosphate of the formula II-2 as described above.

Preference is given in accordance with the invention to a group of compounds of the formula I where $CAT^+$ in each case has one of the meanings indicated or preferably described in the case of formula I or the formulae III to XX and in which $Y^-$ is a fluoroalkylborate of the formula II-3, as described above, where 3,3'-diethoxyethyl-2,2'-thiadicarbocyanine trifluoromethyltrifluoroborate is excluded.

Preference is given in accordance with the invention to a group of compounds of the formula I where $CAT^+$ in each case has one of the meanings indicated or preferably described in the case of formula I or the formulae III to XX and in which $Y^-$ is an imide of the formula II-4 as described above.

Surprisingly, it has been found that the cationic dyes according to the invention are particularly stable. Their electrochemical, thermal and hydrolysis stability is significantly higher than the conventional cationic dyes having Cl⁻, tosylate or hexafluorophosphate anions.

Furthermore, the dyes according to the invention exhibit improved solubility in organic solvents. Conventional dyes, such as rhodamine B, Janus Green or Nile Blue, are, for example, insoluble in benzene. The cationic dyes according to the invention having a CAB anion, such as rhodamine CAB, Janus Green CAB or Nile Blue CAB, the cationic dyes having an FAP anion, such as safranine FAP or Nile Blue FAP, the cationic dyes having an FAB anion, such as safranine FAB or Nile Blue FAB, and the cationic dyes having an Im anion, such as rhodamine Im, Janus Green Im or Nile Blue Im, are, by contrast, soluble in benzene.

Conventional Nile Blue with hydrogensulfate as anion is insoluble in dimethyl carbonate, while, by contrast, the Nile Blue CAB, Nile Blue FAP, Nile Blue FAB or Nile Blue Im according to the invention is readily or very readily soluble.

The cationic dyes according to the invention can therefore be used in solvent-based systems.

Owing to the improved stability of the cationic dyes according to the invention, they are suitable for a multiplicity of applications. The invention thus also relates to the use of the cationic dyes according to the invention, optionally together with assistants, for colouring plastics, plastic fibres, wood, metals, textiles, furs, ceramic materials, glasses, films, in the agricultural sector, for example in the colouring of seed, for the preparation of flexographic printing inks, as ball-point pen pastes, as stamp ink and for colouring leather and paper, in cosmetic formulations, in the paints industry, in biochemistry, biology, medicine, analytics and electronics, in microscopy and histochemistry, for example for staining tissues and bacteria, as warning colour in the case of toxic substances, for example in propellants or detergents, as sensitisers in optical and electrophotography, in animal-care products, in chromatography materials, in paints and coatings, printing inks, in security printing, cosmetic formulations, contact lenses, in pharmaceuticals and for the preparation of colour compositions, such as, for example, pearlets and pastes, and of dry preparations, such as, for example, pellets, granules, chips, etc., which are preferably used in printing inks and paints. On use of the cationic dyes in paints and coatings, all areas of application known to the person skilled in the art are possible, such as, for example, powder coatings, automobile paints, printing inks for gravure, offset, screen or flexographic printing, and for coatings in indoor and outdoor applications. Specific fields of application are, in addition, in data acquisition systems, reprography, in ink microfilters, in photogalvanics, laser technology and the photo industry (High technology application of organic colorants, P. Gregory, Plenum Press, N.Y. 1991). For the cationic dyes according to the invention, there are also fields of application such as CD recorders (CD-R), DVD recorders (DVD+R, DVD+RW), Bluray disc (BD-ROM, BD-R, BD-RE), computer to plate (CTP), laser filters, laser marking and photopolymerisation.

In addition, the cationic dyes according to the invention can also advantageously be mixed with all known pigments and inorganic colorants.

The cationic dyes according to the invention can be supplied to the particular application with suitable additives known to the person skilled in the art. For colouring woven and knitted fabrics, use is made of dyes in suspensions with additives such as dyeing assistants (dye solvents, dispersants, fixing agents and reducing agents, wetting agents, dyeing accelerators, etc.), salts, alkalis or acids.

The present invention additionally relates to a process for the preparation of the cationic dyes according to the invention. In this process, compounds of the general formula XXI

CAT⁺A⁻       (XXI)

where CAT⁺ has the meaning indicated in the case of formula I or conforms to one of formulae III to XX and A⁻ denotes Cl⁻, Br⁻, I⁻, $BF_4^-$, $PF_6^-$, $ClO_4^-$, sulfate, tosylate, hydrosulfate, triflate, trifluoroacetate, acetate or oxalate, are reacted with a compound of the general formula XXII

E⁺Y⁻       (XXII)

where Y⁻ has the meaning indicated in the case of formula I, II-1 to II-4 or a preferred meaning and E⁺ is a cation of the alkali metals, alkaline earth metals or of a metal from group 11 and 12.

The reaction, which can also be referred to as salt exchange, is carried out in organic solvents, preferably in aqueous solutions at temperatures of 0° to 100° C., preferably at 10° to 40° C., particularly preferably at room temperature. However, E⁺ may also have the meaning ammonium, alkylammonium containing $C_1$-$C_4$-alkyl, phosphonium, alkylphosphonium containing $C_1$-$C_4$-alkyl, imidazolium, guanidinium, uronium, thiouronium, pyridinium, pyrrolidinium or other heterocyclic cations, in which case the reaction is carried out in water or in organic water-miscible solvents, for example dimethoxyethane, acetonitrile, acetone, tetrahydrofuran, dimethylformamide, dimethyl sulfoxide, dioxane, propionitrile, benzonitrile, methanol, ethanol or isopropanol.

E⁺ is preferably a cation of the alkali metals, alkaline earth metals or of a metal from group 11 and 12, ammonium, alkylammonium containing $C_1$-$C_4$-alkyl, phosphonium, alkylphosphonium containing $C_1$-$C_4$-alkyl or guanidinium. Alkylammonium containing $C_1$-$C_4$-alkyl is taken to mean both ammonium which is monosubstituted or di-, tri- or tetrasubstituted by alkyl groups having 1-4 C atoms. Alkylphosphonium containing $C_1$-$C_4$-alkyl is taken to mean both phosphonium which is monosubstituted or di-, tri- or tetrasubstituted by alkyl groups having 1-4 C atoms. E⁺ is very particularly preferably an alkali metal cation, for example Li⁺ or K⁺.

The invention also relates to a process for the preparation of carbocyanine dyes of the formula XXIII

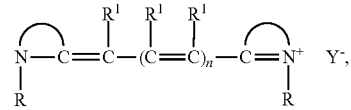

XXIII where n denotes 0, 1, 2, 3, 4 or 5,

R in each case, independently of one another, denotes alkyl, alkenyl, cycloalkyl, aryl or heteroaryl and R¹ in each case, independently of one another, denotes H, Cl, Br, I, alkyl, partially or fully chlorinated alkyl, alkenyl, cycloalkyl, aryl, heteroaryl, Oalkyl, Oaryl, Salkyl, Saryl, NHalkyl, N(alkyl)₂, C(O)H, C(O)alkyl, C(O)aryl, CN, N=N-aryl, P(aryl)₂, NHCOalkyl or NHCOaryl and the ring system, represented by

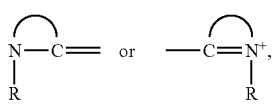

denotes a nitrogen-containing unsaturated mono-, bi- or tricyclic heterocycle having 5 to 13 ring members, which may furthermore contain 1, 2 or 3 N and/or 1 or 2 S or O atoms and in which the heterocyclic radical may be mono- or polysubstituted by Z as described above and where Y⁻ is an anion selected from the group CAB⁻, FAP⁻, FAB⁻ or Im⁻,
where CAB⁻ conforms to the general formula (II-1)

$$[B(CN)_{y1}F_{4-y1-x1}(R^0)_{x1}]^- \qquad (\text{II-1})$$

and
y1 denotes 1, 2, 3 or 4,
x1 denotes 0, 1, 2 or 3 and
$R^0$ denotes alkyl, aryl, fluorinated alkyl, fluorinated aryl, cycloalkyl or alkylaryl, with the condition that $R^0$ may be hydrogen if Y1 is >2, where FAP⁻ conforms to the general formula (II-2)

$$[P(C_{p2}F_{2p2+1-m2}H_{m2})_{y2}F_{6-y2}]^- \qquad (\text{II-2})$$

with
p2: 1 to 20,
m2: 0, 1, 2 or 3 and
y2: 1, 2, 3 or 4,
where FAB⁻ conforms to the general formula (II-3)

$$[B(C_{p3}F_{2p3+1-m3}H_{m3})_{y3}F_{4-y3}]^- \qquad (\text{II-3})$$

with
p3 1 to 20,
m3 0, 1, 2 or 3 and
y3 1, 2, 3 or 4,
where Im⁻ conforms to the general formula (II-4)

$$[(C_{p4}F_{2p4+1-m4}H_{m4}XO_{y4})N(C_qF_{2q+1-k}H_kXO_{y4})]^- \qquad (\text{II-4})$$

and the variables
X denotes carbon or sulfur,
p4 denotes 0 to 20 and $0 \leq m4 \leq 2p4+1$,
q denotes 0 to 20 and $0 \leq k \leq 2q+1$,
y4 denotes 1 or 2,
where m4=0 if p4=0 and k=0 if q=0, with the proviso if X is sulfur, y4 denotes 2 and if X is carbon, y4 denotes 1 and p4 or $q \geq 1$, and where the carbon atoms of the alkyl chain of the formula II-4 may be bonded to one another by single bonds, where the resultant alkylene chain may in turn be partially or fully substituted by F,
characterised in that use is made of a compound of the formula XXIV

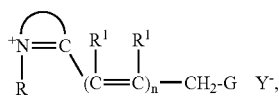     XXIV where the ring system and Y– have one of the meanings indicated in the case of formula XXIII and
n denotes 0, 1, 2, 3 or 4,
$R^1$ denotes hydrogen, alkyl, alkenyl, aryl, heteroaryl, Saryl, Salkyl, Oalkyl, CON(alkyl)₂, Oaryl, N(alkyl)₂, NH(aryl), N(alkyl)(aryl), OC(O)aryl, OH, CN, Cl, F, alkylaryl, C(O)alkyl, CONH₂ or COOalkyl,
G denotes hydrogen, alkyl, alkenyl, aryl, heteroaryl, N=C(R)₂, CONHaryl, C(O)aryl or CONHalkyl and
R denotes alkyl, alkenyl, cycloalkyl, aryl or heteroaryl.

The synthesis of the carbocyanine dyes of the formula XXIII using starting materials of the formula XXIV as described above can be carried out by methods which are known to the person skilled in the art, in particular by the procedures from T. V. S. Rao, J. B. Huff, C. Bieniarz, Tetrahedron 54 (1998), 10627-10634, L. G. S. Brooker, F. L. White, G. H. Keyes, C. P. Smyth and P. F. Oesper, J. Am. Chem. Soc, 63, (1941), 3192-3203 or F. M. Hamer and R. J. Rathbone, J. Chem. Soc, (1945), 595-600.

The invention also relates to compounds of the formula XXIV. In particular compounds of the formula XXIV in which G denotes hydrogen. Preferred compounds of the formula XXIV are the following compounds, where Y⁻ has a meaning in the case of formula I or the formulae II-1 to II-4 or a preferred meaning:

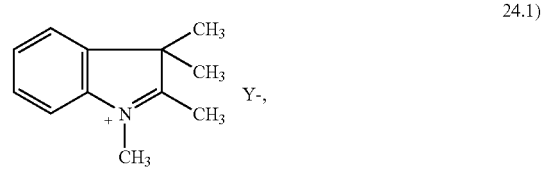

24.1)

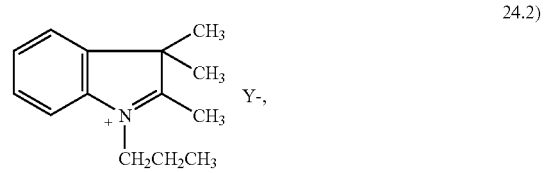

24.2)

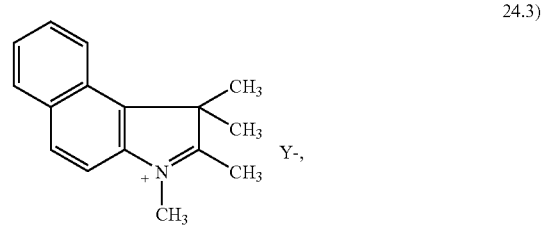

24.3)

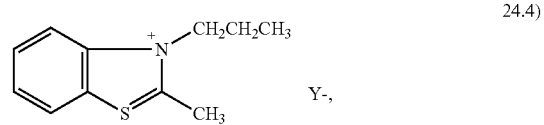

24.4)

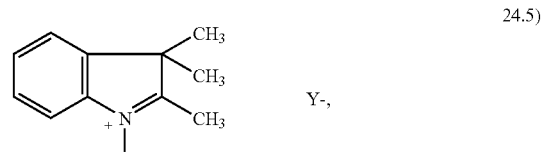

24.5)

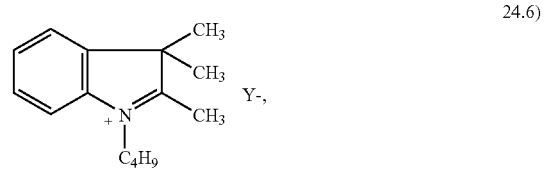

24.6)

-continued
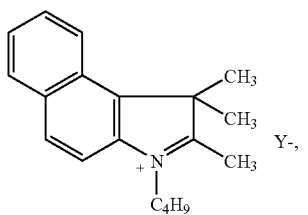  24.7)
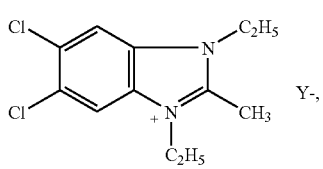  24.8)
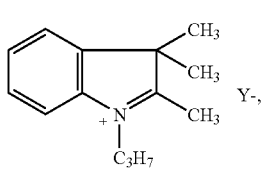  24.9)
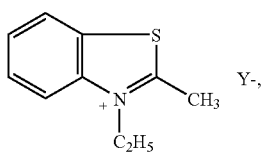  24.10)
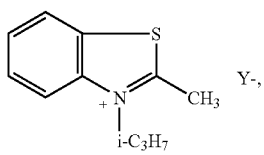  24.11)
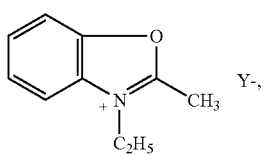  24.12)
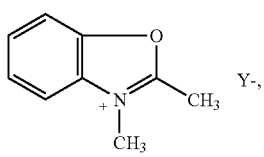  24.13)
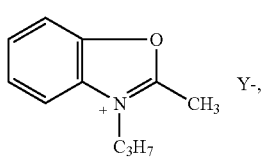  24.14)
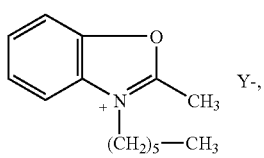  24.15)
-continued
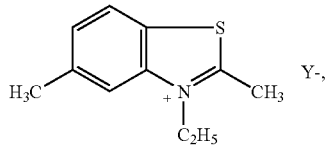  24.16)
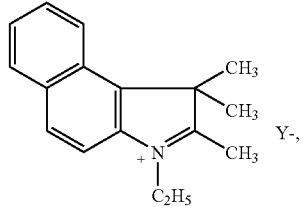  24.17)
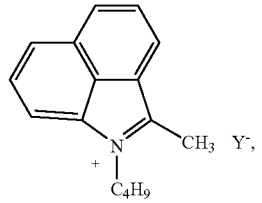  24.18)
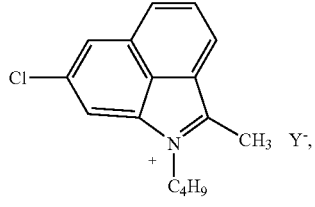  24.19)
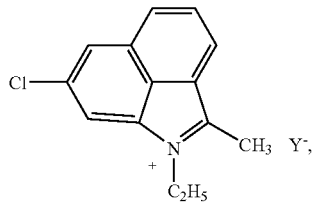  24.20)
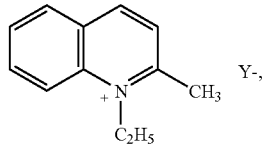  24.21)
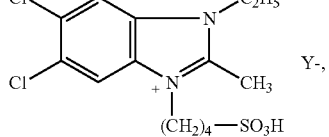  24.22)
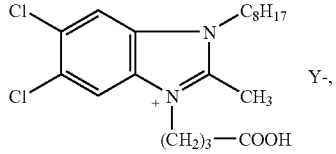  24.23)

-continued

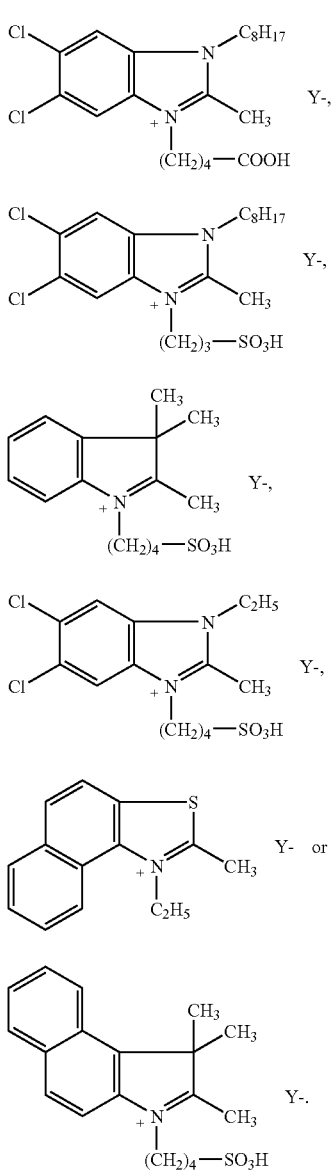

The invention furthermore relates to a process for the preparation of the compounds of the formula XXIV as defined above, characterised in that a compound of the formula XXV

XXV

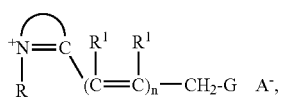

in which $A^-$ denotes $Cl^-$, $Br^-$, $I^-$, $BF_4^-$, $PF_6^-$, $ClO_4^-$, sulfate, tosylate, hydrosulfate, triflate, trifluoroacetate, acetate or oxalate, the ring system, represented by

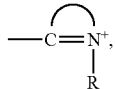

denotes a nitrogen-containing unsaturated mono-, bi- or tricyclic heterocycle having 5 to 13 ring members, which may furthermore contain 1, 2 or 3 N and/or 1 or 2 S or O atoms and in which the heterocyclic radical may be mono- or polysubstituted by Z as described above, n denotes 0, 1, 2, 3 or 4, $R^1$ denotes hydrogen, alkyl, alkenyl, aryl, heteroaryl, Saryl, Salkyl, Oalkyl, CON(alkyl)$_2$, Oaryl, N(alkyl)$_2$, NH(aryl), N(alkyl)(aryl), OC(O)aryl, OH, CN, Cl, F, alkylaryl, C(O)alkyl, CONH$_2$ or COOalkyl, R denotes alkyl, alkenyl, cycloalkyl, aryl or heteroaryl and G denotes hydrogen, alkyl, alkenyl, aryl, heteroaryl, N═C(R)$_2$, CONHaryl, C(O)aryl or CONHalkyl, is reacted with a compound of the formula XXVI $E^+Y^-$   XXVI, in which $Y^-$ has the meaning indicated in the case of formula I or the formulae II-1 to II-4 or a preferred meaning and $E^+$ is a cation of the alkali metals, alkaline earth metals or of a metal from group 11 or 12.

The reaction, which can also be referred to as salt exchange, is preferably carried out in aqueous solutions at temperatures of 0° to 100° C., preferably at 10° to 40° C., particularly preferably at room temperature. However, $E^+$ may also have the meaning ammonium, alkylammonium containing $C_1$-$C_4$-alkyl, phosphonium, alkylphosphonium containing $C_1$-$C_4$-alkyl, imidazolium, guanidinium, uronium, thiouronium, pyridinium, pyrrolidinium or other heterocyclic cations, in which case the reaction is preferably carried out in organic solvents, for example in alcohols.

$E^+$ is preferably a cation of the alkali metals, alkaline earth metals or of a metal from group 11 and 12, ammonium, alkylammonium containing $C_1$-$C_4$-alkyl, phosphonium, alkylphosphonium containing $C_1$-$C_4$-alkyl or guanidinium. $E^+$ is very particularly preferably an alkali metal cation, for example $Li^+$ or $K^+$.

The invention furthermore relates to an alternative process for the preparation of the compounds of the formula XXIV, with the restriction that n in formula XXIV denotes 0, characterised in that a compound of the formula XXVII

XXVII

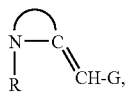

in which

G denotes hydrogen, alkyl, alkenyl, aryl, heteroaryl, N═C(R)$_2$, CONHaryl, C(O)aryl or CONHalkyl and R denotes alkyl, alkenyl, cycloalkyl, aryl or heteroaryl and the ring system, represented by

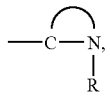

denotes a nitrogen-containing unsaturated mono-, bi- or tricyclic heterocycle having 5 to 13 ring members, which may furthermore contain 1, 2 or 3 N and/or 1 or 2 S or O atoms and in which the heterocyclic radical may be mono- or polysubstituted by Z as described above, is reacted with HY, where Y⁻ has the meaning indicated in the case of the formulae II-2 to 11-4 or a preferred meaning.

The preparation of HFAP is described, for example, in WO 03/02579.

The preparation of HFAB is described, for example, in R. D. Chambers et al, J. Am. Chem. Soc. 82, (1960), 5298.

The reaction with HY, with Y as defined in the case of the formulae II-2 to II4 is preferably carried out in an organic solvent at temperatures of −30° to 40° C., preferably at −0° to 25° C., particularly preferably at room temperature. A preferred solvent is ethanol.

The invention also relates to a process for the preparation of azo dyes having the formula XXVIII (R'N=N—R'')⁻Y⁻      XXVIII where R' and R'' denote aryl or heteroaryl and one of the two aromatic nuclei is positively charged and Y⁻ has one of the meanings indicated in the case of formula I or the formulae II-1 to II-4, characterised in that a compound of the formula XXIX

R'—N₂⁺Y⁻      XXIX where R' and Y⁻ has one of the meaning indicated in the case of formula XXVIII, is reacted with the aromatic cyclic or heterocyclic compound R''.

The reaction is carried out under reaction conditions which are typical of azo couplings and which are adequately known to the person skilled in the art, for example from Beyer Walter, Lehrbuch der Organischen Chemie [Textbook of Organic Chemistry], 21st Edition, S. Hirzel Verlag Stuttgart 1988.

The invention also relates to compounds of the formula XXIX. Preferred compounds of the formula XXIX are the following compounds, where Y⁻ has a meaning indicated in the case of formula I, the formulae II-1 to II-4 or a preferred meaning:

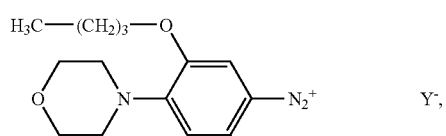
29.1)

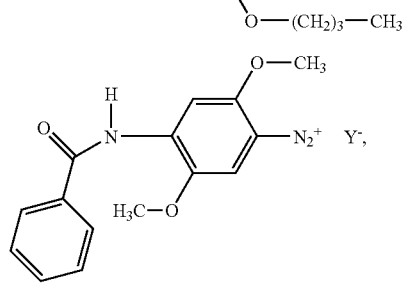
29.2)

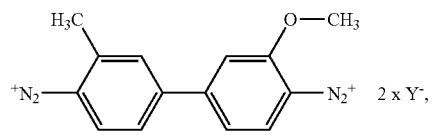
29.3)

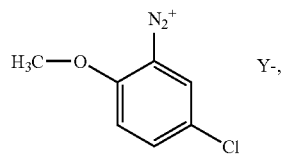
29.4)

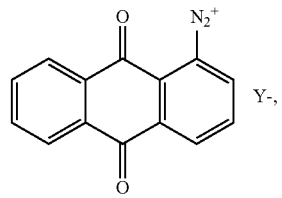
29.5)

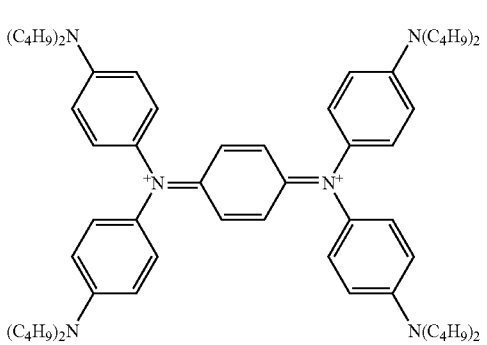
29.6)

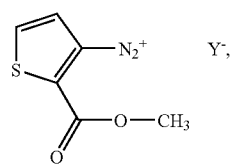
29.7)

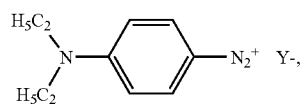
29.8)

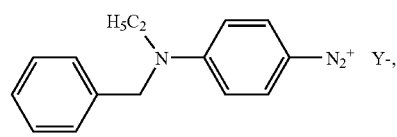
29.9)

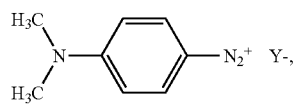
29.10)

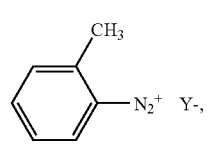
29.11)

-continued

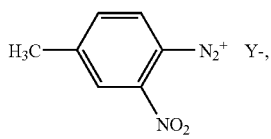
29.12)

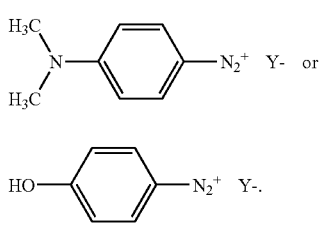
29.13)

HO—⟨⟩—N₂⁺ Y-.
29.14)

The synthesis of the compounds of the formula XXIX is carried out analogously to known methods of diazotisation with subsequent salt exchange, as described above.

The following examples are intended to explain the invention in greater detail, but without restricting it.

EXAMPLE 1

Preparation of an Azo Dye as Tetracyanoborate from Janus Green

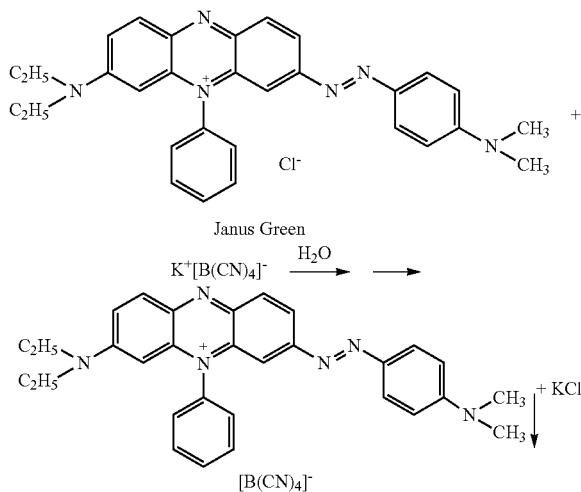

0.49 g (0.959 mmol) of the dye Janus Green are dissolved in 100 cm³ of water. 0.15 g (0.975 mmol) of potassium tetracyanoborate, K[B(CN)₄], in 5 cm³ of water are added dropwise to this solution at room temperature with stirring. The reaction mixture is stirred for a further 5 min. The precipitate is filtered off and washed 3× with 50 cm³ of water. The residue is dried under a reduced pressure of 1.3 Pa at 80° C., giving 0.41 g of Janus Green as tetracyanoborate, corresponding to a yield of 72.4%.

$^{11}$B NMR (reference: BF₃.OEt₂ external; CD₃CN): −38.58 s.

$^1$H NMR (reference: TMS; CD₃CN): 0.99 m (CH₃), 1.24 m (CH₃), 3.03 m (2CH₃), 3.29 m (CH₂), 3.65 m (CH₂), 5.63 s (1H), 6.56 s (1H), 6.58 s (1H), 7.01 s (1H), 7.44-7.54 m (4H), 7.58 d (1H), 7.80-7.95 m (5H), 8.08 d (1H); $J_{H,H}$=9.0 Hz.

EXAMPLE 2

Preparation of an Azine Dye as Tetracyanoborate from Safranine O

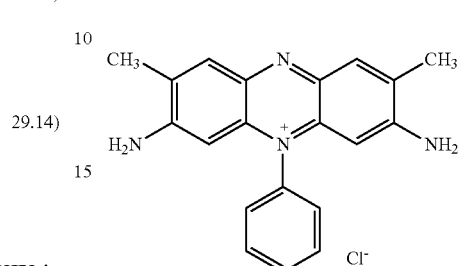
Safranine O

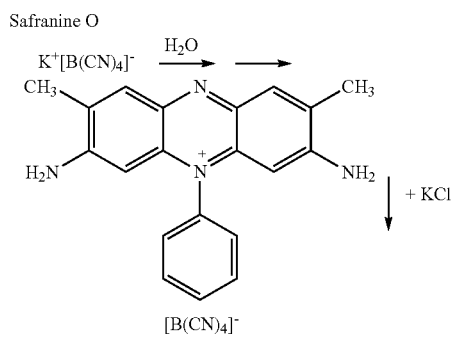

0.57 g (1.62 mmol) of the dye safranine O are dissolved in 100 cm³ of water. 0.26 g (1.69 mmol) of potassium tetracyanoborate, K[B(CN)₄], in 5 cm³ of water are added dropwise to this solution at room temperature with stirring. The reaction mixture is stirred for a further 5 min. The precipitate is filtered off and washed 3× with 50 cm³ of water. The residue is dried under a reduced pressure of 1.3 Pa and at 80° C., giving 0.64 g of safranine O as tetracyanoborate, corresponding to a yield of 91.8%.

$^{11}$B NMR (reference: BF₃.OEt₂ external; CD₃CN): −38.57 s.

$^1$H NMR (reference: TMS;CD₃CN): 2.27 d (2CH₃), 5.99 br.s (2NH₂), 7.45-7.52 m (2H), 7.71 s (2H), 7.74-7.89 m (5H), [4]$J_{H,H}$=1.0 Hz.

EXAMPLE 3

Preparation of a Xanthene Dye as Tetracyanoborate from Rhodamine B

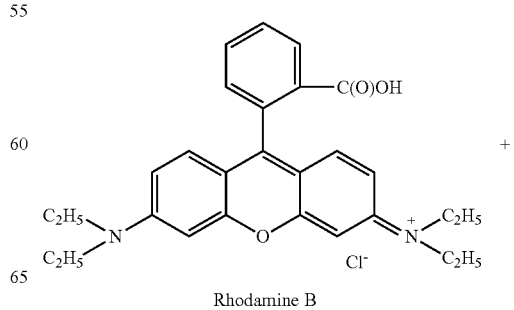
Rhodamine B

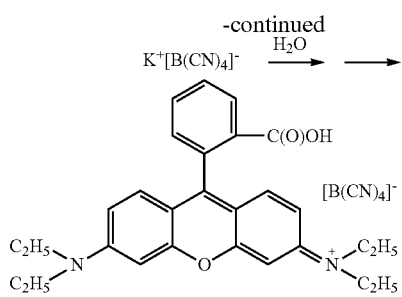

0.68 g (1.42 mmol) of the dye rhodamine B are dissolved in 100 cm³ of water. 0.23 g (1.50 mmol) of potassium tetracyanoborate, K[B(CN)₄], in 5 cm³ of water are added dropwise to this solution at room temperature with stirring. The reaction mixture is stirred for a further 5 min. The precipitate is filtered off and washed 3× with 50 cm³ of water. The residue is dried under a reduced pressure of 1.3 Pa and at 80° C., giving 0.755 g of rhodamine B as tetracyanoborate, corresponding to a yield of 95.2%.

¹¹B NMR (reference: BF₃.OEt₂ external; CD₃CN): −38.60 s.

¹H NMR (reference: TMS; CD₃CN): 1.25 t (4-CH₃), 3.60 q (4CH₂), 6.82 s (1H), 6.83 s (1H), 6.90 d, 6.92 d (2H; A,B), 7.05 s, 7.07 s (2H; A,B), 7.36 d,d (1H), 7.74-7.85 m (2H), 8.27 d,d (1H); ³$J_{H,H}$=7.1 Hz, $J_{H,H}$=2.4 Hz, $J_{A,B}$=9.5 Hz, $J_{H,H}$=7.6 Hz, $J_{H,H}$=1.0 Hz.

EXAMPLE 4

Preparation of an Oxazine Dye as Tetracyanoborate from Nile Blue

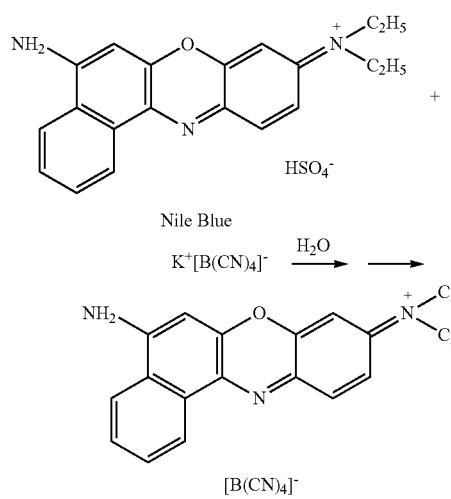

0.62 g (1.49 mmol) of the dye Nile Blue hydrogensulfate are dissolved in 100 cm³ of water. 0.24 g (1.56 mmol) of potassium tetracyanoborate, K[B(CN)₄], in 5 cm³ of water are added dropwise to this solution at room temperature with stirring. The reaction mixture is stirred for a further 5 min. The precipitate is filtered off and washed 3× with 50 cm³ of water. The residue is dried under a reduced pressure of 1.3 Pa and at 80° C., giving 0.59 g of Nile Blue as tetracyanoborate, corresponding to a yield of 88.2%.

¹¹B NMR (reference: BF₃.OEt₂ external; CD₃CN): −38.54 s.

¹H NMR (reference: TMS; CD₃CN): 1.28 t (2CH₃), 3.56 q (2CH₂), 6.32 s (1H), 6.45 d (1H), 6.98 d,d (1H), 7.41 s (NH₂), 7.38 d (1H), 7.55-7.78 m (3H), 8.35 d (1H); ³$J_{H,H}$=7.1 Hz, $J_{H,H}$=3.1 Hz, $J_{H,H}$=2.7 Hz, $J_{H,H}$=9.5 Hz, $J_{H,H}$=8.0 Hz.

EXAMPLE 5

Preparation of 3-ethyl-2-methylbenzothiazolium tetracyanoborate

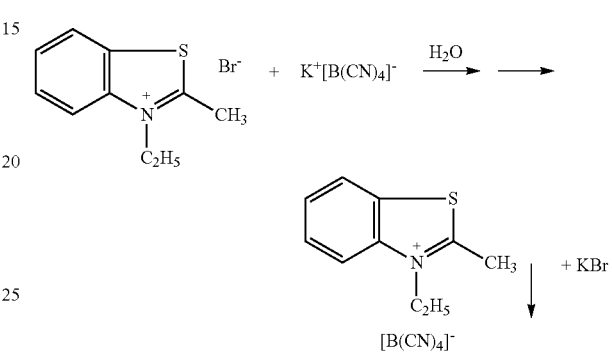

1.64 g (10.66 mmol) of potassium tetracyanoborate, K[B(CN)₄], in 5 ml of water are added dropwise with stirring to a solution of 2.76 g (10.69 mmol) of 3-ethyl-2-methylbenzothiazolium bromide in 50 ml of water. The lower liquid phase is extracted a number of times with 50 ml of dichloromethane, and the combined organic phases are dried using Mg₂SO₄. The solvent is subsequently removed by distillation, and the residue is dried under a reduced pressure of 1.3 Pa and at 60° C., giving 2.78 g of 3-ethyl-2-methylbenzothiazolium tetracyanoborate, corresponding to a yield of 89.1%.

¹H NMR (reference: TMS; CD₃CN): 1.53 t (CH₃), 3.09 s (CH₃), 4.67 q (CH₂), 7.79 t (1H), 7.89 t (1H), 8.10 d (1H), 8.21 d (1H); ³$J_{H,H}$=8.4 Hz, ³$J_{H,H}$=7.4 Hz.

EXAMPLE 6

Preparation of 3-ethyl-2-[3-(3-ethyl-3H-benzothiazol-2-ylidene)propenyl]-benzothiazolium tetracyanoborate

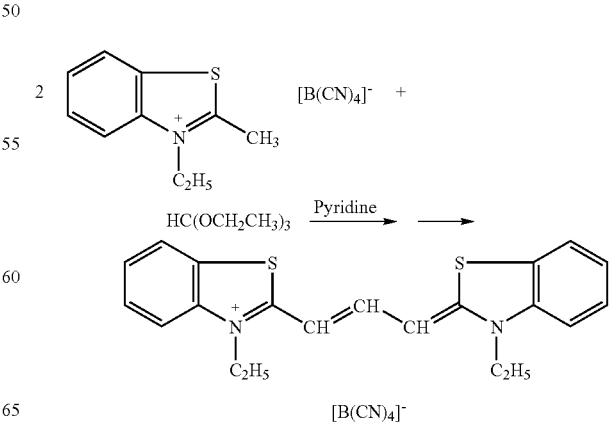

2.73 g (9.32 mmol) of 3-ethyl-2-methylbenzothiazolium tetracyanoborate are added to a solution of 0.710 g (4.79 mmol) of triethyl orthoformate in 15 ml of dry pyridine. The reaction mixture is heated at an oil-bath temperature of 110-115° C. under a protective-gas atmosphere for 15 hours. After the solvent has been removed by distillation under a reduced pressure of 1.3 Pa and at 80° C., the solid is washed a number of times with cold ethanol and dried under a reduced pressure of 1.3 Pa and at 60° C., giving 1.76 g of 3-ethyl-2-[3-(3-ethyl-3H-benzothiazol-2-ylidene)propenyl]benzothiazolium tetracyanoborate, corresponding to a yield of 78.6%.

$^1$H NMR (reference: TMS; CD$_3$CN): 1.38 t (2CH$_3$), 4.21 q (2CH$_2$), 6.30 d (2H), 7.32 m (2H), 7.48 m (4H), 7.75 d (2H), 7.78 t (1H); $^3J_{H,H}$=12.7 Hz, $^3J_{H,H}$=7.2 Hz, $J_{H,H}$=7.7 Hz.

EXAMPLE 7

Solubility Investigations of Nile Blue as Tetracyanoborate

The dye prepared in Example 4 from Nile Blue is exposed to various solvents.

As reference, the conventional dye Nile Blue with hydrogensulfate as anion is investigated under identical conditions.

TABLE 1

| Solubility of Nile Blue with HSO$_4^-$ or [B(CN)$_4$]$^-$ | | |
|---|---|---|
| Solvent | Hydrosulfate anion | [B(CN)$_4$]$^-$ |
| Water | +++ | − |
| Methanol | +++ | +++ |
| Benzene | − | + |
| Hexane | − | − |
| Diethyl ether | ++ | ++ |
| Tetrahydrofuran | + | +++ |
| Dimethyl carbonate | − | ++ |
| Ethyl acetate | + | +++ |

Key:
− insoluble,
+ soluble,
++ readily soluble,
+++ very readily soluble

EXAMPLE 8

Solubility Investigations of Rhodamine B as Tetracyanoborate

The dye prepared in Example 3 from rhodamine B is exposed to various solvents.

As reference, the conventional dye rhodamine B with chloride as anion is investigated under identical conditions.

TABLE 2

| Solubility of rhodamine B with Cl$^-$ or [B(CN)$_4$]$^-$ | | |
|---|---|---|
| Solvent | Cl$^-$ | [B(CN)$_4$]$^-$ |
| Water | +++ | − |
| Methanol | +++ | +++ |
| Benzene | −+ | ++ |
| Hexane | − | − |
| Diethyl ether | −+ | ++ |
| Tetrahydrofuran | ++ | +++ |

TABLE 2-continued

| Solubility of rhodamine B with Cl$^-$ or [B(CN)$_4$]$^-$ | | |
|---|---|---|
| Solvent | Cl$^-$ | [B(CN)$_4$]$^-$ |
| Dimethyl carbonate | ++ | +++ |
| Ethyl acetate | + | +++ |

Key:
− insoluble,
+ soluble,
++ readily soluble,
+++ very readily soluble

EXAMPLE 9

Solubility Investigations of Safranine O as Tetracyanoborate

The dye prepared in Example 2 from safranine O is exposed to various solvents.

As reference, the conventional dye safranine O with chloride as anion is investigated under identical conditions.

TABLE 3

| Solubility of safranine O with Cl$^-$ or [B(CN)$_4$]$^-$ | | |
|---|---|---|
| Solvent | Cl$^-$ | [B(CN)$_4$]$^-$ |
| Water | +++ | − |
| Methanol | +++ | +++ |
| Benzene | − | − |
| Hexane | − | − |
| Diethyl ether | − | + |
| Tetrahydrofuran | + | +++ |
| Dimethyl carbonate | −+ | ++ |
| Ethyl acetate | − | ++ |

Key:
− insoluble,
+ soluble,
++ readily soluble,
+++ very readily soluble

EXAMPLE 10

Solubility Investigations of Janus Green as Tetracyanoborate

The dye prepared in Example 4 from Janus Green is exposed to various solvents.

As reference, the conventional dye Janus Green with chloride as anion is investigated under identical conditions.

TABLE 4

| Solubility of Janus Green with Cl$^-$ or [B(CN)$_4$]$^-$ | | |
|---|---|---|
| Solvent | Cl$^-$ | [B(CN)$_4$]$^-$ |
| Water | +++ | − |
| Methanol | +++ | +++ |
| Benzene | − | + |
| Hexane | − | − |
| Diethyl ether | − | + |
| Tetrahydrofuran | ++ | +++ |
| Dimethyl carbonate | +− | ++ |
| Ethyl acetate | + | +++ |

Key:
− insoluble,
+ soluble,
++ readily soluble,
+++ very readily soluble

EXAMPLE 11

Preparation of an Azo Dye as Tris(Pentafluoroethyl)Trifluorophosphate from Janus Green

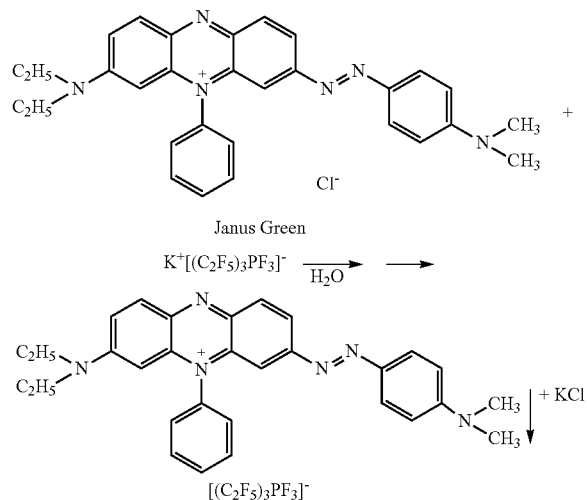

0.347 g (0.679 mmol) of the dye Janus Green are dissolved in 100 cm³ of water. 0.380 g (0.7853 mmol) of potassium tris (pentafluoroethyl)trifluorophosphate, K[($C_2F_5$)$_3$ PF$_3$], in 3 cm³ of water are added dropwise to the solution at room temperature with stirring. The reaction mixture is stirred for a further 5 min. The precipitate is filtered off and washed 3× with 20 cm³ of water. The residue is dried under reduced pressure, giving 0.481 g of Janus Green as tris(pentafluoroethyl)trifluorophosphate. The yield is 77%.

$^{19}$F NMR (reference: CCl$_3$F; solvent: CD$_3$CN): −43.54 d,m (PF), −79.63 m (CF$_3$), −81.32 m (2CF$_3$), −86.98 d,m (PF$_2$), −115.02 dm (CF$_2$) −115.62 dm (2CF$_2$); $^1J_{P,F}$=889 Hz, $^1J_{P,F}$=902 Hz, $^2J_{P,F}$=86 Hz, $^2J_{P,F}$=98 Hz.

$^1$H NMR (reference: TMS; solvent: CD$_3$CN): 1.01 m (CH$_3$), 1.27 m (CH$_3$), 3.06 m (2CH$_3$), 3.32 m (CH$_2$), 3.67 m (CH$_2$), 5.68 d (1H), 6.62 s (1H), 6.65 s (1H), 7.08 d (1H), 7.50-7.66 m (5H), 7.85-7.98 m (5H), 8.15 d (1H); $J_{H,H}$=2.5 Hz; $J_{H,H}$=1.8 Hz; $J_{H,H}$=9.0 Hz. $^{31}$P NMR (reference: 85% H$_3$PO$_4$; solvent: CD$_3$CN): −148.6 q,m.

EXAMPLE 12

Preparation of an Azine Dye as Tris(Pentafluoroethyl)Trifluorophosphate from Safranine O

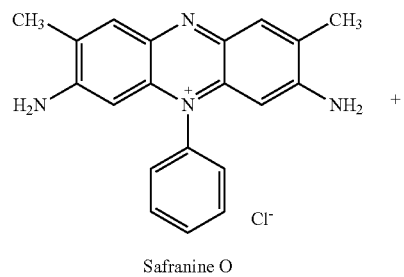

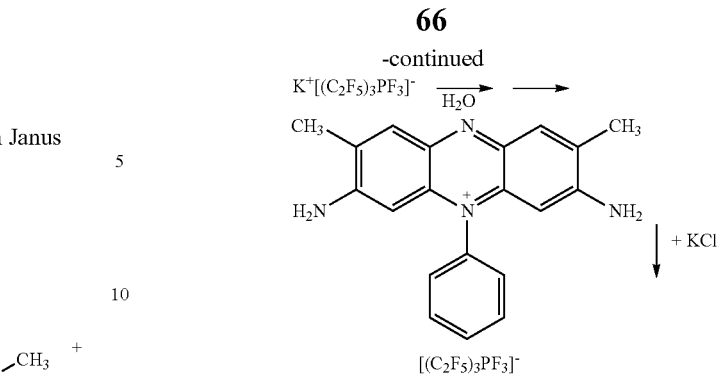

0.513 g (1.46 mmol) of the dye safranine O are dissolved in 100 cm³ of water. 0.780 g (1.61 mmol) of potassium tris (pentafluoroethyl)trifluorophosphate, K[($C_2F_5$)$_3$ PF$_3$] in 5 cm³ of water are added dropwise to the solution at room temperature with stirring. The precipitate is filtered off and washed 3× with 20 cm³ of water. The residue is dried under reduced pressure, giving 1.019 g of safranine O as tris(pentafluoroethyl)trifluorophosphate. The yield is 91.8%.

$^{19}$F NMR (reference: CCl$_3$F; solvent: CD$_3$CN): −43.55 d,m (PF), −79.67 m (CF$_3$), −81.35 m (2CF$_3$), −87.03 d,m (PF$_2$), −115.07 dm (CF$_2$) −115.68 dm (2CF$_2$); $^1J_{P,F}$=890 Hz, $^1J_{P,F}$=902 Hz, $^2J_{P,F}$=85 Hz, $^2J_{P,F}$=98 Hz.

$^1$H NMR (reference: TMS; solvent: CD$_3$CN): 2.30 br.s (2CH$_3$), 6.00-6.08 br.s (2NH$_2$), 7.48-7.55 m (2H), 7.75-7.78 m (2H), 7.83-7.91 m (5H).

$^{31}$P NMR (reference: 85% H$_3$PO$_4$; solvent: CD$_3$CN): −148.6 q,m.

EXAMPLE 13

Preparation of a Xanthene Dye as Tris(Pentafluoroethyl)Trifluorophosphate from Rhodamine B

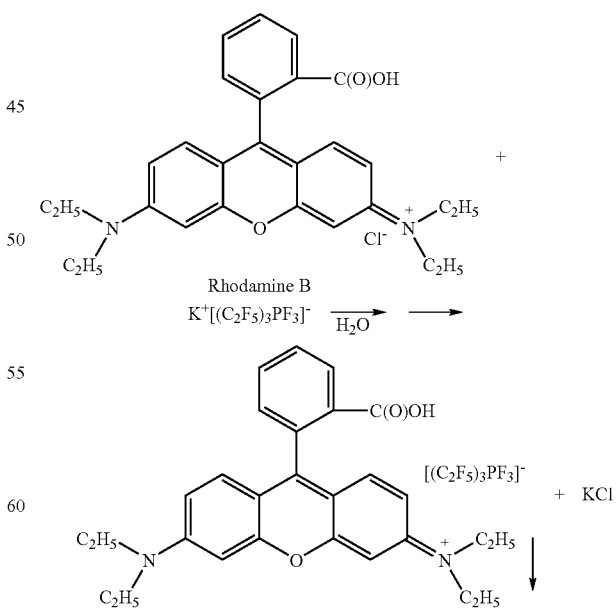

0.462 g (0.964 mmol) of the dye rhodamine B are dissolved in 100 cm³ of water. 0.502 g (1.037 mmol) of potassium tris (pentafluoroethyl)trifluorophosphate, K[(C$_2$F$_5$)$_3$ PF$_3$] in 3 cm$^3$ of water are added dropwise to the solution at room temperature with stirring. The precipitate is filtered off and washed 3× with 20 cm$^3$ of water. The residue is dried under reduced pressure, giving 0.600 g of rhodamine B as tris(pentafluoroethyl)trifluorophosphate. The yield is 70%.

$^{19}$F NMR (reference: CCl$_3$F; solvent: CD$_3$CN): −43.58 d,m (PF), −79.64 m (CF$_3$), −81.34 m (2CF$_3$), −86.98 d,m (PF$_2$), −115.03 dm (CF$_2$) −115.64 dm (2CF$_2$); $^1J_{P,F}$=890 Hz, $^2J_{P,F}$=902 Hz, $^2J_{P,F}$=85 Hz, $^2J_{P,F}$=98 Hz.

$^1$H NMR (reference: TMS; solvent: CD$_3$CN): 1.28 t (4CH$_3$), 3.64 q (4CH$_2$), 6.85 s (1H), 6.86 s (1H), 6.93 d, 6.96 d (2H; A,B), 7.07 s, 7.11 (2H; A,B), 7.39 d,d (1H), 7.77-7.90 m (2H), 8.32 d,d (1H); $^3J_{H,H}$=7.1 Hz, $J_{H,H}$=2.5 Hz, $J_{H,H}$=1.5 Hz, $J_{H,H}$=7.4 Hz, $J_{H,H}$=9.2 Hz. $^{31}$P NMR (reference: 85% H$_3$PO$_4$; solvent: CD$_3$CN): −148.4 q,m.

EXAMPLE 14

Preparation of a Xanthene Dye as Tris(Pentafluoroethyl)Trifluorophosphate from Pyronine G

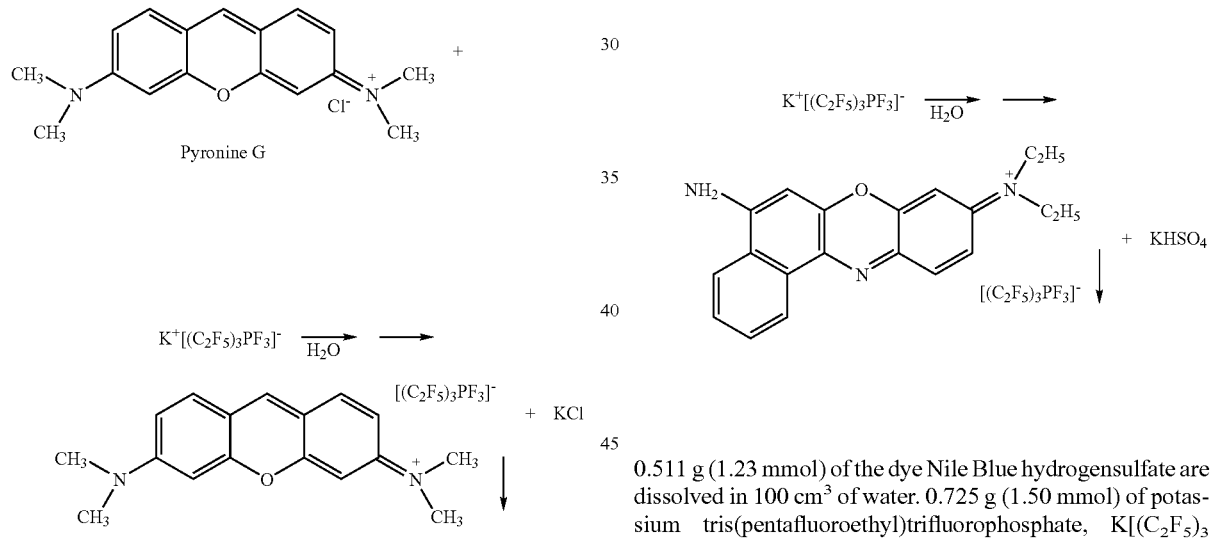

0.356 g (1.176 mmol) of the dye pyronine G are dissolved in 100 cm$^3$ of water. 0.602 g (1.243 mmol) of potassium tris (pentafluoroethyl)trifluorophosphate, K[(C$_2$F$_5$)$_3$ PF$_3$] in 5 cm$^3$ of water are added dropwise to the solution at room temperature with stirring. The precipitate is filtered off and washed 3× with 20 cm$^3$ of water. The residue is dried under reduced pressure, giving 0.655 g of pyronine G as tris(pentafluoroethyl)trifluorophosphate. The yield is 78.2%.

$^{19}$F NMR (reference: CCl$_3$F; solvent: CD$_3$CN): −43.56 d,m (PF), −79.62 m (CF$_3$), −81.31 m (2CF$_3$), −86.96 d,m (PF$_2$), −115.02 dm (CF$_2$) −115.63 dm (2CF$_2$); $^1J_{P,F}$=891 Hz, $^1J_{P,F}$=904 Hz, $^2J_{P,F}$=85 Hz, $^2J_{P,F}$=98 Hz.

$^1$H NMR (reference: TMS; solvent: CD$_3$CN): 3.25 s (4CH$_3$), 6.69 s (1H), 6.70 s (1H), 7.03 d, 7.06 d (2H; A,B), 7.67 s, 7.70 (2H; A,B), 8.38 br.s (1H); $J_{H,H}$=2.4 Hz, $J_{H,H}$=9.3 Hz.

$^{31}$P NMR (reference: 85% H$_3$PO$_4$; solvent: CD$_3$CN): −148.6 q,m.

EXAMPLE 15

Preparation of an Oxazine Dye as Tris(Pentafluoroethyl)Trifluorophosphate from Nile Blue

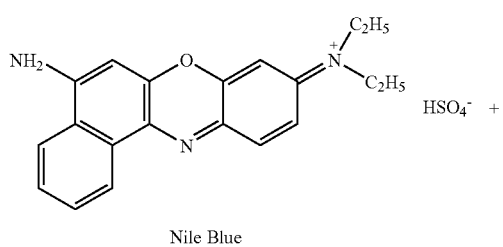

0.511 g (1.23 mmol) of the dye Nile Blue hydrogensulfate are dissolved in 100 cm$^3$ of water. 0.725 g (1.50 mmol) of potassium tris(pentafluoroethyl)trifluorophosphate, K[(C$_2$F$_5$)$_3$ PF$_3$] in 5 cm$^3$ of water are added dropwise to the solution at room temperature with stirring. The precipitate is filtered off and washed 3× with 20 cm$^3$ of water. The residue is dried under reduced pressure, giving 0.832 g of Nile Blue as tris (pentafluoroethyl)trifluorophosphate. The yield is 89.1%.

$^{19}$F NMR (reference: CCl$_3$F; solvent: CD$_3$CN): −43.57 d,m (PF), −79.65 m (CF$_3$), −81.33 m (2CF$_3$), −87.00 d,m (PF$_2$), −115.05 dm (CF$_2$) −115.66 dm (2CF$_2$); $^1J_{P,F}$=890 Hz, $^1J_{P,F}$=903 Hz, $^2J_{P,F}$=85 Hz, $^2J_{P,F}$=98 Hz.

$^1$H NMR (reference: TMS; solvent: CD$_3$CN): 1.30 t (2CH$_3$), 3.62 q (2CH$_2$), 6.54 s (1H), 6.62 d (1H), 7.10 d,d (1H), 7.50-7.98 m (6H), 8.59 d,d (1H); $^3J_{H,H}$=7.2 Hz, $J_{H,H}$=2.7 Hz, $J_{H,H}$=8.2 Hz, $J_{H,H}$=9.5 Hz.

$^{31}$P NMR (reference: 85% H$_3$PO$_4$; solvent: CD$_3$CN): −148.5 q,m.

EXAMPLE 16

Preparation of a Triphenylmethane Dye as Tris(Pentafluoroethyl)Trifluorophosphate from Crystal Violet

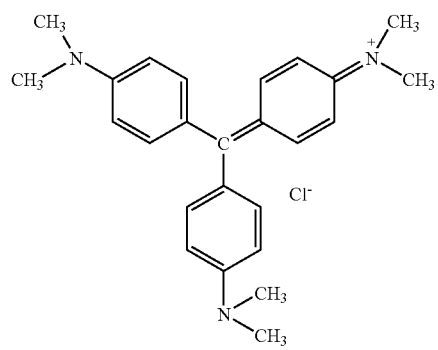

Crystal violet

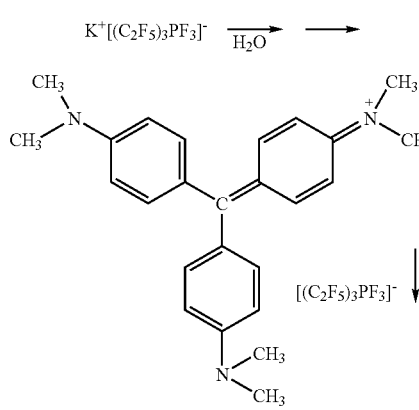

0.359 g (0.88 mmol) of the dye Crystal Violet are dissolved in 100 cm³ of water. 0.508 g (1.049 mmol) of potassium tris(pentafluoroethyl)trifluorophosphate, K[($C_2F_5$)$_3$ PF$_3$] in 5 cm³ of water are added dropwise to the solution at room temperature with stirring. The precipitate is filtered off and washed 3× with 20 cm³ of water. The residue is dried under reduced pressure, giving 0.559 g of Crystal Violet as tris(pentafluoroethyl)trifluorophosphate. The yield is 77.7%.

$^{19}$F NMR (reference: CCl$_3$F; solvent: CD$_3$CN): −43.55 d,m (PF), −79.58 m (CF$_3$), −81.28 m (2CF$_3$), −86.92 d,m (PF$_2$), −115.06 dm (CF$_2$) −115.57 dm (2CF$_2$); $^1J_{P,F}$=889 Hz, $^2J_{P,F}$=902 Hz, $^2J_{P,F}$=83 Hz, $^2J_{P,F}$=98 Hz.

$^1$H NMR (reference: TMS; solvent: CD$_3$CN): 3.20 s (6CH$_3$), 6.90 d,m; 7.30 d,m (12H; A,B), J$_{H,H}$=9.3 Hz.

$^{31}$P NMR (reference: 85% H$_3$PO$_4$; solvent: CD$_3$CN): −148.6 q,m.

EXAMPLE 17

Preparation of a Quinoline Dye as Tris(Pentafluoroethyl)Trifluorophosphate from Ethidium Bromide

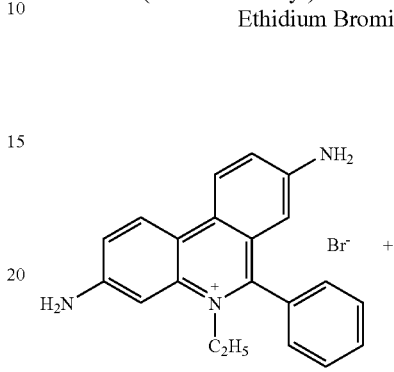

Ethidium bromide

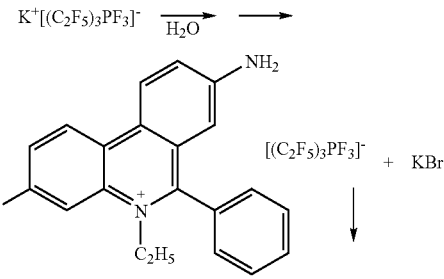

0.114 g (0.289 mmol) of the dye ethidium bromide are dissolved in 50 cm³ of water. 0.140 g (0.289 mmol) of potassium tris(pentafluoroethyl)trifluorophosphate, K[(C$_2$F$_5$)$_3$ PF$_3$], in 2 cm³ of water are added dropwise to the solution at room temperature with stirring. The reaction mixture is extracted with 50 cm³ of diethyl ether, and the extract is washed 2× with 40 cm³ of water and dried using anhydrous MgSO$_4$. The solvent is filtered off, and the residue is dried under reduced pressure, giving 0.207 g of ethidium as tris(pentafluoroethyl)trifluorophosphate. The yield is 94.5%.

$^{19}$F NMR (reference: CCl$_3$F; solvent: CD$_3$CN): −43.55 d,m (PF), −79.63 m (CF$_3$), −81.31 m (2CF$_3$), −87.00 d,m (PF$_2$), −115.02 dm (CF$_2$) −115.62 dm (2CF$_2$); $^1J_{P,F}$=890 Hz, $^1J_{P,F}$=902 Hz, $^2J_{P,F}$=84 Hz, $^2J_{P,F}$=98 Hz.

$^1$H NMR (reference: TMS; solvent: CD$_3$CN): 1.46 t (CH$_3$), 4.55 q (CH$_2$), 4.4 br. s (2NH$_2$), 6.45 d (1H), 7.30-7.83 m (8H), 8.42 d (1H), 8.50 d (1H);

$^3$J$_{H,H}$=7.2 Hz, J$_{H,H}$=2.4 Hz, J$_{H,H}$=9.3 Hz.

$^{31}$P NMR (reference: 85% H$_3$PO$_4$; solvent: CD$_3$CN): −148.6 q,m.

EXAMPLE 18

Preparation of a Thiazine Dye as Tris(Pentafluoroethyl)Trifluorophosphate from Methylene Blue

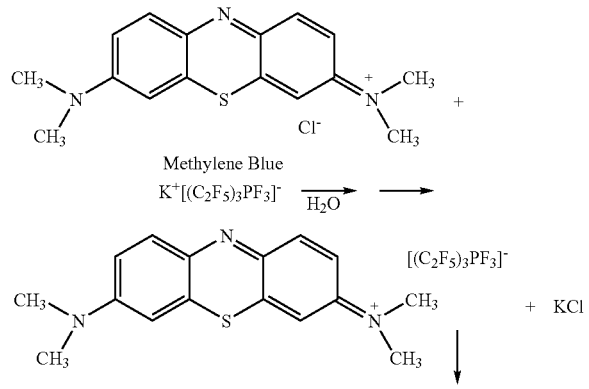

0.210 g (0.657 mmol) of the dye Methylene Blue are dissolved in 50 cm³ of water. 0.325 g (0.671 mmol) of potassium tris(pentafluoroethyl)trifluorophosphate, $K[(C_2F_5)_3PF_3]$ in 3 cm³ of water are added dropwise to the solution at room temperature with stirring. The precipitate is filtered off and washed 3× with 20 cm³ of water. The residue is dried under reduced pressure, giving 0.432 g of Methylene Blue as tris (pentafluoroethyl)trifluorophosphate. The yield is 90.2%.

$^{19}F$ NMR (reference: $CCl_3F$; solvent: $CD_3CN$): −43.56 d,m (PF), −79.64 m ($CF_3$), −81.33 m ($2CF_3$), −86.98 d,m ($PF_2$), −115.03 dm ($CF_2$) −115.65 dm ($2CF_2$); $^1J_{P,F}$=889 Hz, $^1J_{P,F}$=902 Hz, $^2J_{P,F}$=83 Hz, $^2J_{P,F}$=98 Hz.

$^1H$ NMR (reference: TMS; solvent: $CD_3CN$): 3.29 s ($4CH_3$), 7.10 s (1H), 7.11 s (1H), 7.28 d,d (2H; A,B), 7.80 d (2H; A,B), $J_{H,H}$=2.3 Hz, $J_{H,H}$=9.5 Hz.

$^{31}P$ NMR (reference: 85% $H_3PO_4$; solvent: $CD_3CN$): −148.5 q,m.

EXAMPLE 19

Preparation of an Azine Dye as Tris(Pentafluoroethyl)Trifluorophosphate from Safranine O

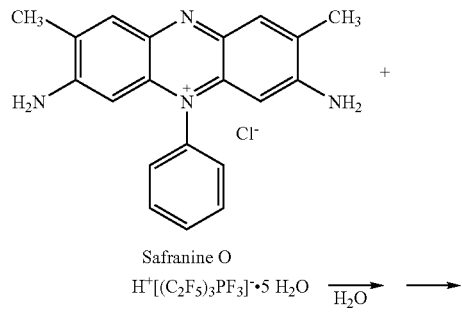

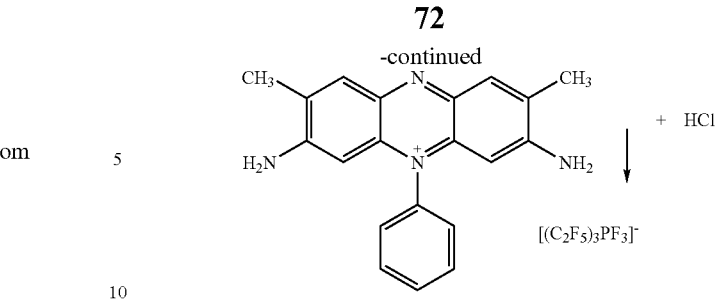

0.250 g (0.712 mmol) of the dye safranine O are dissolved in 50 cm³ of water. 0.390 g (0.727 mmol) of tris(pentafluoroethyl)trifluorophosphoric acid pentahydrate, $H[(C_2F_5)_3\ PF_3]$ $5H_2O$, in 3 cm³ of water are added dropwise to the solution at room temperature with stirring. The precipitate is filtered off and washed 3× with 20 cm³ of water. The residue is dried under reduced pressure, giving 0.490 g of safranine as tris (pentafluoroethyl)trifluorophosphate. The yield is 90.6%.

The material is analysed by means of $^1H$- and $^{19}F$-NMR and $^{31}P$ spectra and corresponds to the data indicated in Example 12.

EXAMPLE 20

Preparation of a Carbocyanine Dye as Tris(Pentafluoroethyl)Trifluorophosphate

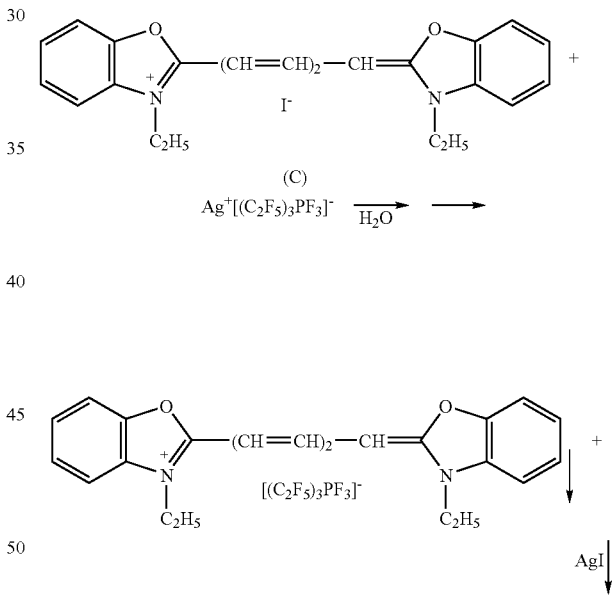

0.070 g (0.130 mmol) of tris(pentafluoroethyl)trifluorophosphoric acid pentahydrate, $H[(C_2F_5)_3\ PF_3]$ $5H_2O$, in 5 cm³ of water are neutralised using 0.020 g (0.086 mmol) of silver oxide. The resultant solution is added dropwise to a solution of 0.050 g (0.103 mmol) of the cyanine dye (C) in 200 cm³ of water with stirring. The precipitate is filtered off and washed 12× with 10 cm³ of methanol. The solvent is removed by distillation, and the residue is dried under reduced pressure at 60° C., giving 0.035 g of carbocyanine dye as tris(pentafluoroethyl)trifluorophosphate. The yield is 42.2%.

$^{19}F$ NMR (reference: $CCl_3F$; solvent: $CD_3CN$): −43.55 d,m (PF), −79.61 m ($CF_3$), −81.30 m ($2CF_3$), −86.98 d,m ($PF_2$), −115.01 dm ($CF_2$) −115.61 dm ($2CF_2$); $^1J_{P,F}$=890 Hz, $^1J_{P,F}$=902 Hz, $^2J_{P,F}$=85 Hz, $^2J_{P,F}$=98 Hz.

¹H NMR (reference: TMS; solvent: CD₃CN): 1.40 t (2CH₃), 4.11 q (2CH₂), 5.78 d (2H), 6.34 t (1H), 7.29-7.55 m (8H), 7.80 t (1H); $^3J_{H,H}$=7.2 Hz, $J_{H,H}$=13.0 Hz.

³¹P NMR (reference: 85% H₃PO₄; solvent: CD₃CN): −148.6 q,m.

EXAMPLE 21

Preparation of 1,2,3,3-tetramethyl-3H-indolium tris(pentafluoroethyl)trifluorophosphate

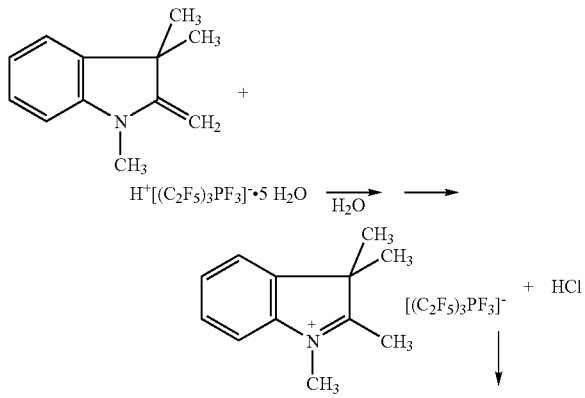

4.00 g (7.46 mmol) of tris(pentafluoroethyl)trifluorophosphoric acid pentahydrate, H[(C₂F₅)₃ PF₃] 5H₂O, are dissolved in 15 cm³ of water. 1.175 g (6.78 mmol) of 2-methylene-1,3,3-trimethylindoline (Fischer base) are added dropwise to the solution with stirring. The precipitate is filtered off and washed 3× with 10 cm³ of water. The residue is dried for 8 hours under a reduced pressure of 1.3 Pa and at room temperature, giving 4.16 g of 1,2,3,3-tetra methyl-3H-indolium tris(pentafluoroethyl)trifluorophosphate. The yield is 99%. The melting point after crystallisation from ethanol is 81° C.

¹⁹F NMR (reference: CCl₃F; solvent: CD₃CN): −43.51 d,m (PF), −79.54 m (CF₃), −81.23 m (2CF₃), −86.90 d,m (PF₂), −114.88 dm (CF₂) −115.49 dm (2CF₂); $^1J_{P,F}$=889 Hz, $^1J_{P,F}$=901 Hz, $^2J_{P,F}$=87 Hz, $^2J_{P,F}$=98 Hz.

¹H NMR (reference: TMS; solvent: CD₃CN): 1.55 s (2CH₃), 2.69 q (CH₃), 2.69 q (CH₃), 7.61-7.76 m (4H); $J_{H,H}$=0.7 Hz.

³¹P NMR (reference: 85% H₃PO₄; solvent: CD₃CN): −148.3 q,m.

EXAMPLE 22

Preparation of 3-ethyl-2-methylbenzothiazolium tris(pentafluoroethyl)trifluorophosphate

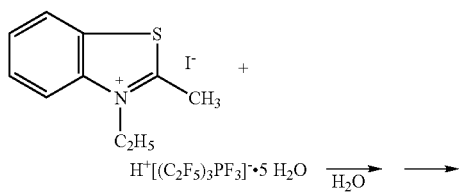

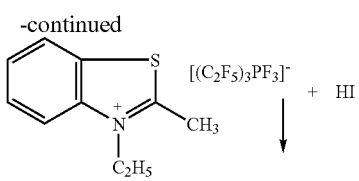

4.39 g (8.19 mmol) of tris(pentafluoroethyl)trifluorophosphoric acid pentahydrate, H[(C₂F₅)₃ PF₃] 5H₂O, are dissolved in 30 cm³ of water. 2.5 g (8.19 mmol) of 3-ethyl-2-methylbenzothiazolium iodide are added dropwise to the solution with stirring. The precipitate is filtered off and washed 3× with 10 cm³ of water. The residue is dried for 8 hours under a reduced pressure of 1.3 Pa and at 60° C., giving 5.03 g of 3-ethyl-2-methylbenzothiazolium tris(pentafluoroethyl)trifluorophosphate. The yield is 98.4%. The melting point after crystallisation from ethanol is 62-63° C.

¹⁹F NMR (reference: CCl₃F; solvent: CD₃CN): −43.56 d,m (PF), −79.68 m (CF₃), −81.37 m (2CF₃), −86.94 d,m (PF₂), −114.99 dm (CF₂) −115.63 dm (2CF₂); $^1J_{P,F}$=888 Hz, $^1J_{P,F}$=903 Hz, $^2J_{P,F}$=83 Hz, $^2J_{P,F}$=98 Hz.

¹H NMR (reference: TMS; solvent: CD₃CN): 1.54 t (CH₃), 3.09 s (CH₃), 4.67 q (CH₂), 7.79 t (1H), 7.89 t (1H), 8.10 d (1H), 8.22 d (1H); $^3J_{H,H}$=8.0 Hz, $^3J_{H,H}$=7.3 Hz.

³¹P NMR (reference: 85% H₃PO₄; solvent: CD₃CN): −148.0 q,m.

EXAMPLE 23

Preparation of 3-ethyl-2-methylbenzoxazolium tris(pentafluoroethyl)trifluorophosphate

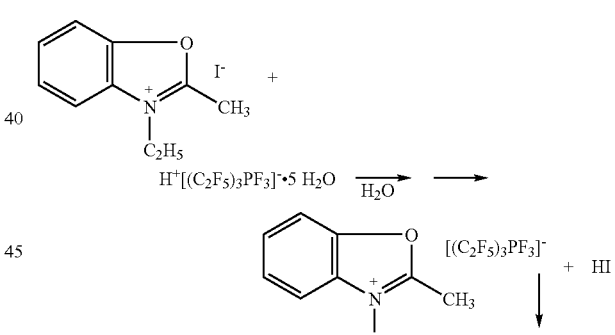

4.63 g (8.64 mmol) of tris(pentafluoroethyl)trifluorophosphoric acid pentahydrate, H[(C₂F₅)₃ PF₃] 5H₂O, are dissolved in 30 cm³ of water. 2.5 g (8.64 mmol) of 3-ethyl-2-methylbenzoxazolium iodide are added dropwise to the solution with stirring. The precipitate is filtered off and washed 3× with 10 cm³ of water. The residue is dried for 8 hours under a reduced pressure of 1.3 Pa and at 60° C., giving 4.49 g of 3-ethyl-2-methylbenzoxazolium tris(pentafluoroethyl)trifluorophosphate. The yield is 85.6%. The melting point after crystallisation from ethanol is 71-72° C.

¹⁹F NMR (reference: CCl₃F; solvent: CD₃CN): −43.56 d,m (PF), −79.68 m (CF₃), −81.40 m (2CF₃), −86.94 d,m (PF₂), −114.99 dm (CF₂) −115.64 dm (2CF₂); $^1J_{P,F}$=891 Hz, $^1J_{P,F}$=903 Hz, $^2J_{P,F}$=83 Hz, $^2J_{P,F}$=98 Hz.

¹H NMR (reference: TMS; solvent: CD₃CN): 1.54 t (CH₃), 3.00 s (CH₃), 4.50 q (CH₂), 7.73-7.81 m (2H), 7.88-7.96 m (2H); $^3J_{H,H}$=7.4 Hz.

EXAMPLE 24

Preparation of 2,3-dimethylbenzoxazolium tris(pentafluoroethyl)trifluorophosphate

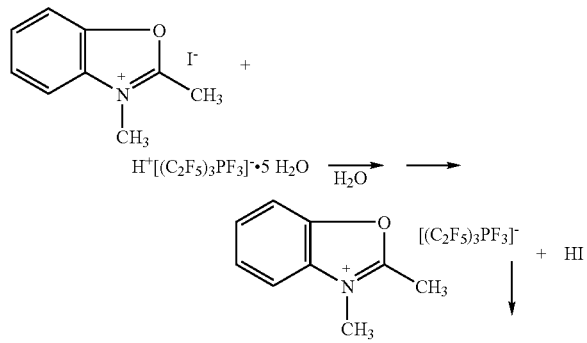

9.37 g (17.48 mmol) of tris(pentafluoroethyl)trifluorophosphoric acid pentahydrate, $H[(C_2F_5)_3 PF_3] \cdot 5H_2O$, are dissolved in 15 cm³ of water. 4.81 g (17.48 mmol) of 2,3-dimethylbenzoxazolium iodide in 50 cm³ of water are added dropwise to the solution with stirring. The precipitate is filtered off and washed 3× with 10 cm³ of water. The residue is dried for 8 hours under a reduced pressure of 1.3 Pa and at 70° C., giving 10.12 g of 2,2-dimethylbenzoxazolium tris(pentafluoroethyl)trifluorophosphate. The yield is 85.6%. The melting point after crystallisation from ethanol is 94-95° C.

$^{19}$F NMR (reference: $CCl_3F$; solvent: $CD_3CN$): −43.59 d,m (PF), −79.69 m ($CF_3$), −81.38 m ($2CF_3$), −86.96 d,m ($PF_2$), −115.01 dm ($CF_2$) −115.65 dm ($2CF_2$); $^1J_{P,F}$=890 Hz, $^1J_{P,F}$=909 Hz, $^2J_{P,F}$=81 Hz, $^2J_{P,F}$=99 Hz.

$^1$H NMR (reference: TMS; solvent: $CD_3CN$): 2.99 s ($CH_3$), 4.01 s ($CH_3$), 7.74-7.81 m (2H), 7.84-7.94 m (2H).

$^{31}$P NMR (reference: 85% $H_3PO_4$; solvent: $CD_3CN$): −148.1 q,m.

EXAMPLE 25

Preparation of 2-[3-(1,3-dihydro-1,3,3-trimethyl-2H-indol-2-ylidene)propenyl]-1,3,3-trimethyl-3H-indolium tris(pentafluoroethyl)trifluorophosphate

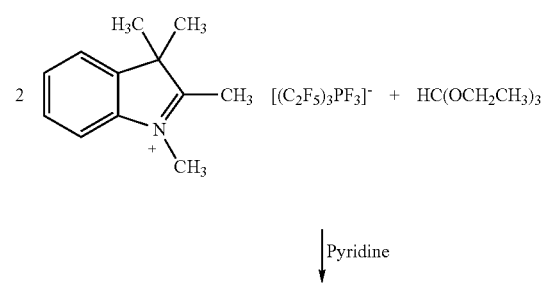

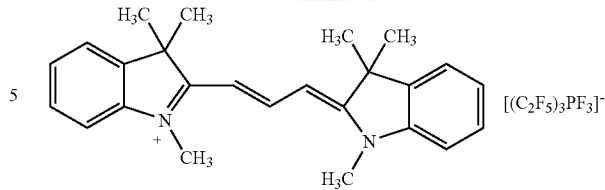

1.642 g (2.65 mmol) of 1,2,3,3-tetramethyl-3H-indolium tris(pentafluoroethyl)trifluorophosphate are added to a solution of 0.194 g (1.31 mmol) of triethyl orthoformate in 15 cm³ of pyridine. The reaction mixture is heated for 13 h, and the solvent is subsequently removed by distillation. The residue is taken up in 15 cm³ of ethanol, and 0.11 g of NaOH in 50 cm³ of ethanol is added. After the ethanol has been removed by distillation, the residue is extracted with dichloromethane, and the organic phase is washed 3× with 100 cm³ of water and dried. Dichloromethane is removed by distillation, and the residue is dried under reduced pressure at 60° C., giving 0.79 g of 2-[3-(1,3-dihydro-1,3,3-trimethyl-2H-indol-2-ylidene)propenyl]-1,3,3-trimethyl-3H-indolium tris(pentafluoroethyl)trifluorophosphate. The yield is 74.3%.

$^{19}$F NMR (reference: $CCl_3F$; solvent: $CD_3CN$): −43.50 d,m (PF), −79.68 m ($CF_3$), −81.37 m ($2CF_3$), −86.95 d,m ($PF_2$), −115.05 dm ($CF_2$) −115.68 dm ($2CF_2$); $^1J_{P,F}$=888 Hz, $^1J_{P,F}$=906 Hz, $^2J_{P,F}$=85 Hz, $^2J_{P,F}$=98 Hz.

$^1$H NMR (reference: TMS; solvent: $CD_3CN$): 1.71 s (4$CH_3$), 3.57 s (2$CH_3$), 6.27 d (2H), 7.28 d,d,d (4H), 7.43 t,d (2H), 7.50 d (2H), 8.46 t (1H); 
$^3J_{H,H}$=13.5 Hz, $^3J_{H,H}$=7.6 Hz, $^5J_{H,H}$=1.0 Hz.

$^{31}$P NMR (reference: 85% $H_3PO_4$; solvent: $CD_3CN$): −148.0 q,m.

EXAMPLE 26

Preparation of 3-ethyl-2-[3-(3-ethyl-3H-benzothiazol-2-ylidene)propenyl]-benzothiazolium tris(pentafluoroethyl)trifluorophosphate

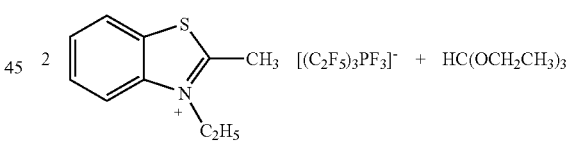

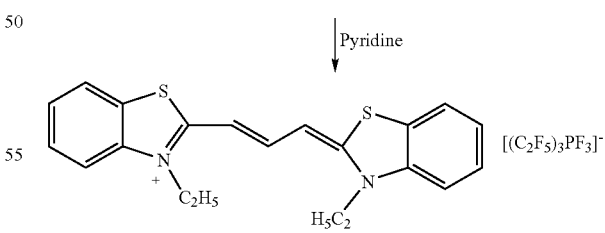

Analogously to Example 15, 0.28 g (1.89 mmol) of triethyl orthoformate are reacted with 2.35 g (3.77 mmol) of 1-ethyl-2-methylbenzothiazolium tris(pentafluoroethyl)trifluorophosphate in pyridine, giving 1.00 g of 3-ethyl-2-[3-(3-ethyl-3H-benzothiazol-2-ylidene)propenyl]benzothiazolium tris(pentafluoroethyl)trifluorophosphate in a yield of 65.4%.

$^{19}$F NMR (reference: $CCl_3F$; solvent: $CD_3CN$): −43.56 d,m (PF), −79.67 m ($CF_3$), −81.37 m ($2CF_3$), −86.95 d,m (PF$_2$), −114.99 dm (CF$_2$) −115.66 dm (2CF$_2$); $^1J_{P,F}$=888 Hz, $^1J_{P,F}$=903 Hz, $^2J_{P,F}$=80 Hz, $^2J_{P,F}$=97 Hz.

$^1$H NMR (reference: TMS; solvent: CD$_3$CN): 1.40 t (2CH$_3$), 4.25 q (2CH$_2$), 6.34 d (2H), 7.37 m (2H), 7.52 m (4H), 7.79 d (2H), 7.82 t (1H); $^3J_{H,H}$=12.7 Hz, $^3J_{H,H}$=7.1 Hz.

$^{31}$P NMR (reference: 85% H$_3$PO$_4$; solvent: CD$_3$CN): −148.1 q,m.

EXAMPLE 27

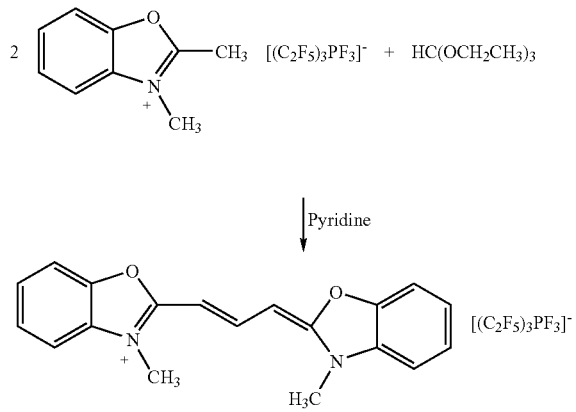

Analogously to Example 15, 0.38 g (2.56 mmol) of triethyl orthoformate are reacted with 3.03 g (5.11 mmol) of 1,2-dimethylbenzoxazolium tris(pentafluoroethyl)trifluorophosphate in pyridine, giving 3-methyl-2-[3-(3-methyl-3H-benzoxazol-2-ylidene)propenyl]benzoxazolium tris(pentafluoroethyl)trifluorophosphate in a yield of 31.3% after recrystallisation from toluene:dichloromethane (1:1).

$^{19}$F NMR (reference: CCl$_3$F; solvent: CD$_3$CN): −43.55 d,m (PF), −79.67 m (CF$_3$), −81.37 m (2CF$_3$), −86.94 d,m (PF$_2$), −115.01 dm (CF$_2$) −115.65 dm (2CF$_2$); $^1J_{P,F}$=888 Hz, $^1J_{P,F}$=904 Hz, $^2J_{P,F}$=84 Hz, $^2J_{P,F}$=97 Hz.

$^1$H NMR (reference: TMS; solvent: CD$_3$CN): 3.65 s (2CH$_3$), 5.84 d (2H), 7.36-7.52 m (6H), 7.59 d,d,d (2H), 8.44 t (1H); $^3J_{H,H}$=13.4 Hz, $^3J_{H,H}$=7.6 Hz, $^5J_{H,H}$=1.0 Hz.

$^{31}$P NMR (reference: 85% H$_3$PO$_4$; solvent: CD$_3$CN): −148.1 q,m.

EXAMPLE 28

Preparation of methyl 3-diazothiophene-2-carboxylate tris(pentafluoroethyl)trifluorophosphate

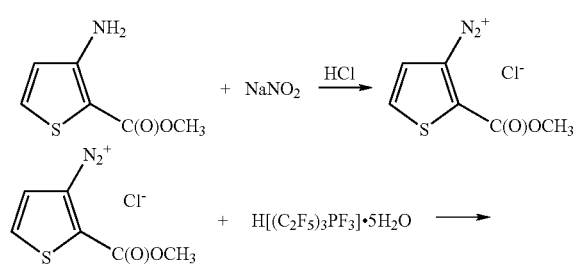

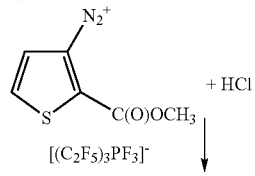

10.3 g (65.52 mmol) of methyl 3-aminothiophene-2-carboxylate are added with stirring to 25 cm$^3$ of a 6M hydrochloric acid solution. The reaction mixture is stirred at room temperature for a further 30 min. and subsequently cooled to −10° to −15° C. A solution of 4.52 g (65.51 mmol) of sodium nitrite in 10 cm$^3$ of water is added, and the diazonium chloride forms. 35.12 g (65.55 mmol) of H[(C$_2$H$_5$)$_3$ PF$_3$]×5H$_2$O are then added at this temperature.

The precipitate obtained is filtered off and washed with a cold solution of 10 cm$^3$ of H[(C$_2$H$_5$)$_3$ PF$_3$]×5H$_2$O in 20 cm$^3$ of water and twice with 10 cm$^3$ of cold methanol and subsequently dried at room temperature under reduced pressure, giving 38.90 g of methyl 3-diazothiophene-2-carboxylate tris(pentafluoroethyl)trifluorophosphate. This corresponds to a yield of 96.7%.

$^1$H NMR (reference: TMS; solvent: CD$_3$CN), ppm: 4.07 s (CH$_3$), 8.12 A,B (2H), $^3J_{A,B}$=5.5 Hz.

$^{19}$F NMR (reference: CCl$_3$F; solvent: CD$_3$CN), ppm: −43.57 d,m (PF), −79.68 m (CF$_3$), −81.37 m (2CF$_3$), −86.97 d,m (PF$_2$), −115.02 dm (CF$_2$) −115.62 dm (2CF$_2$); $^1J_{P,F}$=891 Hz, $^1J_{P,F}$=905 Hz, $^2J_{P,F}$=84 Hz, $^2J_{P,F}$=99 Hz.

$^{31}$P NMR (reference: 85% H$_3$PO$_4$; solvent: CD$_3$CN), ppm: −148.8 d,t,m.

EXAMPLE 29

Solubility Investigations of Nile Blue FAP

The dye prepared in Example 15 (Nile Blue FAP) from Nile Blue, where FAP denotes tris(pentafluoroethyl)trifluorophosphate, is exposed to various solvents.

As reference, the conventional dye Nile Blue with hydrogensulfate as anion is investigated under identical conditions.

TABLE 5

Solubility of Nile Blue with HSO$_4^-$ anion or (C$_2$F$_5$)$_3$PF$_3^-$ anion

| Solvent | Hydrogensulfate anion | [(C$_2$F$_5$)$_3$PF$_3$]$^-$ |
|---|---|---|
| Ethanol | +++ | +++ |
| Acetone | ++ | +++ |
| Water | +++ | − |
| Methylene chloride | + | +++ |
| Chloroform | + | ++ |
| Methanol | +++ | +++ |
| Benzene | − | + |
| Hexane | − | − |
| Diethyl ether | ++ | +++ |
| Acetonitrile | ++ | +++ |
| Tetrahydrofuran | + | +++ |
| Dimethyl carbonate | − | +++ |

Key:
− insoluble,
+ slightly soluble,
++ readily soluble,
+++ very readily soluble

EXAMPLE 30

Solubility Investigations of Safranine FAP

The dye prepared in Example 12 from safranine O is exposed to various solvents. The reference is safranine O with chloride as anion.

TABLE 6

Solubility of safranine O with Cl⁻ anion or (C₂F₅)₃PF₃⁻ anion

| Solvent | Cl⁻ | $[(C_2F_5)_3PF_3]^-$ |
|---|---|---|
| Ethanol | +++ | +++ |
| Acetone | ++ | +++ |
| Water | +++ | − |
| Methylene chloride | ++ | +++ |
| Chloroform | ++ | +++ |
| Methanol | +++ | +++ |
| Benzene | − | ++ |
| Hexane | − | − |
| Diethyl ether | − | +++ |
| Acetonitrile | ++ | +++ |
| Tetrahydrofuran | + | +++ |
| Dimethyl carbonate | − | +++ |

Key:
− insoluble,
+ slightly soluble,
++ readily soluble,
+++ very readily soluble

EXAMPLE 31

Preparation of a Xanthene Dye as Tetrakis(Trifluoromethyl)Borate from Rhodamine B

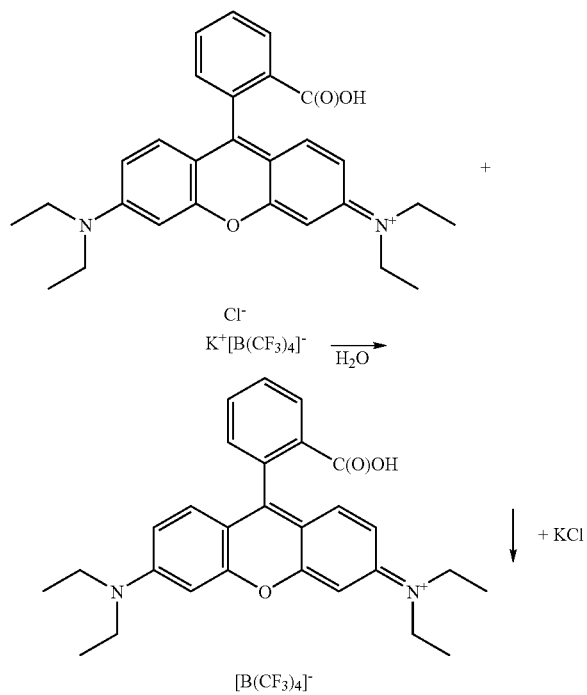

A solution of 0.233 g (0.72 mmol) of potassium tetrakis(trifluoromethyl)borate, K[B(CF₃)₄], in 5 cm³ of water is slowly added at room temperature to a solution of 0.312 g (0.65 mmol) of rhodamine B in 50 cm³ of water. The reaction mixture is stirred at room temperature for a further 30 minutes, and the precipitate is subsequently filtered. The filter cake is washed with 300 cm³ of water and then dried under reduced pressure. Yield: 86% (0.450 g; 0.62 mmol) of rhodamine B as tetrakis(trifluoromethyl)borate.

Elemental analysis (%) calc. for $C_{32}H_{31}BF_{12}N_2O_3$: C 52.6H 4.3 N 3.8; found: C 54.4 H 4.8 N 4.1.

$^1$H-NMR (300.13 MHz, CD₃CN, 25° C., TMS): δ 8.3-8.2 ppm (m, 1H), 7.9-7.7 ppm (m, 2H), 7.4-7.3 ppm (m, 1H), 7.0-6.8 ppm (m, 6H), 3.59 ppm (q, 8H), 1.24 ppm (t, 12H).

$^{11}$B-NMR (96.92 MHz, CD₃CN, 25° C., BF₃.OEt₂ external): δ −18.9 ppm.

$^{19}$F-NMR (282.41 MHz, CD₃CN, 25° C., CFCl₃) δ −61.6 ppm.

EXAMPLE 32

Preparation of an Oxazine Dye as Tetrakis(Trifluoromethyl)Borate from Nile Blue:

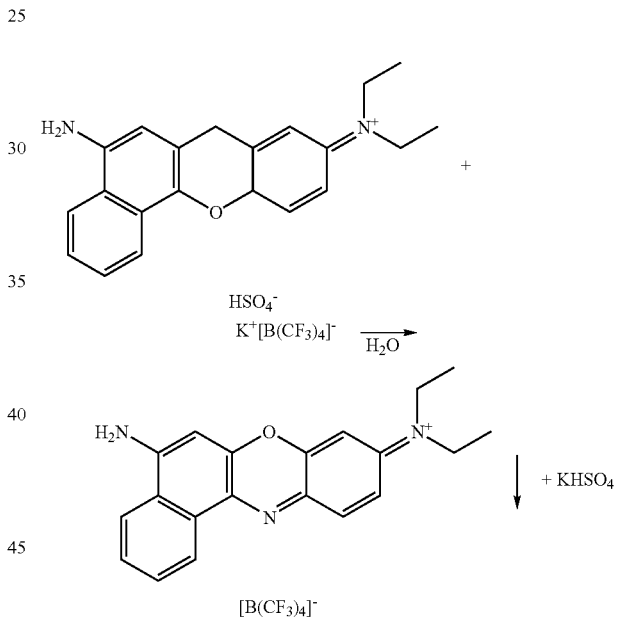

A solution of 0.383 g (1.18 mmol) of potassium tetrakis(trifluoromethyl)borate, K[B(CF₃)₄], in 5 cm³ of water is slowly added at room temperature to a solution of 0.444 g (1.07 mmol) of Nile Blue in 50 cm³ of water. The reaction mixture is stirred at room temperature for a further 30 minutes, and the precipitate is subsequently filtered. The filter cake is washed with 300 cm³ of water and then dried under reduced pressure. Yield: 84% (0.543 g; 0.90 mmol) of Nile Blue as tetrakis(trifluoromethyl)borate.

Elemental analysis (%) calc. for $C_{24}H_{24}BF_{12}N_3O$: C 47.3H 4.0 N 6.9; found: C 50.7H 3.6 N 7.4.

$^1$H-NMR (300.13 MHz, CD₃CN, 25° C., TMS): δ 8.8-8.7 ppm (m, 1H), 8.1-7.6 ppm (m, 4H), 7.64 ppm (s, 2H), 7.2-7.1 ppm (m, 1H), 6.7-6.8 ppm (m, 2H), 3.65 ppm (q, 4H), 1.30 ppm (t, 6H).

$^{11}$B-NMR (96.92 MHz, CD₃CN, 25° C., BF₃.OEt₂ external): δ −18.9 ppm.

$^{19}$F-NMR (282.41 MHz, CD$_3$CN, 25° C., CFCl$_3$): δ −61.6 ppm.

EXAMPLE 33

Preparation of an Azine Dye as Tetrakis(Trifluoromethyl)Borate from Safranine O

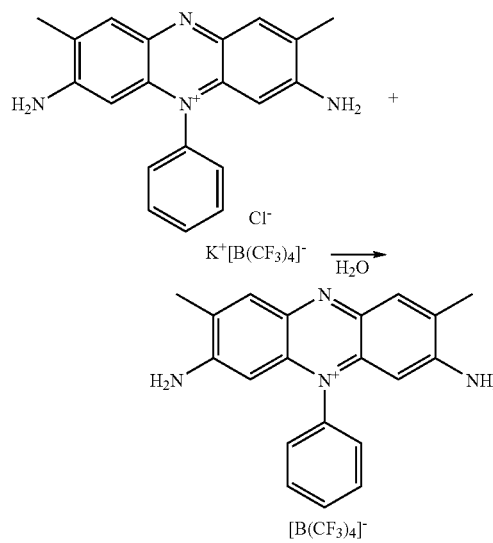

Analogously to Example 32, a solution of 0.412 g (1.17 mmol) of safranine O in 50 cm$^3$ is reacted with a solution of 0.421 g (1.29 mmol) of potassium tetrakis(trifluoromethyl)borate, K[B(CF$_3$)$_4$].

Yield: 68% (0.479 g; 0.80 mmol) of safranine O as tetrakis(trifluoromethyl)borate.

Elemental analysis (%) calc. for C$_{24}$H$_{19}$BF$_{12}$N$_4$: C 47.9 H 3.2 N 9.3; found: C 49.0 H 3.0 N 9.4.

$^1$H-NMR (300.13 MHz, CD$_3$CN, 25° C., TMS): δ 8.0-7.0 ppm (m, 9H), 6.0 ppm (s, 4H), 2.4-2.3 ppm (m, 6H).

$^{11}$B-NMR (96.92 MHz, CD$_3$CN, 25° C., BF$_3$.OEt$_2$ external): δ −18.9 ppm.

$^{19}$F-NMR (282.41 MHz, CD$_3$CN, 25° C., CFCb$_3$) δ −61.6 ppm.

EXAMPLE 34

Preparation of a Triphenylmethane Dye as Tetrakis(Trifluoromethyl)Borate from Crystal Violet

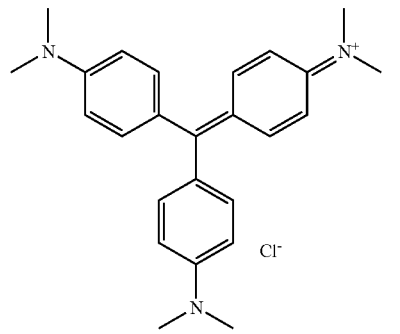

-continued

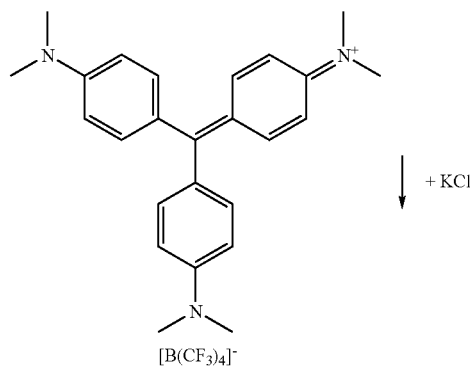

Analogously to Example 32, a solution of 0.204 g (0.50 mmol) of Crystal Violet in 50 cm$^3$ of water is reacted with a solution of 0.179 g (0.55 mmol) of potassium tetrakis(trifluoromethyl)borate, K[B(CF$_3$)$_4$], in 5 cm$^3$ of water.

Yield: 85% (0.281 g; 0.43 mmol) of Crystal Violet as tetrakis(trifluoromethyl)borate.

Elemental analysis (%) calc. for C$_{29}$H$_{30}$BF$_{12}$N$_3$: C 52.8 H 4.6 N 6.4; found: C 53.0 H 4.6 N 6.4.

$^1$H-NMR (300.13 MHz, CD$_3$CN, 25° C., TMS): δ 7.4-7.3 ppm (m, 6H), 7.0-6.8 ppm (m, 6H), 3.2 ppm (s, 18H).

$^{11}$B-NMR (96.92 MHz, CD$_3$CN, 25° C., BF$_3$.OEt$_2$ external): δ −18.9 ppm.

$^{19}$F-NMR (282.41 MHz, CD$_3$CN, 25° C., CFCl$_3$): δ −61.6 ppm.

EXAMPLE 35

Preparation of a Carbocyanine Dye as Tetrakis(Trifluoromethyl)Borate from 3,3'-diethyloxadicarbocyanine iodide (DODCI)

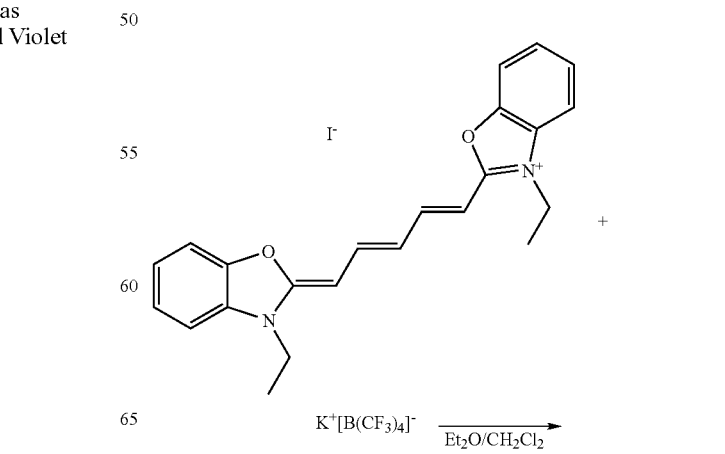

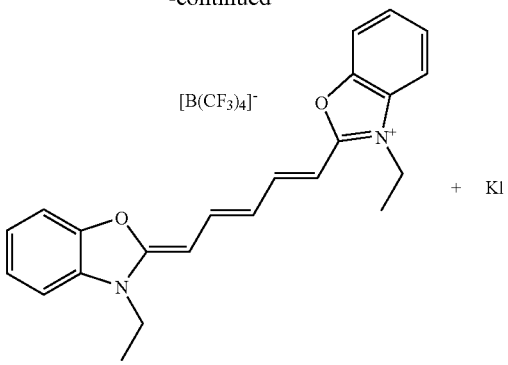

A solution of 0.051 g (0.16 mmol) of potassium tetrakis(trifluoromethyl)borate, K[B(CF$_3$)$_4$], in 5 cm$^3$ of ethanol is slowly added at room temperature to a solution of 0.034 g (0.07 mmol) of DODCI in 5 cm$^3$ of ethanol. The reaction mixture is stirred for 12 hours, and the solvent is subsequently removed by distillation. The residue is extracted twice with 10 cm$^3$ of dichloromethane each time, dried and all volatile constituents are removed under reduced pressure. Yield: 91% (0.041 g; 0.06 mmol) of 3,3'-diethyloxadicarbocyanine tetrakis(trifluoromethyl)borate.

Elemental analysis (%) calc. for C$_{27}$H$_{23}$BF$_{12}$N$_2$O$_2$: C 50.2 H 3.6 N 4.3; found: C 46.5 H 3.4 N 3.7.

$^1$H-NMR (300.13 MHz, CD$_3$CN, 25° C., TMS): δ 7.8 ppm (t, 2H), 7.6-7.5 ppm (m, 2H), 7.4-7.3 ppm (m, 6H), 6.3 ppm (t, 1H), 5.8 ppm (d, 2H), 4.1 ppm (q, 4H), 1.4 ppm (t, 6H).

$^{11}$B-NMR (96.92 MHz, CD$_3$CN, 25° C., BF$_3$.OEt$_2$ external): δ −18.9 ppm.

$^{19}$F-NMR (282.41 MHz, CD$_3$CN, 25° C., CFCl$_3$): δ −61.6 ppm.

EXAMPLE 36

Preparation of 2-[3-(1,3-dihydro-1,3,3-trimethyl-2H-indol-2-ylidene)propenyl]-1,3,3-trimethyl-3H-indolium tetrakis(trifluoromethyl)borate

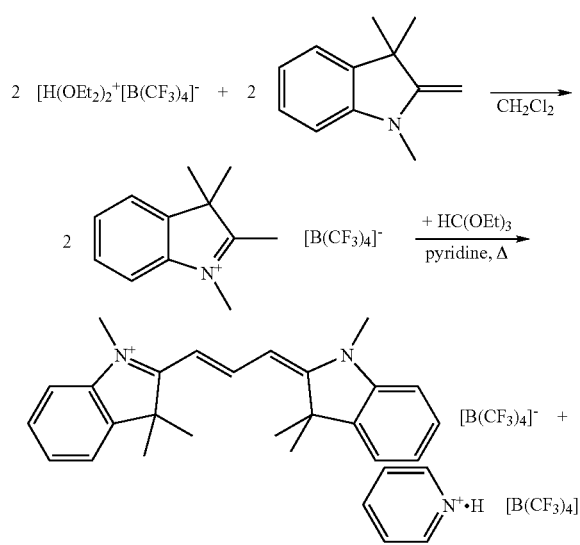

0.436 g (0.55 mmol) of [H(OEt$_2$)$_2$][B(CF$_3$)$_4$] and 0.091 g (0.53 mmol) of 2-methylene-1,3,3-methylindoline are each dissolved in 4 cm$^3$ of dichloromethane under an argon atmosphere and slowly combined with stirring at 0° C. The reaction mixture is warmed to room temperature, and all volatile constituents are subsequently removed under reduced pressure. In an argon atmosphere, the resultant 1,2,3,3-tetramethylindolium tetrakis(trifluoromethyl)borate is dissolved in 5 cm$^3$ of anhydrous pyridine, and 0.043 g (0.29 mmol) of triethyl orthoformate are added. The mixture is heated under reflux for 15 h. After cooling, all volatile constituents are removed under reduced pressure, and the solid is dissolved in 100 cm$^3$ of dichloromethane. 0.25 g (4.5 mmol) of potassium hydroxide are dissolved in 10 cm$^3$ of distilled water and added to the dichloromethane solution with stirring. After 2 h with stirring, the aqueous phase is separated off, and the organic phase is dried using potassium carbonate. The solution is filtered, and the solvent is removed by distillation. The crude product is purified by crystallisation from dichloromethane/pentane. Yield: 75% (0.117 g; 0.20 mmol) of 2-[3-(1,3-dihydro-1,3,3-trimethyl-2H-indol-2-ylidene)propenyl]-1,3,3-trimethyl-3H-indolium tetrakis(trifluoromethyl)borate (based on 2-methylene-1,3,3-methylindoline).

$^1$H-NMR (CD$_3$CN, 25° C., TMS): δ: 8.46 ppm (t, 1H), 7.56-7.49 ppm (m, 2H), 7.48-7.40 ppm (m, 2H), 7.35-7.25 ppm (m, 4H), 6.28 ppm (d, 2H), 3.57 ppm (s, 6H), 1.72 ppm (s, 12H).

$^{11}$B-NMR (CD$_3$CN, 25° C., BF$_3$.OEt$_2$ external): δ: −18.9 ppm.

$^{19}$F-NMR (CD$_3$CN, 25° C., CFCl$_3$): δ: −61.6 ppm.

EXAMPLE 37

TABLE 7

Solubility investigations of the dyes prepared in accordance with Examples 31 to 34

| Dye[a] | H$_2$O | CH$_3$CN | Ethanol | CH$_2$Cl$_2$ | Pentane |
| --- | --- | --- | --- | --- | --- |
| Rhodamine | <0.01 | >1 | >2 | >3 | insoluble |
| Nile Blue | <0.01 | >2 | >3 | >5 | insoluble |
| Safranine O | <0.01 | >2 | >5 | >5 | insoluble |
| Crystal Violet | insoluble | >5 | >10 | >10 | insoluble |

[a]Anion: [B(CF$_3$)$_4$]$^-$

The solubilities are indicated in g/cm$^3$.

EXAMPLE 38

Preparation of an Azo Dye as Bis(Trifluoromethanesulfonyl)Imide from Janus Green

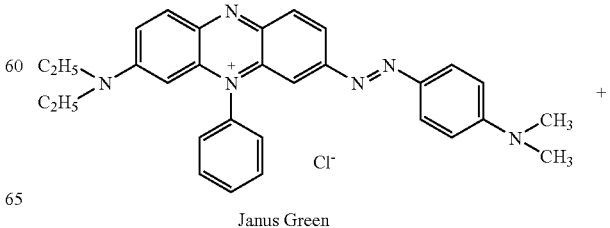

Janus Green

-continued

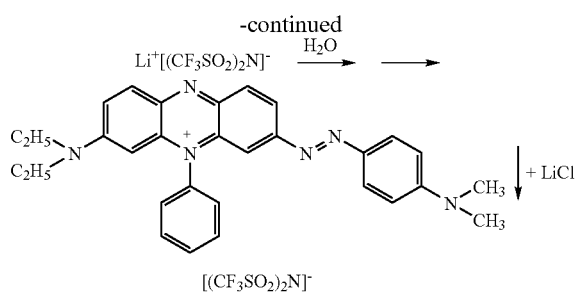

0.43 g (0.841 mmol) of the dye Janus Green are dissolved in 100 cm³ of water. 0.25 g (0.871 mmol) of lithium bis(trifluoromethanesulfonyl)imide, Li[(CF₃SO₂)₂N], in 5 cm³ of water are added dropwise to this solution at room temperature with stirring. The reaction mixture is stirred for a further 5 min. The precipitate is filtered off and washed 3× with 50 cm³ of water. The residue is dried under a reduced pressure of 1.3 Pa and at 80° C., giving 0.44 g of Janus Green as bis(trifluoromethanesulfonyl)imide, which corresponds to a yield of 69.3%.

$^{19}$F NMR (reference: CCl₃F; CD₃CN): −78.92 s (2CF₃).
$^1$H NMR (reference: TMS; CD₃CN): 0.99 m (CH₃), 1.25 m (CH₃), 3.04 m (2CH₃), 3.29 m (CH₂), 3.65 m (CH₂), 5.64 d (1H), 6.58 s (1H), 6.60 s (1H), 7.03 d (1H), 7.47-7.53 m (4H), 7.57-7.62 m (1H), 7.83-7.93 m (5H), 8.10 d (1H); $J_{H,H}$=2.4 Hz; $J_{H,H}$=1.5 Hz; $J_{H,H}$=8.9 Hz.

EXAMPLE 39

Preparation of an Azine Dye as Bis(Trifluoromethanesulfonyl)Imide from Safranine O

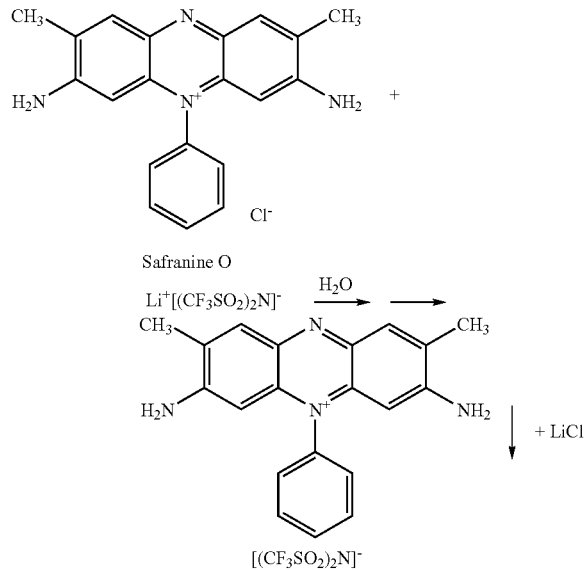

0.64 g (1.82 mmol) of the dye safranine O are dissolved in 100 cm³ of water. 0.60 g (2.09 mmol) of lithium bis(trifluoromethanesulfonyl)imide, Li[(CF₃SO₂)₂N], in 5 cm³ of water are added dropwise to this solution at room temperature with stirring. The reaction mixture is stirred for a further 5 min. The precipitate is filtered off and washed 3× with 50 cm³ of water. The residue is dried under a reduced pressure of 1.3 Pa and at 80° C., giving 0.99 g of safranine O as bis(trifluoromethanesulfonyl)imide, which corresponds to a yield of 91.3%.

$^{19}$F NMR (reference: CCl₃F; CD₃CN): −78.93 s (2CF₃).
$^1$H NMR (reference: TMS; CD₃CN): 2.30 br.s (2CH₃), 5.90-6.10 br.s (2NH₂), 7.44-7.50 m (2H), 7.72-7.88 m (7H).

EXAMPLE 40

Preparation of a Xanthene Dye as Bis(Trifluoromethanesulfonyl)Imide from Rhodamine B

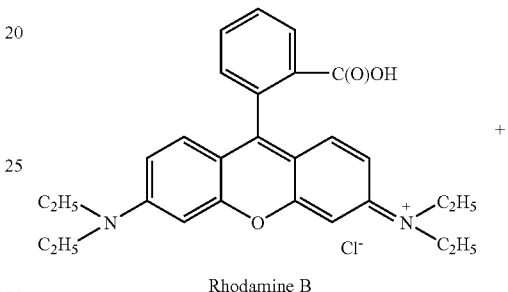

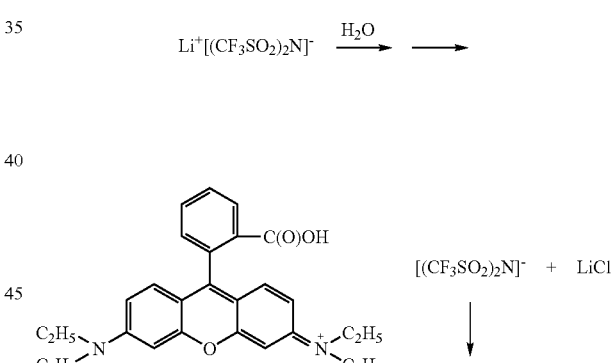

0.61 g (1.27 mmol) of the dye rhodamine B are dissolved in 100 cm³ of water. 0.38 g (1.32 mmol) of lithium bis(trifluoromethanesulfonyl)imide, Li[(CF₃SO₂)₂N], in 3 cm³ of water are added dropwise to this solution at room temperature with stirring. The reaction mixture is stirred for a further 5 min. The precipitate is filtered off and washed 3× with 50 cm³ of water. The residue is dried under a reduced pressure of 1.3 Pa and at 80° C., giving 0.85 g of rhodamine B as bis(trifluoromethanesulfonyl)imide, which corresponds to a yield of 92.5%.

$^{19}$F NMR (reference: CCl₃F; CD₃CN): −78.94 s (2CF₃).
$^1$H NMR (reference: TMS; CD₃CN): 1.23 t (4CH₃), 3.58 q (4CH₂), 6.79 s (2H), 6.87 d, 6.89 d (2H; A,B), 7.02 s, 7.04 s (2H; A,B), 7.32 d (1H), 7.70-7.83 m (2H), 8.23 d (1H); $^3J_{H,H}$=7.1 Hz, $J_{A,B}$=9.2 Hz, $J_{H,H}$=2.0 Hz, $J_{H,H}$=7.5 Hz, $J_{H,H}$=7.7 Hz.

EXAMPLE 41

Preparation of an Oxazine Dye as Bis(Trifluoromethanesulfonyl)Imide from Nile Blue

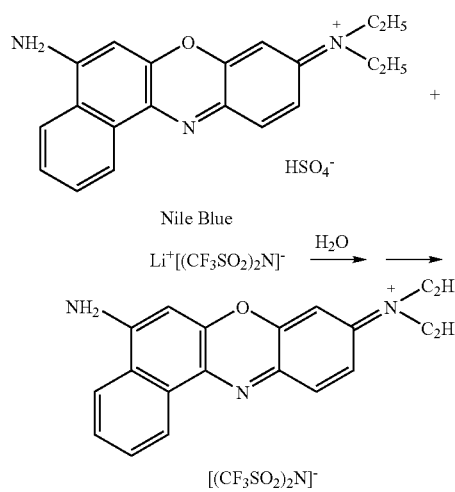

0.63 g (1.52 mmol) of the dye Nile Blue hydrogensulfate are dissolved in 100 cm$^3$ of water. 0.45 g (1.57 mmol) of lithium bis(trifluoromethanesulfonyl)imide, Li[(CF$_3$SO$_2$)$_2$N], in 5 cm$^3$ of water are added dropwise to this solution at room temperature with stirring. The reaction mixture is stirred for a further 5 min. The precipitate is filtered off and washed 3× with 50 cm$^3$ of water. The residue is dried under reduced pressure giving 0.83 g of Nile Blue as bis(trifluoromethanesulfonyl)imide, which corresponds to a yield of 87.8%.

$^{19}$F NMR (reference: CCl$_3$F; CD$_3$CN): −78.91 s (2CF$_3$).
$^1$H NMR (reference: TMS; CD$_3$CN): 1.29 t (2CH$_3$), 3.63 q (2CH$_2$), 6.68 s (1H), 6.73 d (1H), 7.18 d,d (1H), 7.60 br.s (NH$_2$), 7.70 d (1H), 7.74-8.05 m (3H), 8.73 d (1H); $^3J_{H,H}$=7.1 Hz, $J_{H,H}$=2.6 Hz, $J_{H,H}$=2.7 Hz, $J_{H,H}$=9.4 Hz, $J_{H,H}$=8.2 Hz.

EXAMPLE 42

Preparation of 1,2,3,3-tetramethyl-3H-indolium bis(trifluoromethanesulfonyl)imide

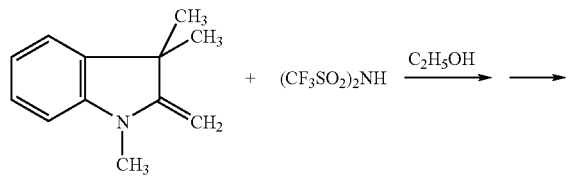

1.88 g (10.85 mmol) of 2-methylene-1,3,3-methylindoline (Fischer base) are added over the course of a few minutes with stirring to a solution of 3.054 g (10.86 mmol) of bis(trifluoromethanesulfonyl)imide, (CF$_3$SO$_2$)$_2$NH, in 15 ml of dry ethanol. The reaction mixture is stirred at room temperature for a further 5 min. The solvent is subsequently removed by distillation, and the residue is dried under a reduced pressure of 1.3 Pa and at 60° C., giving 4.86 g of 1,2,3,3-tetramethyl-3H-indolium bis(trifluoromethanesulfonyl)imide, corresponding to a yield of 98.6%.

Melting point (m.p.): 86-87° C.
$^{19}$F NMR (reference: CCl$_3$F; CD$_3$CN): −78.88 s (2CF$_3$).
$^1$H NMR (reference: TMS; CD$_3$CN): 1.55 s (2CH$_3$), 2.69 q (CH$_3$), 3.92 q (CH$_3$), 7.60-7.77 m (4H), $^5J_{H,H}$=0.7 Hz.

EXAMPLE 43

Preparation of 3-ethyl-2-methylbenzothiazolium bis(trifluoromethanesulfonyl)imide

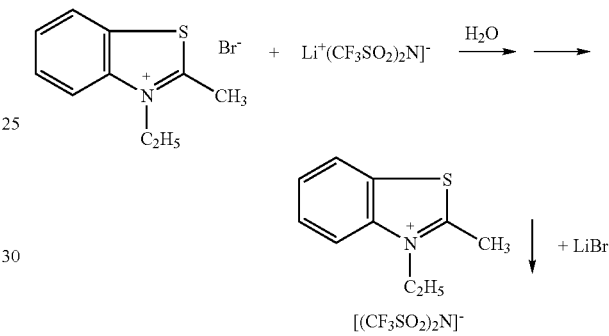

2.22 g (7.73 mmol) of lithium bis(trifluoromethanesulfonyl) imide, Li[(CF$_3$SO$_2$)$_2$N], in 5 ml of water are added dropwise with stirring to a solution of 2.00 g (7.75 mmol) of 3-ethyl-2-methylbenzothiazolium bromide in 50 ml of water. The lower liquid phase is extracted a number of times with 50 ml of dichloromethane, and the combined organic phases are dried using Mg$_2$SO$_4$. The solvent is subsequently removed by distillation, and the residue is dried under a reduced pressure of 1.3 Pa at 60° C., giving 3.14 g of 3-ethyl-2-methylbenzothiazolium bis(trifluoromethanesulfonyl)imide, corresponding to a yield of 88.7%.

$^{19}$F NMR (reference: CCl$_3$F; CD$_3$CN): −78.89 s (2CF$_3$).
$^1$H NMR (reference: TMS; CD$_3$CN): 1.53 t (CH$_3$), 3.10 s (CH$_3$), 4.67 q (CH$_2$), 7.78 t (1H), 7.88 t (1H), 8.10 d (1H), 8.22 d (1H); $^3J_{H,H}$=8.4 Hz, $^3J_{H,H}$=7.4 Hz.

EXAMPLE 44

Preparation of 2-[3-(1,3-dihydro-1,3,3-trimethyl-2H-indol-2-ylidene)propenyl]-1,3,3-trimethyl-3H-indolium bis(trifluoromethanesulfonyl)imide

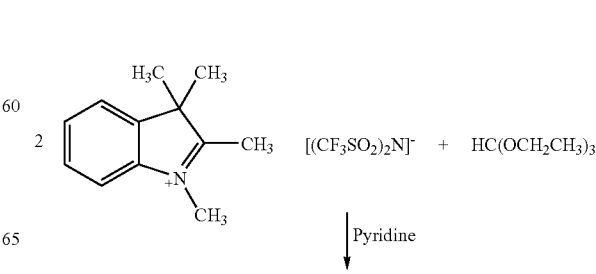

-continued

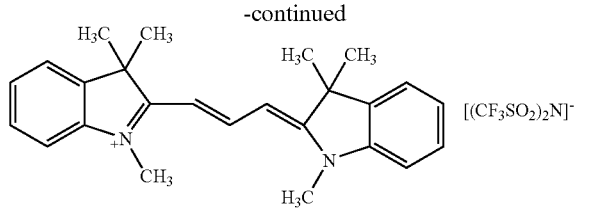

4.751 g (10.46 mmol) of 1,2,3,3-tetramethyl-3H-indolium bis(trifluoromethanesulfonyl)imide are added to a solution of 0.783 g (5.28 mmol) of triethyl orthoformate in 15 ml of dry pyridine. The reaction mixture is heated at an oil-bath temperature of 120-125° C. for 30 hours. After the solvent has been removed by distillation under a reduced pressure of 1.3 Pa and at 80° C., the solid is washed a number of times with cold ethanol and dried under a reduced pressure of 1.3 Pa and at 60° C., giving 2.90 g of 2-[3-(1,3-dihydro-1,3,3-trimethyl-2H-indol-2-ylidene)propenyl]-1,3,3-trimethyl-3H-indolium bis(trifluoromethanesulfonyl)imide, corresponding to a yield of 87%.

$^{19}$F NMR (reference: CCl$_3$F; CD$_3$CN): −78.93 s (2CF$_3$).

$^1$H NMR (reference: TMS; CD$_3$CN): 1.71 s (4CH$_3$), 3.57 s (2CH$_3$), 6.27 d (2H), 7.27 d (2H), 7.30 d (2H), 7.43 t,d (2H), 7.50 d (2H), 8.45 t (1H); $^3J_{H,H}$=13.5 Hz, $^3J_{H,H}$=7.6 Hz, $^5J_{H,H}$=1.0 Hz.

EXAMPLE 45

Preparation of 3-ethyl-2-[3-(3-ethyl-3H-benzothiazol-2-ylidene)propenyl]-benzothiazolium bis(trifluoromethanesulfonyl)imide

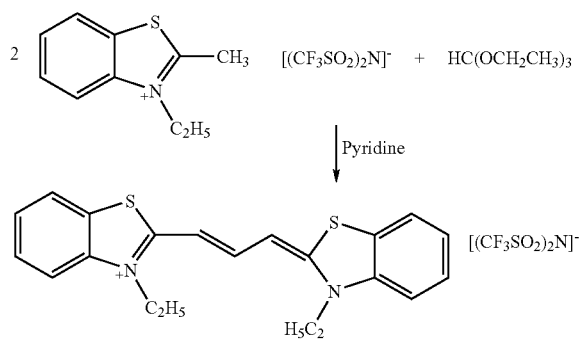

3.03 g (6.61 mmol) of 3-ethyl-2-methylbenzothiazolium bis(trifluoromethanesulfonyl)imide are added to a solution of 0.489 g (3.30 mmol) of triethyl orthoformate in 15 ml of dry pyridine. The reaction mixture is heated at an oil-bath temperature of 110-115° C. for 15 hours. After the solvent has been removed by distillation under a reduced pressure of 1.3 Pa and at 80° C., the solid is washed a number of times with cold ethanol and dried under a reduced pressure of 1.3 Pa and at 60° C., giving 1.83 g of 3-ethyl-2-[3-(3-ethyl-3H-benzothiazol-2-ylidene)propenyl]benzothiazolium bis(trifluoromethanesulfonyl)imide, corresponding to a yield of 85.9%.

$^{19}$F NMR (reference: CCl$_3$F; CD$_3$CN): −78.94 s (2CF$_3$).

$^1$H NMR (reference: TMS; CD$_3$CN): 1.40 t (2CH$_3$), 4.25 q (2CH$_2$), 6.35 d (2H), 7.37 m (2H), 7.52 m (4H), 7.79 d (2H), 7.82 t (1H); $^3J_{H,H}$=12.7 Hz, $^3J_{H,H}$=7.1 Hz, $J_{H,H}$=8.1 Hz.

EXAMPLE 46

Solubility investigations of Nile Blue as bis(trifluoromethanesulfonyl)imide

The dye prepared in Example 41 from Nile Blue is exposed to various solvents.

As reference, the conventional dye Nile Blue with hydrogensulfate as anion is investigated under identical conditions.

TABLE 8

| Solubility of Nile Blue with HSO$_4$⁻ or [(CF$_3$SO$_2$)$_2$N]⁻ | | |
|---|---|---|
| Solvent | Hydrogensulfate anion | [(CF$_3$SO$_2$)$_2$N]⁻ |
| Water | +++ | − |
| Methanol | +++ | +++ |
| Benzene | − | + |
| Hexane | − | − |
| Diethyl ether | ++ | ++ |
| Tetrahydrofuran | + | +++ |
| Dimethyl carbonate | − | ++ |

Key:
− insoluble,
+ soluble,
++ readily soluble,
+++ very readily soluble

EXAMPLE 47

Solubility Investigations of Rhodamine B as bis(trifluoromethanesulfonyl)imide

The dye prepared in Example 40 from rhodamine B is exposed to various solvents.

As reference, the conventional dye rhodamine B with chloride as anion is investigated under identical conditions.

TABLE 9

| Solubility of rhodamine B with Cl⁻ or [(CF$_3$SO$_2$)$_2$N]⁻ | | |
|---|---|---|
| Solvent | Cl⁻ | [(CF$_3$SO$_2$)$_2$N]⁻ |
| Water | +++ | − |
| Methanol | +++ | +++ |
| Benzene | −+ | ++ |
| Hexane | − | − |
| Diethyl ether | −+ | ++ |
| Tetrahydrofuran | ++ | +++ |
| Dimethyl carbonate | ++ | +++ |
| Ethyl acetate | + | +++ |

Key:
− insoluble,
+ soluble,
++ readily soluble,
+++ very readily soluble

EXAMPLE 48

Solubility Investigations of Safranine O as bis(trifluoromethanesulfonyl)imide

The dye prepared in Example 39 from safranine O is exposed to various solvents.

As reference, the conventional dye safranine O with chloride as anion is investigated under identical conditions.

TABLE 10

Solubility of safranine O with Cl⁻ or [(CF₃SO₂)₂N]⁻

| Solvent | Cl⁻ | [(CF₃SO₂)₂N]⁻ |
|---|---|---|
| Water | +++ | − |
| Methanol | +++ | +++ |
| Benzene | − | + |
| Hexane | − | − |
| Diethyl ether | − | ++ |
| Tetrahydrofuran | + | +++ |
| Dimethyl carbonate | −+ | ++ |
| Ethyl acetate | − | +++ |

Key:
− insoluble,
+ soluble,
++ readily soluble,
+++ very readily soluble

EXAMPLE 49

Solubility Investigations of Janus Green as bis(trifluoromethanesulfonyl)imide

The solid prepared in Example 38 from Janus Green is exposed to various solvents.

As reference, the conventional dye Janus Green with chloride as anion is investigated under identical conditions.

TABLE 11

Solubility of Janus Green with Cl⁻ or [(CF₃SO₂)₂N]⁻

| Solvent | Cl⁻ | [(CF₃SO₂)₂N]⁻ |
|---|---|---|
| Water | +++ | − |
| Methanol | +++ | +++ |
| Benzene | − | ++ |
| Hexane | − | − |
| Diethyl ether | − | + |
| Tetrahydrofuran | ++ | +++ |
| Dimethyl carbonate | +− | ++ |
| Ethyl acetate | + | +++ |

Key:
− insoluble,
+ soluble,
++ readily soluble,
+++ very readily soluble

The invention claimed is:

1. A cationic dye of formula I $$CAT^+Y^- \qquad (I),$$

wherein
CAT⁺ is a cation of a polymethine dye, and
Y⁻ is an anion according to formula (II-2)

$$[P(C_{p2}F_{2p2+1-m2}H_{m2})_{y2}F_{6-y2}]^- \qquad (II-2)$$

p2 is 1 to 20,
m2 is 0, 1, 2 or 3,
y2 is 1, 2, 3 or 4.

2. A dye according to claim 1, wherein CAT⁺ is a cation of a cyanine dye.
3. A dye according to claim 1, wherein CAT⁺ is a cation of a carbocyanine dye.
4. A dye according to claim 1, wherein CAT⁺ is a cation of an azacarbocyanine dye.
5. A dye according to claim 1, wherein CAT⁺ is a cation of a diazacarbocyanine dye.
6. A dye according to claim 1, wherein CAT⁺ is a cation of a triazacarbocyanine dye.
7. A dye according to claim 1, wherein CAT⁺ is a cation of a hemicyanine dye.
8. A dye according to claim 1, wherein CAT⁺ is a cation of a diazahemicyanine dye.
9. A dye according to claim 1, wherein p2 is 1, 2, 3, 4, 5, 6, 7 or 8.
10. A dye according to claim 1, wherein p2 is 2, 3 or 4.
11. A dye according to claim 1, wherein Y⁻ is ⁻PF₃(C₂F₅)₃, ⁻PF₃(C₄F₉)₃, ⁻PF₃(C₃F₇)₃ or ⁻PF₄(C₂F₅)₂.

* * * * *